US008781750B2

(12) United States Patent
Stuart et al.

(10) Patent No.: US 8,781,750 B2
(45) Date of Patent: Jul. 15, 2014

(54) CELL-TYPE-SPECIFIC PATTERNS OF GENE EXPRESSION

(75) Inventors: Robert O. Stuart, San Diego, CA (US); Elizabeth Duff Stuart, legal representative, San Diego, CA (US); William Wachsman, San Diego, CA (US); Daniel Mercola, Rancho Santa Fe, CA (US); Michael McClelland, Encinitas, CA (US); Jessica Wang-Rodriguez, San Diego, CA (US); David Tarin, San Diego, CA (US); Charles C. Berry, San Diego, CA (US); Karen Arden, San Diego, CA (US); Linda Wasserman, La Jolla, CA (US); Steven Goodison, Jacksonville, FL (US); Igor Klacansky, San Diego, CA (US)

(73) Assignees: The Regents of the University of California, Oakland, CA (US); Sidney Kimmel Cancer Center, San Diego, CA (US); Ludwig Institute for Cancer Research, New York, NY (US)

( * ) Notice: Subject to any disclaimer, the term of this patent is extended or adjusted under 35 U.S.C. 154(b) by 1747 days.

(21) Appl. No.: 11/033,056

(22) Filed: Jan. 10, 2005

(65) Prior Publication Data
US 2006/0292572 A1    Dec. 28, 2006

Related U.S. Application Data

(60) Provisional application No. 60/535,382, filed on Jan. 9, 2004, provisional application No. 60/536,163, filed on Jan. 12, 2004.

(51) Int. Cl.
*G01N 33/48* (2006.01)
*C12Q 1/00* (2006.01)

(52) U.S. Cl.
USPC ................................................. 702/19; 435/4

(58) Field of Classification Search
None
See application file for complete search history.

(56) References Cited

U.S. PATENT DOCUMENTS

2006/0172347 A1* 8/2006 Mellor et al. ................. 435/7.23

FOREIGN PATENT DOCUMENTS

| DE | 10159404 | 6/2003 |
|---|---|---|
| WO | 2005/028677 | 3/2005 |
| WO | WO 2005/068664 | 7/2005 |

OTHER PUBLICATIONS

Naughteon et al., "Scatter Factor-Hepatocyte Growth Factor Elevation in the Serum of Patients With Prostate Cancer," vol. 165, pp. 1325-1328 (2001).*
Cazares et al., "Normal, Benign, Preneoplastic, and Malignant Prostate Cells Have Distinct Protein Expression Profiles Resolved by Surface Enhanced Laser Desorption/Ionization Mass Spectrometry," (Clinical Cancer Research, vol. 8 (2002) pp. 2541-2552).*
Xu et al. "Identification of Differentially Expressed Genes in Human Prostate Cancer Using Subtraction and Microarray," (Cancer Research, vol. 60 (2000) p. 1677-1682).*
Xiao et al. teach "Qauntitation of Serum Prostate-specific Membrane Antigen by a Novel Protein Biochip Immunoassay Discriminates Benign from Malignant Prostate Disease," Cancer Res. vol. 61 (2001) 6029-6033.*
Peng Lu et al.: "Expression deconvolution: A reinterpretation of DNA microarray data reveals dynamic changes in cell populations"; Proceedings of the National academy of Sciences of the United States of America, vol. 100, No. 18; Sep. 2, 2003; pp. 10370-10375.
D. Venet et al.: "Separation of samples into their constituents using gene expression data"; Bioinformatics 2001; vol. 17, suppl. 1; 2001; pp. S279-S287.
Jennifer Tuxhorn, et al.: "Reactive stroma in human prostate cancer: induction of myofibroblast phenotype and extracellular matrix remodeling"; Clinical Cancer Research: An Official Journal of the American Association for Cancer Research Sep. 2002, vol. 8, No. 9; Sep. 2002; pp. 2912-2923.
D. Singh, et al: "Gene expression of clinical prostate concer behavious"; Cancel Cell, US, vol. 1; Mar. 2002; pp. 203-209.
S. Bhattacharya, et al.: "Overcoming confounded controls in the analysis of gene expression data from microarray experiments"; Applied Bioinformatics, Open Mind Journals, Auckland, NZ, vol. 2, No. 4; 2003; pp. 197-208.
Debashis Ghosh: "Mixture models for assessing differential expression in complex tissues using microarray data"; Bioinformatics (Ocford), vol. 20, No. 11; Jul. 22, 2004; pp. 1663-1669.
Robert O. Stuart, et al.: "In silico dissection of cell-type-associated patterns of gene expression in prostate cancer"; Proceedings of the National Academy of Sciences of the United States of America, vol. 101, No. 2; Jan. 13, 2004; pp. 615-620.
Atschul et al., "Basic Local Alignment Search Tool," *J. Molec. Biol.* 215:403-410, 1990.
Bibikova et al., Expression signatures that correlated with Gleason score and relapse in prostate cancer, *Genomics* 89(6): 666-72, 2007.
Chuang et al., "Specific and heritable genetic interference by double-stranded RNA in *Arabidopsis thaliana*," *Proc. Natl. Acad. Sci. U.S.A.* 97:4985, 2000.
Devereux et al., "A comprehensive set of sequence analysis programs for the VAX," *Nucl. Acids Res.* 12(I):387, 1984.
Efron et al., "Empirical Bayes Analysis of a Microarray Experiment," *J. Am. Stat. Assoc.* 96, 1151-1160, 2001.
Evans et al., "Design of nonpeptidal ligands for a peptide receptor: cholecystokinin antagonists," *J. Med. Chem.* 30:1229, 1987.
Fauchere, "Elements for the Rational Design of Peptide Drugs," *J. Adv. Drug Res.* 15:29, 1986.

(Continued)

*Primary Examiner* — Anna Skibinsky
(74) *Attorney, Agent, or Firm* — Fish & Richardson P.C.

(57) ABSTRACT

Among the methods, compositions, combinations and kits provided herein are those for determining gene expression levels in one or more cell types in heterogeneous cell samples, for identifying genes differentially expressed in different cell types, and for detecting a cell type in a sample from a subject. Also provided herein are methods, compositions, combinations and kits for determining gene expression levels in cells corresponding to phenotypes, and for identifying a phenotype of a subject by detecting differentially expressed genes.

4 Claims, 4 Drawing Sheets

(56) References Cited

OTHER PUBLICATIONS

Febbo and Sellers, "Use of expression analysis to predict outcome after radical prostatectomy" *J. Urol.* 170(6 Pt 2):S11-9, 2003.
Gante, "Peptidomimetics-Tailored Enzyme Inhibitors," Angew. Chem. Int. Ed. Engl., 33:1699-1720, 1994.
Goldspiel et al., "Human gene therapy," *Clin. Pharm.* 12:488-505, 1993.
Gribskov et al., "Sigma factors from *E.coli, subtilis*, phange SP01, and phage T4 are homologous proteins," *Nucl. Acids Res.* 14:6745, 1986.
Howe et al., "Annual report to the nation on the status of cancer (1973 through 1998), featuring cancers with recent increasing trends," *J. Natl. Cancer Inst.* 93, 824-842, 2001.
Ihaka and Gentleman, "R: A language for data analysis and graphics," *J. Computat. Graph. Stat.* 5:299-314, 1996.
Kononen et al., "Tissue microarrays for high-throughput molecular profiling of tumor specimens," *Nat. Med.* 4(7):844-7, 1998.
Kozak, "Structural features in Eukaryotic mRNAs that modulate the initiation of translation," *J. Biol. Chem.* 266:19867-19870, 1991.
Lander, "The new genomics: global views of biology," *Science* 274:536-539 1996.
Li and Wong, "Model-based analysis of oligonucleotide arrays: expression index computation and outlier detection," *Proc. Natl. Acad. Sci. U.S.A.* 98, 31-36, 2001.
Liang and Zeger, "Longitudinal data analysis using generalized linear models," *Biometrika* 73:13-22, 1986.
Luthman and Hacksell, "Bioactive Ether-linked Phospholipids: Platelet-activating Factor (PAF) and Analogs," Chapter 15 in *A Textbook of Drug Design and Development*, Krogsgaard-Lars, 2nd Ed., Harwood Academic Publishers (1996) pp. 386-406.
Morgan and Anderson, "Human gene therapy," *Ann. Rev. Biochem.* 62:191-217, 1993.
Mulligan, "The basic science of gene therapy," *Science* 260:926-932, 1993.
Needleman et al., "A general method applicable to the search for similarities in the amino acid sequence of two proteins," *J. Mol. Biol.* 48:443, 1970.
Pearson et al., "Improved tools for biological sequence comparison," *Proc. Natl. Acad. Sci. U.S.A.* 85:2444, 1988.
Robinson, "Gene therapy—proceeding from laboratory to clinic," *TIBECH* 11 (5):155-215, 1993.
Sagliocco et al., "Identification of proteins of the yeast protein map using genetically manipulated strains and peptide-mass fingerprinteg," *Yeast* 12:1519-1533, 1996.
Schwartz and Dayhoff, eds., *Atlas of Protein Sequence and Structure*, National Biomedical Research Foundation (1979) pp. 353-358.
Shevchenko et al., "Linking genome and proteome by mass spectrometry: Large-scale identification of yeast proteins from two dimensional gels," *Proc. Natl. Acad. Sci. U.S.A.* 93:1440-1445, 1996.
Smith and Waterman, "Comparison of biosequences," *Adv. Appl. Math.* 2:482, 1981.
Stephenson et al., "Integration of gene expression profiling and clinical variables to predict prostate carcinoma recurrence after radial prostatectomy," *Cancer* 104(2):209-8, 2005.
Stuart et al., "In silico dissection of cell-type-associated patterns of gene expression in prostate cancer" *Proc. Natl. Acad. Sci. U.S.A.* 101(2):615-20, 2004.
Tibshirani et al., "Diagnosis of multiple cancer types by shrunken centroids of gene expression," *Proc. Natl. Acad. Sci. U.S.A.* 99, 6567-6572, 2002.
Tolstoshev, "Gene therapy, concepts, current trials and future directions," *Ann. Rev. Pharmacol. Toxicol.* 32:573-596, 1993.
Tusher et al., "Significance analysis of microarrays applied to the ionizing radiation response," *Proc. Natl. Acad. Sci. U.S.A.* 98(9):5116-21, 2001.
Veber and Freidinger, "The design of metabolically-stable peptide analogs," *Trends Neurosci.* 8:392, 1985.
Warnat et al., "Cross-platform analysis of cancer microarray data improves gene expression based classification of phenotypes," *BMC Bioinformatics* 6:265, 2005.
Wu and Wu, "Delivery systems for gene therapy," *Biotherapy* 3:87-95, 1991.
Zeger and Liang, "Longitudinal data analysis for discrete and continuous outcomes," *Biometrics* 42:121-130, 1986.
International Preliminary Report on Patentability and Written Opinion dated Jan. 10, 2006, for PCT/US2005/000564, filed on Jan. 7, 2005, published as WO 2005/068664, and entitled "Cell-Type-Specific Patterns of Gene Expression" (12 pages).
Carillo and Lipman, "The Multiple Sequence Alignment Problem in Biology," *Siam J. Appl. Math.*, 48(5):1073-1082 (1988).
Nair et al., "Rival penalized competitive learning (RPCL): a topology-determining algorithm for analyzing gene expression data," *Comput. Biol. Chem.*, 27(6): 565-574 (2003).
Pavlova et al., "Evolution of gene expression patterns in a model of branching morphogenesis," *M. J. Physiol.*, 277 (Renal Physiol. 46): F650-F653 (1999).
Prakash et al., "Symptomatic and asymptomatic benign prostatic hyperplasia: Molecular differentiation by using microarrays," *Proc. Natl. Acad. Sci. U.S.A.*, 99(11):7598-7603 (2002).
Stuart et al., "Changes in gene expression patterns in the ureteric bud and metanephric mesenchyme in models of kidney development," *Kidney Int.*, 64:1997-2008 (2003).
Stuart et al., "Changes in global gene expression patterns during development and maturation of the rat kidney," *Proc. Natl. Acad. Sci. U.S.A.*, 98(10):5649-5654 (2001).
Stuart et al., "In silico dissection of cell-type associated patterns of gene expression in prostate cancer," in *Proceedings of the American Association of Cancer Research*, 2003, vol. 44, abstract No. 3210.
Stuart, "Novel Approaches to DNA Array Data Analysis: Gene Expression Profiling in the Developing Rat Kidney [P-19]," Small Talk 2001, The microfluidics, microarrays and BioMEMS Conference and Exhibition, Final Conference Progam, San Diego, California, Aug. 27-31, 2001, p. 60.

\* cited by examiner

**Agreement Analysis of Pathologists' Percent Estimates
by Calculation of Pearson Correlation Coefficients**

CELL-TYPE-SPECIFIC PATTERNS OF GENE EXPRESSION

CROSS REFERENCE TO RELATED APPLICATIONS

This application claims priority under 35 U.S.C. §119 from Provisional Application Ser. No. 60/535,382, filed Jan. 9, 2004, and Provisional Application Ser. No. 60/536,163, filed Jan. 12, 2004. The disclosures of these applications are incorporated herein by reference.

STATEMENT AS TO FEDERALLY SPONSORED RESEARCH

This invention was made with government support under CA84998 awarded by National Institute of Health. The government has certain rights in the invention.

SEQUENCE LISTING

The instant application contains a Sequence Listing, which is submitted herewith via CD-R in lieu of a printed copy, and is hereby incorporated by reference in its entirety. Said CD-R, recorded on Aug. 9, 2006, are labeled CRF, "Copy 1" and "Copy 2", respectively, and each contains only one identical 297 MB file (15677301.APP).

ELECTRONIC FILE APPENDIX

Submitted herewith in computer readable form are table appendices and a sequence listing. The table appendices are contained in a compact disc, and are listed under the filenames "Table 2.txt" "Table 8.txt" "Table 15.txt" and "Table 16.txt", which were created Jan. 10, 2005, and are 863 kb, 426 kb, 510 kb, and 1,583 kb, respectively, in size. An electronic version on compact disc (CD-R) of a computer-readable form of the Sequence Listing and Tables is filed herewith in duplicate (labeled Copy 1 and Copy 2) along with a third CD-R, labeled computer-readable form. The computer-readable files on each of the aforementioned compact discs originally created on Jan. 10, 2005, and created for resubmission on Nov. 30, 2005, are identical. The Sequence Listing is 237,457 kilobytes in size and is entitled 15670-073SEQ001.txt. Table 2 is 863 kilobytes in size and entitled Table 2.txt. Table 8 is 426 kilobytes in size and entitled Table 8.txt. Table 15 is 510 kilobytes in size and entitled Table 15.txt. Table 16 is 1,583 kilobytes in size and entitled Table 16.txt. All subject matter of the table appendix and sequence listing files on compact disk is incorporated herein by reference.

TECHNICAL FIELD

This invention relates to methods for determining gene expression in cells.

BACKGROUND

Numerous diseases and disorders are the result of specific gene expression in a tissue. For example, prostate cancer is the most common malignancy in men and is the cause of considerable morbidity and mortality (Howe et al., J. Natl. Cancer Inst. 93, 824-842, 2001). There is therefore a major incentive to try to identify genes that could be reliable early diagnostic and prognostic markers and therapeutic targets for such diseases and disorders.

SUMMARY

The methods, compositions, combinations and kits provided herein employ a regression-based approach for identification of cell-type-specific patterns of gene expression in samples containing more than one type of cell. In one example, the methods, compositions, combinations and kits provided herein employ a regression-based approach for identification of cell-type-specific patterns of gene expression in cancer. These methods, compositions, combinations and kits provided herein can be used in the identification of genes that are differentially expressed in malignant versus non-malignant cells and further identify tumor-dependent changes in gene expression of non-malignant cells associated with malignant cells relative to non-malignant cells not associated with malignant cells. The methods, compositions, combinations and kits provided herein also can be used in correlating a phenotype with gene expression in one or more cell types.

Provided herein are methods, compositions, combinations and kits for determining gene expression levels in one or more cell types in heterogeneous cell samples. For example such a method can include determining the relative content of each cell type in two or more related heterogeneous cell samples, wherein at least two of the samples do not contain the same relative content of each cell type; measuring overall levels of one or more gene expression analytes in each sample; determining the regression relationship between the relative content of each cell type and the measured overall levels; and calculating the level of each of the one or more analytes in each cell type according to the regression relationship, wherein gene expression levels correspond to the calculated levels of analytes. For example such a method can include determining the relative content of each cell type in two or more related heterogeneous cell samples, wherein at least two of the samples do not contain the same relative content of each cell type; measuring overall levels of two or more gene expression analytes in each sample; determining the regression relationship between the relative content of each cell type and the measured overall levels; and calculating the level of each of the two or more analytes in each cell type according to the regression relationship, wherein gene expression levels correspond to the calculated levels of analytes. Such methods can further include identifying genes differentially expressed in at least one cell type relative to at least one other cell type. In such methods, the analyte can be selected from a nucleic acid molecule and a protein.

In another embodiment, methods, compositions, combinations and kits are provided for identifying genes differentially expressed in malignant cells relative to non-malignant cells. Such a method can include determining the relative content of each cell type in two or more cell samples of the same tissue or organ, wherein the two or more cell samples include at least a first sample containing malignant cells and a second sample that does not contain the same relative content of each cell type as the first sample; measuring overall expression levels of one or more genes in each sample; determining the regression relationship between the relative content of each cell type and the measured overall levels; calculating the level of each of the one or more genes in each cell type according to the regression relationship; and identifying genes differentially expressed in malignant cells relative to non-malignant cells. Such a method also can include determining the relative content of each cell type in two or more cell samples of the same tissue or organ, wherein the two or more cell samples include at least a first sample containing malignant cells and a second sample that does not contain the same relative content of each cell type as the first sample; measuring overall expression levels of two or more genes in each sample; determining the regression relationship between the relative content of each cell type and the measured overall levels; calculating the level of each of the two or more genes in each cell type according to the regression relationship; and identifying genes differentially expressed in malignant cells relative to non-malignant cells.

Also provided herein are methods, compositions, combinations and kits for characterizing one or more cell types in a subject. For example, such a method can include measuring expression levels of one or more genes in a heterogeneous cell sample from a subject; comparing the measured levels to a plurality of reference expression levels of the one or more genes, wherein the plurality of reference levels are indicative of two or more cell types; and if the measured levels match reference levels indicative of a specific cell type in the sample, identifying a subject as having the specific cell type. In another example, such a method can include measuring expression levels of two or more genes in a heterogeneous cell sample from a subject; comparing the measured levels to a plurality of reference expression levels of the two or more genes, wherein the plurality of reference levels are indicative of two or more cell types; and if the measured levels match reference levels indicative of a specific cell type in the sample, identifying a subject as having the specific cell type. In another embodiment, provided herein are methods, compositions, combinations and kits for characterizing one or more cell types in a subject, by measuring expression levels of one or more genes in a cell sample from a subject; comparing the measured levels to reference expression levels of the one or more genes, wherein the reference expression levels are determined according to the methods provided herein; and if the measured levels match reference levels indicative of a specific cell type in the sample, identifying a subject as having the specific cell type. In another embodiment, provided herein are methods, compositions, combinations and kits for characterizing one or more cell types in a subject, by measuring expression levels of two or more genes in a cell sample from a subject; comparing the measured levels to reference expression levels of the two or more genes, wherein the reference expression levels are determined according to the methods provided herein; and if the measured levels match reference levels indicative of a specific cell type in the sample, identifying a subject as having the specific cell type. In such methods, the specific cell type can be selected from the group consisting of malignant cell and non-malignant cell adjacent to a malignant cell in a subject. Also provided herein are methods for identifying a subject as having malignant cells, by measuring expression levels of one or more genes in a heterogeneous cell sample from a subject; comparing the measured levels to a plurality of reference expression levels of the one or more genes, wherein the plurality of reference levels are indicative of two or more cell types; and if the measured levels match reference levels indicative of in malignant cells in the sample or of non-malignant cells in the sample that had been adjacent to malignant cells in the subject, identifying a subject as having malignant cells. Also provided herein are methods for identifying a subject as having malignant cells, by measuring expression levels of two or more genes in a heterogeneous cell sample from a subject; comparing the measured levels to a plurality of reference expression levels of the two or more genes, wherein the plurality of reference levels are indicative of two or more cell types; and if the measured levels match reference levels indicative of in malignant cells in the sample or of non-malignant cells in the sample that had been adjacent to malignant cells in the subject, identifying a subject as having malignant cells. In another embodiment, provided herein are methods of identifying a subject as having malignant cells, by measuring expression levels of one or more genes in a cell sample from a subject; comparing the measured levels to reference expression levels of the one or more genes, wherein the reference expression levels are determined according to the methods provided herein; and if the measured levels match reference levels indicative of in malignant cells in the sample or of non-malignant cells in the sample that had been adjacent to malignant cells in the subject, identifying a subject as having malignant cells. In another embodiment, provided herein are methods of identifying a subject as having malignant cells, by measuring expression levels of two or more genes in a cell sample from a subject; comparing the measured levels to reference expression levels of the two or more genes, wherein the reference expression levels are determined according to the methods provided herein; and if the measured levels match reference levels indicative of in malignant cells in the sample or of non-malignant cells in the sample that had been adjacent to malignant cells in the subject, identifying a subject as having malignant cells. In another embodiment, provided herein are methods of identifying a subject as having malignant cells, by assaying a cell sample from a subject for non-malignant cells in the sample that had been adjacent to malignant cells in the subject; and if the malignant-cell-adjacent non-malignant cells are present in the sample, identifying a subject as having malignant cells. In such methods the malignant-cell-adjacent non-malignant cells can be stromal cells.

Also provided herein are methods, compositions, combinations and kits for determining gene expression levels in one or more cell types corresponding to two or more phenotypes. For example, such a method can include determining the relative content of each cell type in two or more related heterogeneous cell samples, wherein at least two of the samples do not contain the same relative content of each cell type, and wherein at least two of the samples correspond to different phenotypes; measuring overall levels of one or more gene expression analytes in each sample; determining the regression relationship between the relative content of each cell type for each phenotype and the measured overall levels; and calculating the level of each of the one or more analytes in each cell type for each phenotype according to the regression relationship, wherein gene expression levels in each cell type for each phenotype correspond to the calculated levels of analytes. In another example, such a method can include determining the relative content of each cell type in two or more related heterogeneous cell samples, wherein at least two of the samples do not contain the same relative content of each cell type, and wherein at least two of the samples correspond to different phenotypes; measuring overall levels of two or more gene expression analytes in each sample; determining the regression relationship between the relative content of each cell type for each phenotype and the measured overall levels; and calculating the level of each of the two or more analytes in each cell type for each phenotype according to the regression relationship, wherein gene expression levels in each cell type for each phenotype correspond to the calculated levels of analytes. Also provided herein are methods, compositions, combinations and kits for identifying a phenotype of a subject. For example, such a method can include measuring expression levels of one or more genes in a cell sample from a subject; comparing the measured levels to reference expression levels of the one or more genes, wherein the reference expression levels are determined according to methods provided herein; and if the measured levels match reference levels indicative of a specific phenotype, identifying a subject as having the specific phenotype. In another example, such a method can include measuring expression levels of two or more genes in a cell sample from a subject; comparing the measured levels to reference expression levels of the two or more genes, wherein the reference expression levels are determined according to methods provided herein; and if the measured levels match reference levels indicative of a specific phenotype, identifying a subject as having the specific phenotype. Also provided are methods wherein the phenotype can be indicative of prognosis of a disease or disorder.

Also provided herein are methods, compositions, combinations and kits for determining gene expression levels in one or more cell types indicative of a disease or disorder. For example, the method can include determining the relative content of each cell type in two or more related heterogeneous cell samples, wherein at least two of the samples do not contain the same relative content of each cell type, and wherein at least one sample is from a subject with a disease or disorder and at least one sample is from a subject without a disease or disorder; measuring overall levels of one or more gene expression analytes in each sample; determining the regression relationship between the relative content of each cell type for both disease and non-disease and the measured overall levels; and calculating the level of each of the one or more analytes in each cell type for both disease and non-disease according to the regression relationship, wherein gene expression levels in each cell type for both disease and non-disease correspond to the calculated levels of analytes. In another example, the method can include determining the relative content of each cell type in two or more related heterogeneous cell samples, wherein at least two of the samples do not contain the same relative content of each cell type, and wherein at least one sample is from a subject with a disease or disorder and at least one sample is from a subject without a disease or disorder; measuring overall levels of two or more gene expression analytes in each sample; determining the regression relationship between the relative content of each cell type for both disease and non-disease and the measured overall levels; and calculating the level of each of the two or more analytes in each cell type for both disease and non-disease according to the regression relationship, wherein gene expression levels in each cell type for both disease and non-disease correspond to the calculated levels of analytes. Also provided are methods of identifying a disease or disorder in a subject by measuring expression levels of one or more genes in a cell sample from a subject; comparing the measured levels to reference expression levels of the one or more genes, wherein the reference expression levels are determined according to methods provided herein; and if the measured levels match reference levels indicative of a specific disease or disorder, identifying a subject as having the specific disease or disorder. Also provided are methods of identifying a disease or disorder in a subject by measuring expression levels of two or more genes in a cell sample from a subject; comparing the measured levels to reference expression levels of the two or more genes, wherein the reference expression levels are determined according to methods provided herein; and if the measured levels match reference levels indicative of a specific disease or disorder, identifying a subject as having the specific disease or disorder. In methods that include determining disease prognosis, the prognosis can be tumor relapse, aggressiveness of tumor, indolence of tumor, survival, or likelihood of successful treatment of tumor. In some embodiments of the methods provided herein, the sample is clinically classified as negative of a tumor, and presence in the sample of non-malignant cells adjacent to malignant cells can be indicative of tumor, tumor relapse, aggressiveness of tumor, indolence of tumor, survival, or likelihood of successful treatment of tumor.

Also provided herein are methods, compositions, combinations and kits for identifying environment-dependent changes in gene expression of a cell type. For example, such a method can include determining the relative content of each cell type in two or more related heterogeneous cell samples, wherein at least two of the samples do not contain the same relative content of each cell type, and wherein cells of the same type that are in different cell environments are separately classified; measuring overall levels of one or more gene expression analytes in each sample; determining the regression relationship between the relative content of each cell classification and the measured overall levels; calculating the level of each of the one or more analytes in each cell classification according to the regression relationship; and identifying genes differentially expressed in separately classified cells of the same type, thereby identifying environment-dependent changes in gene expression of a cell type. In another example, such a method can include determining the relative content of each cell type in two or more related heterogeneous cell samples, wherein at least two of the samples do not contain the same relative content of each cell type, and wherein cells of the same type that are in different cell environments are separately classified; measuring overall levels of two or more gene expression analytes in each sample; determining the regression relationship between the relative content of each cell classification and the measured overall levels; calculating the level of each of the two or more analytes in each cell classification according to the regression relationship; and identifying genes differentially expressed in separately classified cells of the same type, thereby identifying environment-dependent changes in gene expression of a cell type. Another method of identifying tumor-dependent changes in gene expression of a cell type includes determining the relative content of each cell type in two or more related heterogeneous cell samples, wherein at least two of the samples do not contain the same relative content of each cell type, and wherein cells associated with tumor are classified separately from cells of the same type that are not associated with tumor; measuring overall levels of one or more gene expression analytes in each sample; determining the regression relationship between the relative content of each cell classification and the measured overall levels; calculating the level of each of the one or more analytes in each cell classification according to the regression relationship; and identifying genes differentially expressed in cells associated with tumor relative to cells of the same type that are not associated with tumor. Another method of identifying tumor-dependent changes in gene expression of a cell type includes determining the relative content of each cell type in two or more related heterogeneous cell samples, wherein at least two of the samples do not contain the same relative content of each cell type, and wherein cells associated with tumor are classified separately from cells of the same type that are not associated with tumor; measuring overall levels of two or more gene expression analytes in each sample; determining the regression relationship between the relative content of each cell classification and the measured overall levels; calculating the level of each of the two or more analytes in each cell classification according to the regression relationship; and identifying genes differentially expressed in cells associated with tumor relative to cells of the same type that are not associated with tumor.

Also provided herein are methods, compositions, combinations and kits for identifying a phenotype of a subject. For example, a method can include measuring expression levels of one or more genes in a heterogeneous cell sample from a subject; comparing the measured levels to reference expression levels of the one or more genes, wherein the plurality of reference levels are indicative of two or more phenotypes; and if the measured levels match reference levels indicative of a specific phenotype, identifying a subject as having the specific phenotype. In another example, a method can include measuring expression levels of two or more genes in a heterogeneous cell sample from a subject; comparing the measured levels to reference expression levels of the two or more genes, wherein the plurality of reference levels are indicative of two or more phenotypes; and if the measured levels match reference levels indicative of a specific phenotype, identifying a subject as having the specific phenotype.

In the methods provided herein, all steps can be performed without physically separating the cells in the sample. Further in the methods provided herein, the step of determining the regression relationship can include determining the regression of overall levels of each analyte on the cell proportions.

Also provided herein are methods, compositions, combinations and kits for classifying a cell sample as indicative of prostate cancer or not indicative of prostate cancer. For example, a method can include detecting the expression levels of genes relative to a reference, the genes comprising at least 2 different indicating genes, wherein each indicating gene comprises either: (a) a nucleotide sequence at least 90% identical to a nucleotide sequence selected from SEQ ID NO:1-38,826 or a complement thereof or (b) a nucleotide sequence that hybridizes under high stringency to a nucleotide sequence selected from SEQ ID NO:1-38,826 or a complement thereof. In another embodiment, provided herein are methods, compositions, combinations and kits for classifying a cell sample as indicative of prostate cancer or not indicative of prostate cancer. In another embodiment, provided is a use of a combination for the preparation of a composition for classifying a sample as indicative of prostate cancer or not indicative of prostate cancer, wherein the combination detects the expression levels of genes relative to a reference, the genes comprising at least 2 different indicating genes, wherein each indicating gene comprises either: (a) a nucleotide sequence at least 90% identical to a nucleotide sequence selected from SEQ ID NO:1-38,826 or a complement thereof or (b) a nucleotide sequence that hybridizes under high stringency to a nucleotide sequence selected from SEQ ID NO:1-38,826 or a complement thereof. In some embodiments, the nucleotide sequences selected from SEQ ID NO:1-38,826 are selected from SEQ ID NO:35,580-38, 826.

The methods, compositions, combinations, uses and kits provided herein can be used to detect the expression levels of genes relative to a reference, the genes comprising at least 5, 10, 15, 20, 30, 40, 50, 75, 100, 150, 200, 300, 400, 500, 750, 1,000, 1,250, 1,500, 1,750, 2,000, 2,250, 2,500, or 2750 indicating genes.

Also provided herein are microarrays wherein at least 50%, 70%, 80%, 90%, 95%, 97%, 98% or 99% of the loci of the array specifically detect the expression level of the 2 or more indicating genes of the methods, compositions, combinations, uses and kits provided herein.

Also provided herein are methods, compositions, combinations, uses and kits for treating prostate cancer. For example, a method can include modulating the activity of a gene product selected from the group consisting of: (a) a product of a gene comprising a nucleotide sequence at least 90% identical to a nucleotide sequence selected from SEQ ID NO:1-38,826 or a complement thereof or (b) a gene product complementary to a nucleotide sequence that hybridizes under high stringency to a nucleotide sequence selected from SEQ ID NO:1-38,826 or a complement thereof. In some embodiments, the nucleotide sequences selected from SEQ ID NO:1-38,826 are selected from SEQ ID NO:35,580-38, 826. In the methods, compositions, combinations, uses and kits provided herein, the compound can be selected from the group consisting of an antibody, an antisense compound, a ribozyme, a DNAzyme, an RNA interference compound, a small molecule, a heterologous nucleic acid molecule encoding the gene, the gene product, and any combination thereof. For example, the modulating compound can specifically bind to mRNA encoding the gene or the protein gene product and thereby inhibit expression of the gene. In other methods, compositions, combinations, uses and kits provided herein, the modulating step can further include administering to a subject with prostate cancer a compound that increases the activity of the gene product selected from the selected from the group consisting of heterologous nucleic acid molecule encoding the gene, the gene product, and a combination thereof. For example the heterologous nucleic acid molecule can be an expression vector.

Also provided herein are methods, compositions, combinations, uses and kits for screening compounds. For example, a method can include contacting with a test compound a cell expressing a gene selected from the group consisting of: (a) a gene comprising a nucleotide sequence selected from SEQ ID NO:1-38,826 or a complement thereof; and (b) a gene comprising a nucleotide sequence that hybridizes under high stringency to a nucleotide sequence selected from SEQ ID NO:1-38,826 or a complement thereof, and measuring expression levels of the gene, wherein a change in expression levels relative to a reference identifies the compound as a compound that modulates a expression of the gene. Another screening method includes contacting with a test compound a gene product selected from the group consisting of: a product of a gene comprising a nucleotide sequence at least 90% identical to a nucleotide sequence selected from SEQ ID NO:1-38,826 or a complement thereof or (b) a gene product complementary to a nucleotide sequence that hybridizes under high stringency to a nucleotide sequence selected from SEQ ID NO:1-38,826 or a complement thereof, and either: (i) identifying a test compound that specifically binds to the gene product, or (ii) identifying a test compound that inhibits binding of a compound known to bind the gene product. In some embodiments, the nucleotide sequences selected from SEQ ID NO:1-38,826 are selected from SEQ ID NO:35,580-38, 826.

In some of the methods, compositions, combinations, uses and kits provided herein at least one of the gene products corresponds to a Probe or Identifer/LocusLink with a modified t statistic in tumor >2.5 or ←−2.5. In others, at least one of the gene products corresponds to a Probe or Identifer/LocusLink with a modified t statistic in benign prostatic hypertrophy (BPH) >2.5 or ←−2.5. In others, at least one of the gene products corresponds to a Probe or Identifer/LocusLink with a modified t statistic in stroma >2.5 or ←−2.5. In some of the methods, compositions, combinations, uses and kits provided herein the gene product can be selected from the group consisting of: (a) a product of a gene comprising a nucleotide sequence at least 90% identical to the nucleotide sequence of a Probe identified in Table 9 as having a modified t statistic in tumor >2.5 or ←−2.5; (b) a product of a gene comprising a nucleotide sequence at least 90% identical to the nucleotide sequence of a gene encoded by an Identifier and LocusLink identified in Table 9 as having a modified t statistic in tumor >2.5 or ←−2.5; (c) a product of a gene comprising a nucleotide sequence at least 90% identical to the nucleotide sequence of a Probe identified in Table 10 as having a modified t statistic in stroma >2.5 or ←−2.5; and (d) a product of a gene comprising a nucleotide sequence at least 90% identical to the nucleotide sequence of a gene encoded by an Identifier and LocusLink identified in Table 10 as having a modified t statistic in stroma >2.5 or ←−2.5. In some of the methods, compositions, combinations, uses and kits provided herein, the modified t statistic can be >3 or ←−3, >3.5 or ←−3.5, >4 or ←−4, >4.5 or ←−4.5, or >5 or ←−5.

Also provided herein are compounds that modulate the activity of a gene product selected from the group consisting of: (a) a product of a gene comprising a nucleotide sequence at least 90% identical to a nucleotide sequence selected from SEQ ID NO:1-38,826 or a complement thereof or (b) a gene product complementary to a nucleotide sequence that hybridizes under high stringency to a nucleotide sequence selected from SEQ ID NO:1-38,826 or a complement thereof. In some embodiments, the nucleotide sequences selected from SEQ ID NO:1-38,826 are selected from SEQ ID NO:35,580-38,826. In certain embodiments, such a compound can be selected from the group consisting of an antibody, an antisense compound, a ribozyme, a DNAzyme, an RNA interference compound, a small molecule, a heterologous nucleic acid molecule encoding the gene, the gene product, and any combination thereof. Some compounds provided herein are present in pharmaceutically acceptable form.

Also provided herein are compounds that indicates the presence of a gene product selected from the group consisting of: (a) a product of a gene comprising a nucleotide sequence at least 90% identical to a nucleotide sequence selected from SEQ ID NO:1-38,826 or a complement thereof or (b) a gene product complementary to a nucleotide sequence that hybridizes under high stringency to a nucleotide sequence selected from SEQ ID NO:1-38,826 or a complement thereof. In some embodiments, the nucleotide sequences selected from SEQ ID NO:1-38,826 are selected from SEQ ID NO:35,580-38, 826. In certain embodiments, such a compound can be selected from the group consisting of a nucleic acid molecule that specifically binds at least 10 nucleotides in the gene or a complement thereof or a fragment thereof, an antibody that specifically binds the gene or a complement thereof, and an antibody that specifically binds the gene product or a fragment thereof.

Also provided herein are combinations of one or more of the compounds provided herein, or combinations of at least at least 2, 3, 4, 5, 6, 7, 8, 9, 10, 15 or 20 compounds provided herein.

Also provided herein are diagnostic markers for prostate cancer as set forth in SEQ ID NO:1-38,826. Also provided herein are kits comprising nucleic acids, polypeptides and/or antibodies useful in detecting the markers set forth in SEQ ID NO:1-38,826 for detecting prostate cancer. Also provided herein are methods of treating or preventing prostate cancer comprising suppressing gene expression or inhibiting or neutralizing the gene product of the genes that are listed as tumor markers and that are differentially expressed in the Tables provided herein and SEQ ID NO:1-38,826. In some such methods antibodies, antisense, ribozyme, a DNAzyme, RNA interference, and/or small molecule therapy to neutralize the gene or gene products, can be used. Also provided herein are prognostic markers for early relapse in prostate cancer as set forth in SEQ ID NO:1-38,826, complements thereof, fragments thereof, and polypeptides encoded thereby. Also provided herein are kits comprising nucleic acids, polypeptides and/or antibodies useful in detecting the markers set forth in SEQ ID NO:1-38,826, complements thereof, fragments thereof, and polypeptides encoded thereby for detecting early relapse of prostate cancer. In some embodiments, the nucleotide sequences selected from SEQ ID NO:1-38,826 are selected from SEQ ID NO:35,580-38,826. Also provided herein are methods of treating or preventing prostate cancer comprising suppressing gene expression or inhibiting or neutralizing the gene product of genes that are up-regulated in the tumor epithelial cells of early relapsed prostate cancer samples, wherein such genes have a T>3 in Table 8, Table 9, Table 10, Table 12 or Table 13. In some such methods antibodies, antisense, ribozyme, a DNAzyme, RNA interference, and/or small molecule therapy to neutralize the gene or gene products, can be used. Also provided herein are computer implemented methods.

The details of the methods, compositions, combinations and kits provided herein, are set forth in the accompanying drawings and the description below. Other features, objects, and advantages of the invention will be apparent from the description and drawings, and from the claims.

DETAILED DESCRIPTION

Definitions

Figure 1:
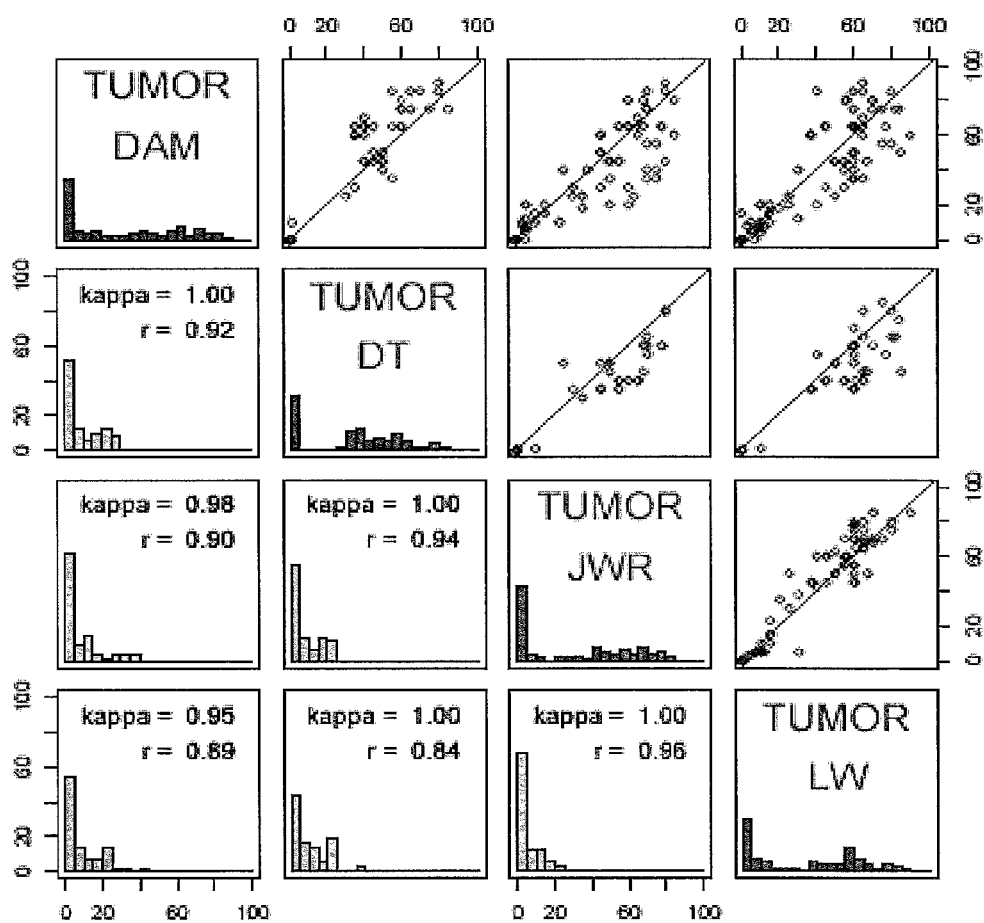
FIG. 1 depicts graphs showing agreement analysis of pathologists' percent estimates by calculation of Pearson correlation coefficients. The figure shows agreement among four pathologists, for the analysis of prostate cancer sections. A total of 363 rankings were analyzed. For any graph, the y- and x-axes give the percent of a given tissue section estimated to be tumor epithelial cells by rater whose initials occur in the diagonal panels found by moving horizontally and vertically respectively. The histograms below the diagonal show few instances in which $y_{ij1kj}$-$y_{ij2kj}$ exceeds 20%, and usually it is <5%. Further, the k statistics and the Pearson correlations coefficients are all high. Many of the ratings showed <5% tumor cells (histograms on diagonal), making this a good test for presence versus absence of tumor cells.

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

Differential expression, as used herein, refers to both quantitative as well as qualitative differences in the extend of the genes' expression depending on differential development and/or tumor growth. Differentially expressed genes can represent marker genes, and/or target genes. The expression pattern of a differentially expressed gene disclosed herein can be utilized as part of a prognostic or diagnostic evaluation of a subject. The expression pattern of a differentially expressed gene can be used to identify the presence of a particular cell type in a sample. A differentially expressed gene disclosed herein can be used in methods for identifying reagents and compounds and uses of these reagents and compounds for the treatment of a subject as well as methods of treatment.

Biological activity or bioactivity or activity or biological function, which are used interchangeably, herein mean an effector or antigenic function that is directly or indirectly performed by a polypeptide (whether in its native or denatured conformation), or by any fragment thereof in vivo or in vitro. Biological activities include but are not limited to binding to polypeptides, binding to other proteins or molecules, enzymatic activity, signal transduction, activity as a DNA binding protein, as a transcription regulator, ability to bind damaged DNA, etc. A bioactivity can be modulated by directly affecting the subject polypeptide. Alternatively, a bioactivity can be altered by modulating the level of the polypeptide, such as by modulating expression of the corresponding gene.

The term gene expression analyte refers a biological molecule, e.g., a nucleic acid, peptide, hormone, etc., whose presence or concentration can be detected and correlated with gene expression.

As used herein, gene expression levels refers to the amount of biological macromolecule produced from a gene. For example, expression levels of a particular gene can refer to the amount of protein produced from that particular gene, or can refer to the amount of mRNA produced from that particular gene. Gene expression levels can refer to an absolute (e.g., molar or gram-quantity) levels or relative (e.g., the amount relative to a standard, reference, calibration, or to another gene expression level). Typically, gene expression levels used herein are relative expression levels. As used herein in regard to determining the relationship between cell content and expression levels, gene expression levels can be considered in terms of any manner of describing gene expression known in the art. For example, regression methods that consider gene expression levels can consider the measurement of the level of a gene expression analyte, or the level calculated or estimated according to the measurement of the level of a gene expression analyte.

Marker gene, as used herein, refers to a differentially expressed gene which expression pattern can serve as part of a phenotype-indicating method, such as a predictive method, prognostic or diagnostic method, or other cell-type distinguishing evaluation, or which, alternatively, can be used in methods for identifying compounds useful for the treatment or prevention of diseases or disorders, or for identifying compounds that modulate the activity of one or more gene products.

As used herein, a phenotype indicated by methods provided herein can be a diagnostic indication, a prognostic indication, or an indication of the presence of a particular cell type in a subject. Diagnostic indications include indication of a disease or a disorder in the subject, such as presence of tumor or neoplastic disease, inflammatory disease, autoimmune disease, and any other diseases known in the art that can be identified according to the presence or absence of particular cells or by the gene expression of cells. In another embodiment, prognostic indications refers to the likely or expected outcome of a disease or disorder, including, but not limited to, the likelihood of survival of the subject, likelihood of relapse, aggressiveness of the disease or disorder, indolence of the disease or disorder, and likelihood of success of a particular treatment regimen.

As used herein, a gene expression analyte refers to a biological molecule that indicates the expression of a particular gene. For example, a gene expression analyte can be a mRNA of a particular gene, or a fragment thereof (including, e.g., by-products of mRNA splicing and nucleolytic cleavage fragments), a protein of a particular gene or a fragment thereof (including, e.g., post-translationally modified proteins or by-products therefrom, and proteolytic fragments), and other biological molecules such as a carbohydrate, lipid or small molecule, whose presence or absence corresponds to the expression of a particular gene.

As used herein, gene expression levels that correspond to levels of gene expression analytes refers to the relationship between an analyte that indicates the expression of a gene, and the actual level of expression of the gene. Typically the level of a gene expression analyte is measured in experimental methods used to determine gene expression levels. As understood by one skilled in the art, the measured gene expression levels can represent gene expression at a variety of levels of detail (e.g., the absolute amount of a gene expressed, the relative amount of gene expressed, or an indication of increased or decreased levels of expression). The level of detail at which the levels of gene expression analytes can indicate levels of gene expression can be based on a variety of factors that include the number of controls used, the number of calibration experiments or reference levels determined, and other factors known in the art. In some methods provided herein, increase in the levels of a gene expression analyte can indicate increase in the levels of the gene expressed, and a decrease in the levels of a gene expression analyte can indicate decrease in the levels of the gene expressed.

As used herein, a regression relationship between relative content of a cell type and measured overall levels of a gene expression analyte refers to a quantitative relationship between cell type and level of gene expression analyte that is determined according to the methods provided herein based on the amount of cell type present in two or more samples and experimentally measured levels of gene expression analyte. In one embodiment, the regression relationship is determined by determining the regression of overall levels of each gene expression analyte on determined cell proportions. In one embodiment, the regression relationship is determined by linear regression, where the overall expression level or the expression analyte levle is treated as directly proportional to (e.g., linear in) cell percent either for each cell type in turn or all at once and the slopes of these linear relationships can be expressed as beta values.

As used herein, a heterogeneous sample refers to a sample that contains more than one cell type. For example, a heterogeneous sample can contain stromal cells and tumor cells. Typically, as used herein, the different cell types present in a sample are present in greater than about 0.1%, 0.2%, 0.3%, 0.5%, 0.7%, 1%, 2%, 3%, 4% or 5% or greater than 0.1%, 0.2%, 0.3%, 0.5%, 0.7%, 1%, 2%, 3%, 4% or 5%. As is understood in the art, cell samples, such as tissue samples from a subject, can contain minute amounts of a variety of cell types (e.g., nerve, blood, vascular cells). However, cell types that are not present in the sample in amounts greater than about 0.1%, 0.2%, 0.3%, 0.5%, 0.7%, 1%, 2%, 3%, 4% or 5% or greater than 0.1%, 0.2%, 0.3%, 0.5%, 0.7%, 1%, 2%, 3%, 4% or 5%, are not typically considered components of the heterogeneous cell sample, as used herein.

As used herein, related cell samples refers to samples that contain one or more cell types in common. Related cell samples can be samples from the same tissue type or from the same organ. Related cell samples can be from the same or different sources (e.g., same or different individuals or cell cultures, or a combination thereof). As provided herein, in the case of three or more different cell samples, it is not required that all samples contain a common cell type, but if a first sample does not contain any cell types that are present in the other samples, the first sample is not related to the other samples.

As used herein, tumor cells refers to cells with cytological and adherence properties consisting of nuclear and cyoplasmic features and patterns of cell-to-cell association that are known to pathologists skilled in the art as sufficient for the diagnosis as cancers of various types. In some embodiments, tumor cells have abnormal growth properties, such as neoplastic growth properties.

As used herein, cells associated with tumor refers to cells that, while not necessarily malignant, are present in tumorous tissues or organs or particular locations of tissues or organs, and are not present, or are present at insignificant levels, in normal tissues or organs, or in particular locations of tissues or organs.

As used herein, benign prostatic hyperplastic (BPH) cells refers to the cells of the epithelial lining of hyperplastic prostate glands.

As used herein, dilated cystic glands cells refers to the cells of the epithelial lining of dilated (atrophic) cystic prostate glands.

As used herein, stromal cells refers to the combined connective tissue cells and smooth muscle cells forming the stroma of an organ. Exemplary stromal cells are cells of the stroma of the prostate gland.

As used herein, a reference refers to a value or set of related values for one or more variables. In one example, a reference gene expression level refers to a gene expression level in a particular cell type. Reference expression levels can be determined according to the methods provided herein, or by determining gene expression levels of a cell type in a homogenous sample. Reference levels can be in absolute or relative amounts, as is known in the art. In certain embodiments, a reference expression level can be indicative of the presence of a particular cell type. For example, in certain embodiments, only one particular cell type may have high levels of expression of a particular gene, and, thus, observation of a cell type with high measured expression levels can match expression levels of that particular cell type, and thereby indicate the presence of that particular cell type in the sample. In another embodiment, a reference expression level can be indicative of the absence of a particular cell type. As provided herein, two or more references can be considered in determining whether or not a particular cell type is present in a sample, and also can be considered in determining the relative amount of a particular cell type that is present in the sample.

As used herein, a modified t statistic is a numerical representation of the ability of a particular gene product or indicator thereof to indicate the presence or absence of a particular cell type in a sample. A modified t statistic incorporating goodness of fit and effect size can be formulated according to known methods (see, e.g., Tusher (Proc. Natl. Acad. Sci. USA 98, 5116-5121, 2001)), where $\sigma\beta$ is the standard error of the coefficient, and k is a small constant, as follows:

$$t=\beta/(k+\sigma\beta)$$

As used herein, relative content of a cell type or cell proportion refers to the amount of a cell mixture that is populated by a particular cell type. Typically, heterogeneous cell mixtures contain two or more cell types, and, therefore, no single cell type makes up 100% of the mixture. Relative content can be expressed in any of a variety of forms known in the art; For example, relative content can be expressed as a percentage of the total amount of cells in a mixture, or can be expressed relative to the amount of a particular cell type. As used herein, percent cell or percent cell composition is the percent of all cells that a particular cell type accounts for in a heterologous cell mixture, such as a microscopic section sampling a tissue.

By array or matrix is meant an arrangement of addressable locations or addresses on a device. The locations can be arranged in two dimensional arrays, three dimensional arrays, or other matrix formats. The number of locations can range from several to at least hundreds of thousands. Most importantly, each location represents a totally independent reaction site. Arrays include but are not limited to nucleic acid arrays, protein arrays and antibody arrays. A nucleic acid array refers to an array containing nucleic acid probes, such as oligonucleotides, polynucleotides or larger portions of genes. The nucleic acid on the array can be single stranded. Arrays wherein the probes are oligonucleotides are referred to as oligonucleotide arrays or oligonucleotide chips. A microarray, herein also refers to a biochip or biological chip, an array of regions having a density of discrete regions of at least about 100/cm2, and can be at least about 1000/cm2. The regions in a microarray have typical dimensions, e.g., diameters, in the range of between about 10-250 μm, and are separated from other regions in the array by about the same distance. A protein array refers to an array containing polypeptide probes or protein probes which can be in native form or denatured. An antibody array refers to an array containing antibodies which include but are not limited to monoclonal antibodies (e.g. from a mouse), chimeric antibodies, humanized antibodies or phage antibodies and single chain antibodies as well as fragments from antibodies.

The term agonist, as used herein, is meant to refer to an agent that mimics or upregulates (e.g., potentiates or supplements) the bioactivity of a protein. An agonist can be a wild-type protein or derivative thereof having at least one bioactivity of the wild-type protein. An agonist can also be a compound that upregulates expression of a gene or which increases at least one bioactivity of a protein. An agonist can also be a compound which increases the interaction of a polypeptide with another molecule, e.g., a target peptide or nucleic acid.

As used herein a polynucleotide or nucleic acid molecule is a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, caps, substitution of one or more of the naturally occurring nucleotides with an analog, internucleotide modifications such as, for example, those with uncharged linkages (e.g., phosphorothioates, phosphorodithioates, etc.), those containing pendant moieties, such as, for example proteins (including e.g., nucleases, toxins, antibodies, signal peptides, poly-L-lysine, etc.),those with intercalators (e.g., acridine, psoralen, etc.), those containing chelators (e.g., metals, radioactive metals, etc.), those containing alkylators, those with modified linkages (e.g., alpha anomeric nucleic acids, etc.), those containing nucleotide analogs (e.g., peptide nucleic acids), as well as unmodified forms of the polynucleotide.

As used herein, a polynucleotide derived from a designated sequence refers to a polynucleotide sequence which is comprised of a sequence of approximately at least about 6 nucleotides, at least about 8 nucleotides, at least about 10-12 nucleotides, or at least about 15-20 nucleotides corresponding to a region of the designated nucleotide sequence. Corresponding polynucleotides are homologous to or complementary to a designated sequence. Typically, the sequence of the region from which the polynucleotide is derived is homologous to or complementary to a sequence that is unique to a gene provided herein.

A recombinant protein is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, constituting at least about 0.5%, or at least about 5% by weight of the total protein in a given sample. A substantially pure protein comprises at least about 50-75% by weight of the total protein, at least about 80%, or at least about 90%. The definition includes the production of a protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

As used herein, disease or disorder refers to a pathological condition in an organism resulting from, e.g., infection or genetic defect, and characterized by identifiable symptoms.

Whether any two nucleic acid molecules have nucleotide sequences that are at least, for example, 80%, 85%, 90%, 95%, 96%, 97%, 98% or 99% identical can be determined using known computer algorithms such as the FAST A program, using for example, the default parameters as in Pearson et al. (1988) Proc. Natl. Acad. Sci. USA 85:2444 (other programs include the GCG program package (Devereux, J., et al., Nucleic Acids Research 12(I):387 (1984)), BLASTP, BLASTN, FASTA (Atschul, S. F., et al., J Molec Biol 215:403 (1990); Guide to Huge Computers, Martin J. Bishop, ed., Academic Press, San Diego, 1994, and Carillo et al. (1988) SIAM J Applied Math 48:1073). For example, the BLAST function of the National Center for Biotechnology Information database can be used to determine identity. Other commercially or publicly available programs include, DNAStar MegAlign program (Madison, Wis.) and the University of Wisconsin Genetics Computer Group (UWG) Gap program (Madison Wis.)). Percent homology or identity of proteins and/or nucleic acid molecules can be determined, for example, by comparing sequence information using a GAP computer program (e.g., Needleman et al. (1970) J. Mol. Biol. 48:443, as revised by Smith and Waterman ((1981) Adv. Appl. Math. 2:482). Briefly, the GAP program defines similarity as the number of aligned symbols (i.e., nucleotides or amino acids) which are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov et al. (1986) Nucl. Acids Res. 14:6745, as described by Schwartz and Dayhoff, eds., ATLAS OF PROTEIN SEQUENCE AND STRUCTURE, National Biomedical Research Foundation, pp. 353-358 (1979); (2) a penalty of 3.0 for each gap and an additional 0.10 penalty for each symbol in each gap; and (3) no penalty for end gaps. Therefore, as used herein, the term identity represents a comparison between a test and a reference polypeptide or polynucleotide.

As used herein, the term at least 90% identical to refers to percent identities from 90 to 100 relative to the reference polypeptides. Identity at a level of 90% or more is indicative of the fact that, assuming for exemplification purposes a test and reference polynucleotide length of 100 amino acids are compared. No more than 10% (i.e., 10 out of 100) amino acids in the test polypeptide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g. 10/100 amino acid difference (approximately 90% identity). Differences are defined as nucleic acid or amino acid substitutions, or deletions. At the level of homologies or identities above about 85-90%, the result should be independent of the program and gap parameters set; such high levels of identity can be assessed readily, often without relying on software.

As used herein, primer refers to an oligonucleotide containing two or more deoxyribonucleotides or ribonucleotides, typically more than three, from which synthesis of a primer extension product can be initiated. Experimental conditions conducive to synthesis include the presence of nucleoside triphosphates and an agent for polymerization and extension, such as DNA polymerase, and a suitable buffer, temperature and pH.

As used herein, animals include any animal, such as, but are not limited to, goats, cows, deer, sheep, rodents, pigs and humans. Non-human animals, exclude humans as the contemplated animal. The SPs provided herein are from any source, animal, plant, prokaryotic and fungal.

As used herein, genetic therapy involves the transfer of heterologous nucleic acid, such as DNA, into certain cells, target cells, of a mammal, particularly a human, with a disorder or conditions for which such therapy is sought. The nucleic acid, such as DNA, is introduced into the selected target cells in a manner such that the heterologous nucleic acid, such as DNA, is expressed and a therapeutic product encoded thereby is produced. Alternatively, the heterologous nucleic acid, such as DNA, can in some manner mediate expression of DNA that encodes the therapeutic product, or it can encode a product, such as a peptide or RNA that in some manner mediates, directly or indirectly, expression of a therapeutic product. Genetic therapy can also be used to deliver nucleic acid encoding a gene product that replaces a defective gene or supplements a gene product produced by the mammal or the cell in which it is introduced. The introduced nucleic acid can encode a therapeutic compound, such as a growth factor inhibitor thereof, or a tumor necrosis factor or inhibitor thereof, such as a receptor therefor, that is not normally produced in the mammalian host or that is not produced in therapeutically effective amounts or at a therapeutically useful time. The heterologous nucleic acid, such as DNA, encoding the therapeutic product can be modified prior to introduction into the cells of the afflicted host in order to enhance or otherwise alter the product or expression thereof. Genetic therapy can also involve delivery of an inhibitor or repressor or other modulator of gene expression.

As used herein, heterologous nucleic acid is nucleic acid that encodes RNA or RNA and proteins that are not normally produced in vivo by the cell in which it is expressed or that mediates or encodes mediators that alter expression of endogenous nucleic acid, such as DNA, by affecting transcription, translation, or other regulatable biochemical processes. Heterologous nucleic acid, such as DNA, can also be referred to as foreign nucleic acid, such as DNA. Any nucleic acid, such as DNA, that one of skill in the art would recognize or consider as heterologous or foreign to the cell in which is expressed is herein encompassed by heterologous nucleic acid; heterologous nucleic acid includes exogenously added nucleic acid that is also expressed endogenously. Examples of heterologous nucleic acid include, but are not limited to, nucleic acid that encodes traceable marker proteins, such as a protein that confers drug resistance, nucleic acid that encodes therapeutically effective substances, such as anti-cancer agents, enzymes and hormones, and nucleic acid, such as DNA, that encodes other types of proteins, such as antibodies. Antibodies that are encoded by heterologous nucleic acid can be secreted or expressed on the surface of the cell in which the heterologous nucleic acid has been introduced. Heterologous nucleic acid is generally not endogenous to the cell into which it is introduced, but has been obtained from another cell or prepared synthetically. Generally, although not necessarily, such nucleic acid encodes RNA and proteins that are not normally produced by the cell in which it is now expressed.

As used herein, a therapeutically effective product for gene therapy is a product that is encoded by heterologous nucleic acid, typically DNA, that, upon introduction of the nucleic acid into a host, a product is expressed that ameliorates or eliminates the symptoms, manifestations of an inherited or acquired disease or that cures the disease. Also included are biologically active nucleic acid molecules, such as RNAi and antisense.

As used herein, disease or disorder treatment or compound refers to any therapeutic regimen and/or agent that, when used alone or in combination with other treatments or compounds, can alleviate, reduce, ameliorate, prevent, or place or maintain in a state of remission of clinical symptoms or diagnostic markers associated with the disease or disorder.

As used herein, nucleic acids include DNA, RNA and analogs thereof, including peptide nucleic acids (PNA) and mixtures thereof. Nucleic acids can be single or double-stranded. When referring to probes or primers, optionally labeled, with a detectable label, such as a fluorescent or radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous of sequence complementary to or identical a gene of interest. Probes and primers can be 10, 20, 30, 50, 100 or more nucleic acids long.

As used herein, operative linkage of heterologous nucleic acids to regulatory and effector sequences of nucleotides, such as promoters, enhancers, transcriptional and translational stop sites, and other signal sequences refers to the relationship between such nucleic acid, such as DNA, and such sequences of nucleotides. Thus, operatively linked or operationally associated refers to the functional relationship of nucleic acid, such as DNA, with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it can be necessary to remove, add or alter 5' untranslated portions of the clones to eliminate extra, potential inappropriate alternative translation initiation (i.e., start) codons or other sequences that can interfere with or reduce expression, either at the level of transcription or translation. Alternatively, consensus ribosome binding sites (see, e.g., Kozak J. Biol. Chem. 266:19867-19870 (1991)) can be inserted immediately 5' of the start codon and can enhance expression. The desirability of (or need for) such modification can be empirically determined.

As used herein, a sequence complementary to at least a portion of an RNA, with reference to antisense oligonucleotides, means a sequence having sufficient complementarity to be able to hybridize with the RNA, generally under moderate or high stringency conditions, forming a stable duplex; in the case of double-stranded antisense nucleic acids, a single strand of the duplex DNA (or dsRNA) can thus be tested, or triplex formation can be assayed. The ability to hybridize depends on the degree of complementarily and the length of the antisense nucleic acid. Generally, the longer the hybridizing nucleic acid, the more base mismatches with a gene encoding RNA it can contain and still form a stable duplex (or triplex, as the case can be). One skilled in the art can ascertain a tolerable degree of mismatch by use of standard procedures to determine the melting point of the hybridized complex.

As used herein, antisense polynucleotides refer to synthetic sequences of nucleotide bases complementary to mRNA or the sense strand of double-stranded DNA. Admixture of sense and antisense polynucleotides under appropriate conditions leads to the binding of the two molecules, or hybridization. When these polynucleotides bind to (hybridize with) mRNA, inhibition of protein synthesis (translation) occurs. When these polynucleotides bind to double-stranded DNA, inhibition of RNA synthesis (transcription) occurs. The resulting inhibition of translation and/or transcription leads to an inhibition of the synthesis of the protein encoded by the sense strand. Antisense nucleic acid molecules typically contain a sufficient number of nucleotides to specifically bind to a target nucleic acid, generally at least 5 contiguous nucleotides, often at least 14 or 16 or 30 contiguous nucleotides or modified nucleotides complementary to the coding portion of a nucleic acid molecule that encodes a gene of interest.

As used herein, antibody refers to an immunoglobulin, whether natural or partially or wholly synthetically produced, including any derivative thereof that retains the specific binding ability the antibody. Hence antibody includes any protein having a binding domain that is homologous or substantially homologous to an immunoglobulin binding domain. Antibodies include members of any immunoglobulin groups, including, but not limited to, IgG, IgM, IgA, IgD, IgY and IgE.

As used herein, antibody fragment refers to any derivative of an antibody that is less than full-length, retaining at least a portion of the full-length antibody's specific binding ability. Examples of antibody fragments include, but are not limited to, Fab, Fab', F(ab)$_2$, single-chain Fvs (scFV), FV, dsFV diabody and Fd fragments. The fragment can include multiple chains linked together, such as by disulfide bridges. An antibody fragment generally contains at least about 50 amino acids and typically at least 200 amino acids.

As used herein, an Fv antibody fragment is composed of one variable heavy domain ($V_H$) and one variable light domain linked by noncovalent interactions.

As used herein, a dsFV refers to an Fv with an engineered intermolecular disulfide bond, which stabilizes the $V_H$-$V_L$ pair.

As used herein, an F(ab)$_2$ fragment is an antibody fragment that results from digestion of an immunoglobulin with pepsin at pH 4.0-4.5; it can be recombinantly expressed to produce the equivalent fragment.

As used herein, Fab fragments are antibody fragments that result from digestion of an immunoglobulin with papain; they can be recombinantly expressed to produce the equivalent fragment.

As used herein, scFVs refer to antibody fragments that contain a variable light chain ($V_L$) and variable heavy chain ($V_H$) covalently connected by a polypeptide linker in any order. The linker is of a length such that the two variable domains are bridged without substantial interference. Included linkers are (Gly-Ser)$_n$residues with some Glu or Lys residues dispersed throughout to increase solubility.

As used herein, humanized antibodies refer to antibodies that are modified to include human sequences of amino acids so that administration to a human does not provoke an immune response. Methods for preparation of such antibodies are known. For example, to produce such antibodies, the encoding nucleic acid in the hybridoma or other prokaryotic or eukaryotic cell, such as an *E. coli* or a CHO cell, that expresses the monoclonal antibody is altered by recombinant nucleic acid techniques to express an antibody in which the amino acid composition of the non-variable region is based on human antibodies. Computer programs have been designed to identify such non-variable regions.

As used herein, diabodies are dimeric scFV; diabodies typically have shorter peptide linkers than scFvs, and they generally dimerize.

As used herein, production by recombinant means by using recombinant DNA methods means the use of the well known methods of molecular biology for expressing proteins encoded by cloned DNA.

As used herein, an effective amount of a compound for treating a particular disease is an amount that is sufficient to ameliorate, or in some manner reduce the symptoms associated with the disease. Such amount can be administered as a single dosage or can be administered according to a regimen, whereby it is effective. The amount can cure the disease but, typically, is administered in order to ameliorate the symptoms of the disease. Repeated administration can be required to achieve the desired amelioration of symptoms.

As used herein, a compound that modulates the activity of a gene product either decreases or increases or otherwise alters the activity of the protein or, in some manner up- or down-regulates or otherwise alters expression of the nucleic acid in a cell.

As used herein, pharmaceutically acceptable salts, esters or other derivatives of the conjugates include any salts, esters or derivatives that can be readily prepared by those of skill in this art using known methods for such derivatization and that produce compounds that can be administered to animals or humans without substantial toxic effects and that either are pharmaceutically active or are prodrugs.

As used herein, a drug or compound identified by the screening methods provided herein refers to any compound that is a candidate for use as a therapeutic or as a lead compound for the design of a therapeutic. Such compounds can be small molecules, including small organic molecules, peptides, peptide mimetics, antisense molecules or dsRNA, such as RNAi, antibodies, fragments of antibodies, recombinant antibodies and other such compounds that can serve as drug candidates or lead compounds.

As used herein, a non-malignant cell adjacent to a malignant cell in a subject, refers to a cell that has a normal morphology (e.g., is not classified as neoplastic or malignant by a pathologist, cell sorter, or other cell classification method), but, while the cell had been present in tact in the subject, the cell had been adjacent to a malignant cell or malignant cells. As provided herein, cells of a particular type (e.g., stroma)

adjacent to a malignant cell or malignant cells can display an expression pattern that differs from cells of the same type that are not adjacent to a malignant cell or malignant cells. In accordance with the methods provided herein, cells that are adjacent to malignant cells can be distinguished from cells of the same type that are adjacent to non-malignant cells, according to their differential gene expression. As used herein regarding the location of cells, adjacent refers to a first cell and a second cell being sufficiently proximal such that the first cell influences the gene expression of the second cell. For example, adjacent cells can include cells that are in direct contact with each other, adjacent cell can include cells within 500 microns, 300 microns, 200 microns 100 microns or 50 microns, of each other.

As used herein, tumor refers to a collection of malignant cells. Malignant as applied to a cell refers to a cell that grows in an uncontrolled fashion. In some embodiments, a malignant cell can be anaplastic. In some embodiments, a malignant cell can be capable of metastasizing.

As used herein: stringency of hybridization in determining percentage mismatch is as follows:
1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

As used herein, vector (or plasmid) refers to discrete elements that are used to introduce heterologous nucleic acid into cells for either expression or replication thereof. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art. An expression vector includes vectors capable of expressing DNA that is operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those that integrate into the host cell genome.

As used herein a disease prognosis refers to a forecast of the probable outcome of a disease or of a probable outcome resultant from a disease. Non-limiting examples of disease prognosis include likely relapse of disease, likely aggressiveness of disease, likely indolence of disease, likelihood of survival of the subject, likelihood of success in treating a disease, condition in which a particular treatment regimen is likely to be more effective than another treatment regimen, and combinations thereof.

As used herein, aggressiveness of a tumor or malignant cell refers to the capacity of one or more cells to attain a position in the body away from the tissue or organ of origin, attach to another portion of the body, and multiply. Experimentally, aggressiveness can be described in one or more manners, including, but not limited to, post-diagnosis survival of subject, relapse of tumor, and metastasis of tumor. Thus, in the disclosures provided herein, data indicative of time length of survival, relapse, non-relapse, time length for metastasis, or non-metastasis, are indicative of the aggressiveness of a tumor or a malignant cell. When survival is considered, one skilled in the art will recognize that aggressiveness is inversely related to the length of time of survival of the subject. When time length for metastasis is considered, one skilled in the art will recognize that aggressiveness is directly related to the length of time of survival of a subject. As used herein, indolence refers to non-aggressiveness of a tumor or malignant cell; thus, the more aggressive a tumor or cell, the less indolent, and vice versa. As an example of a cell attaining a position in the body away from the tissue or organ of origin, a malignant prostate cell can attain an extra-prostatic position, and thus have one characteristic of an aggressive malignant cell. Attachment of cells can be, for example, on the lymph node or bone marrow of a subject, or other sites known in the art.

As used herein, a combination refers to any association between two or among more items.

As used herein, a composition refers to any mixture. It can be a solution, a suspension, liquid, powder, a paste, aqueous, non-aqueous or any combination thereof.

As used herein, fluid refers to any composition that can flow. Fluids thus encompass compositions that are in the form of semi-solids, pastes, solutions, aqueous mixtures, gels, lotions, creams and other such compositions.

For clarity of disclosure, and not by way of limitation, the detailed description is divided into the subsections that follow.

Cell-type-associated patterns of gene expression

Primary tissues are composed of many (e.g., 2 or more) types of cells. Identification of genes expressed in a specific cell type present within a tissue in other methods can require physical separation of that cell type and the cell type's subsequent assay. Although it is possible to physically separate cells according to type, by methods such as laser capture microdissection, centrifugation, FACS, and the like, this is time consuming and costly and in certain embodiments impractical to perform. Known expression profiling assays (either RNA or protein) of primary tissues or other specimens containing multiple cell types either (1) do not take into account that multiple cell types are present or (2) physically separate the component cell types before performing the assay. Other analyses have been performed without regard to the presence of multiple cell types, thereby identifying markers indicative of a shift in the relative proportion of various cell types present in a sample, but not representative of a specific cell type. Previous analytic approaches cannot discern interactions between different types of cells.

Provided herein are methods, compositions and kits based on the development of a model, where the level of each gene product assayed can be correlated to a specific cell type. This approach for determination of cell-type-specific gene expression obviates the need for physical separation of cells from tissues or other specimens with heterogeneous cell content. Furthermore, this method permits determination of the interaction between the different types of cells contained in such heterogeneous mixtures, which would otherwise have been difficult or impossible had the cells been first physically separated and then assayed. Using the approaches provided herein, a number of biomarkers can be identified related to various diseases and disorders. Exemplified herein is the identification of biomarkers for prostate cancer and benign prostatic hypertopy. Such biomarkers can be used in diagnosis and prognosis and treatment decisions.

The methods, compositions, combinations and kits provided herein employ a regression-based approach for identification of cell-type-specific patterns of gene expression in samples containing more than one type of cell. In one example, the methods, compositions, combinations and kits provided herein employ a regression-based approach for identification of cell-type-specific patterns of gene expression in cancer. These methods, compositions, combinations and kits provided herein can be used in the identification of genes that are differentially expressed in malignant versus non-malignant cells and further identify tumor-dependent changes in gene expression of non-malignant cells associated with malignant cells relative to non-malignant cells not associated with malignant cells. The methods, compositions, combinations and kits provided herein also can be used in correlating a phenotype with gene expression in one or more cell types. For example such a method can include determining the relative content of each cell type in two or more related heterogeneous cell samples, wherein at least two of the samples do not contain the same relative content of each cell type, measuring overall levels of one or more gene expression analytes in each sample, determining the regression relationship between the relative content of each cell type and the measured overall levels, and calculating the level of each of the one or more analytes in each cell type according to the regression relationship, where gene expression levels correspond to the calculated levels of analytes. In another example such a method can include determining the relative content of each cell type in two or more related heterogeneous cell samples, wherein at least two of the samples do not contain the same relative content of each cell type, measuring overall levels of two or more gene expression analytes in each sample, determining the regression relationship between the relative content of each cell type and the measured overall levels, and calculating the level of each of the two or more analytes in each cell type according to the regression relationship, where gene expression levels correspond to the calculated levels of analytes. Such methods can further include identifying genes differentially expressed in at least one cell type relative to at least one other cell type. In such methods, the analyte can be a nucleic acid molecule and a protein.

The methods provided herein can be used for determining cell-type-specific gene expression in any heterogeneous cell population. The methods provided herein can find application in samples known to contain a variety of cell types, such as brain tissue samples and muscle tissue samples. The methods provided herein also can find application in samples in which separation of cell type can represent a tedious or time consuming operation, which is no longer required under the methods provided herein. Samples used in the present methods can be any of a variety of samples, including, but not limited to, blood, cells from blood (including, but not limited to, non-blood cells such as epithelial cells in blood), plasma, serum, spinal fluid, lymph fluid, skin, sputum, alimentary and genitourinary samples (including, but not limited to, urine, semen, seminal fluid, prostate aspirate, prostatic fluid, and fluid from the seminal vesicles), saliva, milk, tissue specimens (including, but not limited to, prostate tissue specimens), tumors, organs, and also samples of in vitro cell culture constituents.

In certain embodiments, the methods provided herein can be used to differentiate true markers of tumor cells, hyperplastic cells, and stromal cells of cancer. As exemplified herein, least squares regression using individual cell-type proportions can be used to produce clear predictions of cell-specific expression for a large number of genes. In an example provided herein applied to prostate cancer, many of these predictions are accepted on the basis of prior knowledge of prostate gene expression and biology, which provide confidence in the method. These are illustrated by numerous genes predicted to be preferentially expressed by stromal cells that are characteristic of connective tissue and only poorly expressed or absent in epithelial cells.

In some embodiments, the methods provided herein allow segregation of molecular tumor and nontumor markers into more discrete and informative groups. Thus, genes identified as tumor-associated can be further categorized into tumor versus stroma (epithelial versus mesenchymal) and tumor versus hyperplastic (perhaps reflecting true differences between the malignant cell and its hyperplastic counterpart). The methods provided herein can be used to distinguish tumor and non-tumor markers in a variety of cancers, including, but not limited to cancers classified by site such as cancer of the oral cavity and pharynx (lip, tongue, salivary gland, floor of mouth, gum and other mouth, nasopharynx, tonsil, oropharynx, hypopharynx, other oral/pharynx); cancers of the digestive system (esophagus; stomach; small intestine; colon and rectum; anus, anal canal, and anorectum; liver; intrahepatic bile duct; gallbladder; other biliary; pancreas; retroperitoneum; peritoneum, omentum, and mesentery; other digestive); cancers of the respiratory system (nasal cavity, middle ear, and sinuses; larynx; lung and bronchus; pleura; trachea, mediastinum, and other respiratory); cancers of the mesothelioma; bones and joints; and soft tissue, including heart; skin cancers, including melanomas and other non-epithelial skin cancers; Kaposi's sarcoma and breast cancer; cancer of the female genital system (cervix.uteri; corpus uteri; uterus, nos; ovary; vagina; vulva; and other female genital); cancers of the male genital system (prostate gland; testis; penis; and other male genital); cancers of the urinary system (urinary bladder; kidney and renal pelvis; ureter; and other urinary); cancers of the eye and orbit; cancers of the brain and nervous system (brain; and other nervous system); cancers of the endocrine system (thyroid gland and other endocrine, including thymus); lymphomas (Hodgkin's disease and non-Hodgkin's lymphoma), multiple myeloma, and leukemias (lymphocytic leukemia; myeloid leukemia; monocytic leukemia; and other leukemias); and cancers classified by histological type, such as Neoplasm, malignant; Carcinoma, NOS; Carcinoma, undifferentiated, NOS; Giant and spindle cell carcinoma; Small cell carcinoma, NOS; Papillary carcinoma, NOS; Squamous cell carcinoma, NOS; Lymphoepithelial carcinoma; Basal cell carcinoma, NOS; Pilomatrix carcinoma; Transitional cell carcinoma, NOS; Papillary transitional cell carcinoma; Adenocarcinoma, NOS; Gastrinoma, malignant; Cholangiocarcinoma; Hepatocellular carcinoma, NOS; Combined hepatocellular carcinoma and cholangiocarcinoma; Trabecular adenocarcinoma; Adenoid cystic carcinoma; Adenocarcinoma in adenomatous polyp; Adenocarcinoma, familial polyposis coli; Solid carcinoma, NOS; Carcinoid tumor, malignant; Bronchiolo-alveolar adenocarcinoma; Papillary adenocarcinoma, NOS; Chromophobe carcinoma; Acidophil carcinoma; oxyphilic adenocarcinoma; Basophil carcinoma; Clear cell adenocarcinoma, NOS; Granular cell carcinoma; Follicular adenocarcinoma, NOS; Papillary and follicular adenocarcinoma; Non-encapsulating sclerosing carcinoma; Adrenal cortical carcinoma; Endometroid carcinoma; Skin appendage carcinoma; Apocrine adenocarcinoma; Sebaceous adenocarcinoma; Ceruminous adenocarcinoma; Mucoepidermoid carcinoma; Cystadenocarcinoma, NOS; Papillary cystadenocarcinoma, NOS; Papillary serous cystadenocarcinoma; Mucinous cystadenocarcinoma, NOS; Mucinous adenocarcinoma; Signet ring cell carcinoma; Infiltrating duct carcinoma; Medullary carcinoma, NOS; Lobular carcinoma; Inflammatory carcinoma; Paget's disease, mammary; Acinar cell carcinoma; Adenosquamous carcinoma; Adenocarcinoma w/squamous metaplasia; Thymoma, malignant; Ovarian stromal tumor, malignant; Thecoma, malignant; Granulosa cell tumor, malignant; Androblastoma, malignant;

Sertoli cell carcinoma; Leydig cell tumor, malignant; Lipid cell tumor, malignant; Paraganglioma, malignant; Extramammary paraganglioma, malignant; Pheochromocytoma; Glomangiosarcoma; Malignant melanoma, NOS; Amelanotic melanoma; Superficial spreading melanoma; Malig melanoma in giant pigmented nevus; Epithelioid cell melanoma; Blue nevus, malignant; Sarcoma, NOS; Fibrosarcoma, NOS; Fibrous histiocytoma, malignant; Myxosarcoma; Liposarcoma, NOS; Leiomyosarcoma, NOS; Rhabdomyosarcoma, NOS; Embryonal rhabdomyosarcoma; Alveolar rhabdomyosarcoma; Stromal sarcoma, NOS; Mixed tumor, malignant, NOS; Mullerian mixed tumor; Nephroblastoma; Hepatoblastoma; Carcinosarcoma, NOS; Mesenchymoma, malignant; Brenner tumor, malignant; Phyllodes tumor, malignant; Synovial sarcoma, NOS; Mesothelioma, malignant; Dysgerminoma; Embryonal carcinoma, NOS; Teratoma, malignant, NOS; Struma ovarii, malignant; Choriocarcinoma; Mesonephroma, malignant; Hemangiosarcoma; Hemangioendothelioma, malignant; Kaposi's sarcoma; Hemangiopericytoma, malignant; Lymphangiosarcoma; Osteosarcoma, NOS; Juxtacortical osteosarcoma; Chondrosarcoma, NOS; Chondroblastoma, malignant; Mesenchymal chondrosarcoma; Giant cell tumor of bone; Ewing's sarcoma; Odontogenic tumor, malignant; Ameloblastic odontosarcoma; Ameloblastoma, malignant; Ameloblastic fibrosarcoma; Pinealoma, malignant; Chordoma; Glioma, malignant; Ependymoma, NOS; Astrocytoma, NOS; Protoplasmic astrocytoma; Fibrillary astrocytoma; Astroblastoma; Glioblastoma, NOS; Oligodendroglioma, NOS; Oligodendroblastoma; Primitive neuroectodermal; Cerebellar sarcoma, NOS; Ganglioneuroblastoma; Neuroblastoma, NOS; Retinoblastoma, NOS; Olfactory neurogenic tumor; Meningioma, malignant; Neurofibrosarcoma; Neurilemmoma, malignant; Granular cell tumor, malignant; Malignant lymphoma, NOS; Hodgkin's disease, NOS; Hodgkin's; paragranuloma, NOS; Malignant lymphoma, small lymphocytic; Malignant lymphoma, large cell, diffuse; Malignant lymphoma, follicular, NOS; Mycosis fungoides; Other specified non-Hodgkin's lymphomas; Malignant histiocytosis; Multiple myeloma; Mast cell sarcoma; Immunoproliferative small intestinal disease; Leukemia, NOS; Lymphoid leukemia, NOS; Plasma cell leukemia; Erythroleukemia; Lymphosarcoma cell leukemia; Myeloid leukemia, NOS; Basophilic leukemia; Eosinophilic leukemia; Monocytic leukemia, NOS; Mast cell leukemia; Megakaryoblastic leukemia; Myeloid sarcoma; and Hairy cell leukemia.

In an example comparing the results of a prostate tissue analysis using the methods provided herein to the results of previous methods, the vast majority of markers associated with normal prostate tissues in previous microarray-based studies relate to cells of the stroma. This result is not surprising given that normal samples can be composed of a relatively greater proportion of stromal cells.

In the example of prostate analysis, the strongest single discriminator between benign prostate hyperplasia (BPH) cells and tumor cells was CK15, a result confirmed by immunohistochemistry. CK15 has previously received little attention in this context, but BPH markers play an important role in the diagnosis of ambiguous clinical cases.

Transcripts whose expression levels have high covariance with cross-products of tissue proportions suggest that expression in one cell type depends on the proportion of another tissue, as would be expected in a paracrine mechanism. The stroma transcript with the highest dependence on tumor percentage was TGF-β2. Another such stroma cell gene for which immunohistochemistry was practical was desmin, which showed altered staining in the tumor-associated stroma. In fact, a large number of typical stroma cell genes displayed dependence on the proportion of tumor, adding evidence to the speculation that tumor-associated stroma differs from non-associated stroma. Tumor-stroma paracrine signaling can be reflected in peritumor halos of altered gene expression that can present a much bigger target for detection than the tumor cells alone.

The methods provided herein provide a straightforward approach using simple and multiple linear regression to identify genes whose expression in tissue is specifically correlated with a specific cell type (e.g., in prostate tissue with either tumor cells, BPH epithelial cells or stromal cells). Context-dependent expression that is not readily attributable to single cell types is also recognized. The investigative approach described here is also applicable to a wide variety of tumor marker discovery investigations in a variety of tissues and organs. The exemplary prostate analysis results presented herein demonstrate the ability to identify a large number of gene candidates as specific products of various cells involved in prostate cancer pathogenesis.

A model for cell-specific gene expression is established by both (1) determination of the proportion of each constituent cell type (e.g., epithelium, stroma, tumor, or other discriminating entity) within a given type of tissue or specimen (e.g., prostate, breast, colon, marrow, and the like) and (2) assay of the expression profile (e.g., RNA or protein) of that same tissue or specimen. In some embodiments, cell type specific expression of a gene can be determined by fitting this model to data from a collection of tissue samples.

The methods provided herein can include a step of determining the relative content of each cell type in a heterogeneous sample. Identification of a cell type in a sample can include identifying cell types that are present in a sample in amounts greater than about 1%, 2%, 3%, 4% or 5% or greater than 1%, 2%, 3%, 4% or 5%.

Any of a variety of known methods for cell type identification can be used herein. For example, cell type can be determined by an individual skilled in the ability to identify cell types, such as a pathologist or a histologist. In another example, cell types can be determined by cell sorting and/or flow cytometry methods known in the art.

The methods provided herein can be used to determine that the nucleotide or proteins are differentially expressed in at least one cell type relative to at least one other cell type. Such genes include those that are up-regulated (i.e. expressed at a higher level), as well as those that are down-regulated (i.e. expressed at a lower level). Such genes also include sequences that have been altered (i.e., truncated sequences or sequences with substitutions, deletions or insertions, including point mutations) and show either the same expression profile or an altered profile. In certain embodiments, the genes can be from humans; however, as will be appreciated by those in the art, genes from other organisms can be useful in animal models of disease and drug evaluation; thus, other genes are provided, from vertebrates, including mammals, including rodents (rats, mice, hamsters, guinea pigs, etc.), primates, and farm animals (including sheep, goats, pigs, cows, horses, etc). In some cases, prokaryotic genes can be useful. Gene expression in any of a variety of organisms can be determined by methods provided herein or otherwise known in the art.

Gene products measured according to the methods provided herein can be nucleic acid molecules, including, but not limited to mRNA or an amplicate or complement thereof, polypeptides, or fragments thereof. Methods and compositions for the detection of nucleic acid molecules and proteins are known in the art. For example, oligonucleotide probes and primers can be used in the detection of nucleic acid molecules, and antibodies can be used in the detection of polypeptides.

In the methods provided herein, one or more gene products can be detected. In some embodiments, two or more gene products are detected. In other embodiments, 3 or more, 4 or more, 5 or more, 7 or more, 10 or more 15 or more, 20 or more 25, or more, 35 or more, 50 or more, 75 or more, or 100 or more gene products can be detected in the methods provided herein.

The expression levels of the marker genes in a sample can be determined by any method or composition known in the art. The expression level can be determined by isolating and determining the level (i.e., amount) of nucleic acid transcribed from each marker gene. Alternatively, or additionally, the level of specific proteins translated from mRNA transcribed from a marker gene can be determined.

Determining the level of expression of specific marker genes can be accomplished by determining the amount of mRNA, or polynucleotides derived therefrom, or protein present in a sample. Any method for determining protein or RNA levels can be used. For example, protein or RNA is isolated from a sample and separated by gel electrophoresis. The separated protein or RNA is then transferred to a solid support, such as a filter. Nucleic acid or protein (e.g., antibody) probes representing one or more markers are then hybridized to the filter by hybridization, and the amount of marker-derived protein or RNA is determined. Such determination can be visual, or machine-aided, for example, by use of a densitometer. Another method of determining protein or RNA levels is by use of a dot-blot or a slot-blot. In this method, protein, RNA, or nucleic acid derived therefrom, from a sample is labeled. The protein, RNA or nucleic acid derived therefrom is then hybridized to a filter containing oligonucleotides or antibodies derived from one or more marker genes, wherein the oligonucleotides or antibodies are placed upon the filter at discrete, easily-identifiable locations. Binding, or lack thereof, of the labeled protein or RNA to the filter is determined visually or by densitometer. Proteins or polynucleotides can be labeled using a radiolabel or a fluorescent (i.e., visible) label.

Methods provided herein can be used to detect mRNA or amplicates thereof, and any fragment thereof. In one example, introns of mRNA or amplicate or fragment thereof can be detected. Processing of mRNA can include splicing, in which introns are removed from the transcript. Detection of introns can be used to detect the presence of the entire mRNA, and also can be used to detect processing of the mRNA, for example, when the intron region alone (e.g., intron not attached to any exons) is detected.

In another embodiment, methods provided herein can be used to detect polypeptides and modifications thereof, where a modification of a polypeptide can be a post-translation modification such as lipidylation, glycosylation, activating proteolysis, and others known in the art, or can include degradational modification such as proteolytic fragments and ubiquitinated polypeptides.

These examples are not intended to be limiting; other methods of determining protein or RNA abundance are known in the art.

Alternatively, proteins can be separated by two-dimensional gel electrophoresis systems. Two-dimensional gel electrophoresis is well-known in the art and can involve isoelectric focusing along a first dimension followed by SDS-PAGE electrophoresis along a second dimension. See, e.g., Hames et al, 1990, GEL ELECTROPHORESIS OF PROTEINS: A PRACTICAL APPROACH, IRL Press, New York; Shevchenko et al., Proc. Nat'l Acad. Sci. USA 93:1440-1445 (1996); Sagliocco et al., Yeast 12:1519-1533 (1996); Lander, Science 274:536-539 (1996). The resulting electropherograms can be analyzed by numerous techniques, including mass spectrometric techniques, western blotting and immunoblot analysis using polyclonal and monoclonal antibodies.

Alternatively, marker-derived protein levels can be determined by constructing an antibody microarray in which binding sites comprise immobilized antibodies, such as monoclonal antibodies, specific to a plurality of protein species encoded by the cell genome. Antibodies can be present for a substantial fraction of the marker-derived proteins of interest. Methods for making monoclonal antibodies are well known (see, e.g., Harlow and Lane, 1988, ANTIBODIES: A LABORATORY MANUAL, Cold Spring Harbor, N.Y., which is incorporated in its entirety for all purposes). In one embodiment, monoclonal antibodies are raised against synthetic peptide fragments designed based on genomic sequence of the cell. With such an antibody array, proteins from the cell are contacted to the array, and their binding is assayed with assays known in the art. The expression, and the level of expression, of proteins of diagnostic or prognostic interest can be detected through immunohistochemical staining of tissue slices or sections.

In another embodiment, expression of marker genes in a number of tissue specimens can be characterized using a tissue array (Kononen et al., Nat. Med 4(7):844-7 (1998)). In a tissue array, multiple tissue samples are assessed on the same microarray. The arrays allow in situ detection of RNA and protein levels; consecutive sections allow the analysis of multiple samples simultaneously.

In some embodiments, polynucleotide microarrays are used to measure expression so that the expression status of each of the markers above is assessed simultaneously. In one embodiment, the microarrays provided herein are oligonucleotide or cDNA arrays comprising probes hybridizable to the genes corresponding to the marker genes described herein.

The microarrays provided herein can comprise probes hybridizable to the genes corresponding to markers able to distinguish cells, identify phenotypes, identify a disease or disorder, or provide a prognosis of a disease or disorder. In particular, provided herein are polynucleotide arrays comprising probes to a subset or subsets of at least 2, 5, 10, 15, 20, 30, 40, 50, 75, 100, 150, 200, 300, 400, 500, 750, 1,000, 1,250, 1,500, 1,750, 2,000, 2,250, 2,500, 2750, 3000, 3500, 4000, 4500, 5000, or more, genetic markers, up to the full set of markers listed in SEQ ID NO:1-38,826. In some embodiments, the nucleotide sequences selected from SEQ ID NO:1-38,826 are selected from SEQ ID NO:35,580-38,826. Also provided herein are probes to markers with a modified t statistic greater than or equal to 2.5, 3, 3.5, 4, 4.5 or 5. Also provided herein are probes to markers with a modified t statistic less than or equal to −2.5, −3, −3.5, −4, −4.5 or −5. In specific embodiments, the invention provides combinations such as arrays in which the markers described herein comprise at least 50%, 60%, 70%, 80%, 85%, 90%, 95% or 98% of the probes on the combination or array.

General methods pertaining to the construction of microarrays comprising the marker sets and/or subsets above are known in the art as described herein.

Microarrays can be prepared by selecting probes that comprise a polypeptide or polynucleotide sequence, and then immobilizing such probes to a solid support or surface. For example, the probes can comprise DNA sequences, RNA sequences, or antibodies. The probes can also comprise amino acid, DNA and/or RNA analogues, or combinations thereof. The probes can be prepared by any method known in the art.

The probe or probes used in the methods of the invention can be immobilized to a solid support which can be either porous or non-porous. For example, the probes of the can be attached to a nitrocellulose or nylon membrane or filter. Alternatively, the solid support or surface can be a glass or plastic surface. In another embodiment, hybridization levels are measured to microarrays of probes consisting of a solid phase on the surface of which are immobilized a population of probes. The solid phase can be a nonporous or, optionally, a porous material such as a gel.

In another embodiment, the microarrays are addressable arrays, such as positionally addressable arrays. More specifically, each probe of the array can be located at a known, predetermined position on the solid support such that the identity (i.e., the sequence) of each probe can be determined from its position in the array (i.e., on the support or surface).

A skilled artisan will appreciate that positive control probes, e.g., probes known to be complementary and hybridizable to sequences in target polynucleotide molecules, and negative control probes, e.g., probes known to not be complementary and hybridizable to sequences in target polynucleotide molecules, can be included on the array. In one embodiment, positive controls can be synthesized along the perimeter of the array. In another embodiment, positive controls can be synthesized in diagonal stripes across the array. Other variations are known in the art. Probes can be immobilized on the to solid surface by any of a variety of methods known in the art.

In certain embodiments, this model can be further extended to include sample characteristics, such as cell or organism phenotypes, allowing cell type specific expression to be linked to observable indicia such as clinical indicators and prognosis (e.g., clinical disease progression, response to therapy, and the like). In one embodiment, a model for prostate tissue is provided, resulting in identification of cell-type-specific markers of cancer, epithelial hypertrophy, and disease progression. In another embodiment, a method for studying differential gene expression between subjects with cancers that relapse and those with cancers that do not relapse, is disclosed. Also provided is the framework for studying mixed cell type samples and more flexible models allowing for cross-talk among genes in a sample. Also provided are extensions to defining differences in expression between samples with different characteristics, such as samples from subjects who subsequently relapse versus those who do not.

Statistical Treatment

The methods provided herein include determining the regression relationship between relative cell content and measured expression levels. For example, the regression relationship can be determined by determining the regression of measured expression levels on cell proportions. Statistical methods for determining regression relationships between variables are known in the art. Such general statistical methods can be used in accordance with the teachings provided herein regarding regression of measured expression levels on cell proportions.

The methods provided herein also include calculating the level of analytes in each cell type based on the regression relationship between relative cell content and expression levels. The regression relationship can be determined according to methods provided herein, and, based on the regression relationship, the level of a particular analyte can be calculated for a particular cell type. The methods provided herein can permit the calculation of any of a variety of analyte for particular cell types. For example, the methods provided herein can permit calculation of a single analyte for a single cell type, or can permit calculation of a plurality of analytes for a single cell type, or can permit calculation of a single analyte for a plurality of cell types, or can permit calculation of a plurality of analytes for a plurality of cell types. Thus, the number of analytes whose level can be calculated for a particular cell type can range from a single analyte to the total number of analytes measured (e.g., the total number of analytes measured using a microarray). In another embodiment, the total number of cell types for which analyte levels can be calculated can range from a single cell type, to all cell types present in a sample at sufficient levels. The levels of analyte for a particular cell type can be used to estimate expression levels of the corresponding gene, as provided elsewhere herein.

The methods provided herein also can include identifying genes differentially expressed in a first cell type relative to a second cell type. Expression levels of one or more genes in a particular cell type can be compared to one or more additional cell types. Differences in expression levels can be represented in any of a variety of manners known in the art, including mathematical or statistical representations, as provided herein. For example, differences in expression level can be represented as a modified t statistic, as described elsewhere herein.

The methods provided herein also can serve as the basis for methods of indicating the presence of a particular cell type in a subject. The methods provided herein can be used for identifying the expression levels in particular cell types. Using any of a variety of classifier methods known in the art, such as a naive Bayes classifier, gene expression levels in cells of a sample from a subject can be compared to reference expression levels to determine the presence of absence, and, optionally, the relative amount, of a particular cell type in the sample. For example, the markers provided herein as associated with prostate tumor, stroma or BPH can be selected in a prostate tumor classifier in accordance with the modified t statistic associated with each marker provided in the Tables herein. Methods for using a modified-t statistic in classifier methods are provided herein and also are known in the art. In another embodiment, the methods provided herein can be used in phenotype-indicating methods such as diagnostic or prognostic methods, in which the gene expression levels in a sample from a subject can be compared to references indicative of one or more particular phenotypes.

For purposes of exemplification, and not for purposes of limitation, an exemplary method of determining gene expression levels in one or more cell types in a heterogeneous cell sample is provided as follows. Suppose that there are four cell types: BPH, Tumor, Stroma, and Cystic Atrophy. Supposing that each cell type has a (possibly) different distribution for y, the expression level for a gene j, denoted by:

$f_{ij}(y), i \in \{BPH, \text{Tumor}, \text{Stromia}, \text{Cystic Atrophy}\}$ and that sample k has proportions $X_k = (x_{k,BPH}, x_{k,Tumor}, x_{k,Cystic\ Atrophy})$ of each cell type is studied. The distribution of the expression level for gene j is then $$g_j(y|X_k) = \sum_i x_{ki} f_{ij}(y)$$

if the expression levels are additive in the cell proportions as they would be if each cell's expression level depends only on the type of cell (and not, say, on what other types of cells can be present in the sample). In a later section this formulation is extended to cases in which the expression of a given cell type depends on what other types of cells are present.

The average expression level in a sample is then the weighted average of the expectations with weights corresponding to the cell proportions:

$$E_{g_j}(y|X_k) = \sum_i x_{ki} E_{f_{ij}}(y)$$

or $$y_{jk} = \sum_i x_{ki} \beta_{ij} + \epsilon_{jk}$$

where $$E_{f_{ij}}(y) = \beta_{ij} \text{ and } \epsilon_{jk} = y_{jk} - E_{g_j}(y|X_k)$$

This is the known form for a multiple linear regression equation (without specifying an intercept), and when multiple samples are available one can estimate the $\beta_{ij}$. Once these estimates are in hand, estimates for the differences in gene expression of two cell types are of the form:

$$\hat{\beta}_{i_1 j} - \hat{\beta}_{i_2 j}$$

and standard methods for testing linear hypotheses about the coefficients $\beta_{ij}$ can be applied to test whether the average expression levels of cell types $i_1$ and $i_2$ are different. The term 'expression levels' as used in this exemplification of the method is used in a generic sense: 'expression levels' could be readings of mRNA levels, cRNA levels, protein levels, fluorescent intensity from a feature on an array, the logarithm of that reading, some highly post-processed reading, and the like. Thus, differences in the coefficients can correspond to differences, log ratios, or some other functions of the underlying transcript abundance.

For computational convenience, one may in certain embodiments use $Z=XT$ and $\gamma=T^{-1}\beta$ setting up $T$ so that one column of $T$ has all zeroes but for a one in position $i_1$ and a minus one in position $i_2$ such as $$T = \begin{pmatrix} 1 & 1 & -1 & 0 \\ 1 & 1 & 1 & 0 \\ 1 & 0 & 0 & 1 \\ 1 & 0 & 0 & 0 \end{pmatrix}$$

The columns of Z that result are the unit vector (all ones), $X_{k,BPH}+X_{k,Tumor}$, $X_{k,BPH}-X_{k,Tumor}$, and $X_{k,Stroma}$. With this setup, twice the coefficient of $X_{k,BPH}-X_{k,Tumor}$ estimates the average difference in expression level of a tumor cell versus a BPH cell. With this parametrization, standard software can be used to provide an estimate and a tesmodified t statistic for the average difference of tumor and BPH cells. Further, this can simplify the specification of restricted models in which two or more of the tissue components have the same average expression level.

The data for a study can contain a large number of samples from a smaller number of different men. It is plausible that the samples from one man may tend to share a common level of expression for a given gene, differences among his cells according to their type notwithstanding. This will tend to lead to positive covariance among the measurements of expression level within men. Ordinary least squares (OLS) estimates are less than fully efficient in such circumstances. One alternative to OLS is to use a weighted least squares approach that treats a collection of samples from a single subject as having a common (non-negative) covariance and identical variances.

The estimating equation for this setup can be solved via iterative methods using software such as the gee library from R (Ross Ihaka and Robert Gentleman. R: A language for data analysis and graphics. Journal of Computational and Graphical Statistics, 5:299-314, 1996)). When the estimated covariance is negative—as sometimes happens when there is an extreme outlier in the dataset—it can be fixed at zero. Also the sandwich estimate (Kung-Yee Liang and Scott L. Zeger. Longitudinal data analysis using generalized linear models. Biometrika, 73:13-22, 1986.) of the covariance structure can be used.

The estimating equation approach will provide a tesmodified t statistic for a single transcript. Assessment of differential expression among a group of 12625 transcripts is handled by permutation methods that honor a suitable null model. That null model is obtained by regressing the expression level on all design terms except for the 'BPH-tumor' term using the exchangeable, non-negative correlation structure just mentioned. For performing permutation tests, the correlation structure in the residuals can be accounted for. Let $k_1$ be the set of $n_1$ indexes of samples for subject 1. First, we find $y_{jk} - \hat{y}_{jk} = e_{jk}$, $k \in k_1$, as the residuals from that fitted null model for subject 1. The inverse square root of the correlation matrix of these residuals is used to transform them, i.e. $\tilde{e}_j = \phi^{-1/2} e_j$, where $\phi$ is the (block diagonal) correlation matrix obtained by substituting the estimate of $r$ from gee as the off-diagonal elements of blocks corresponding to measurements for each subject and $e_j$ and $\tilde{e}_j$ are the vector of residuals and transformed residuals for all subjects for gene j. Asymptotically, the $\tilde{e}_{jk}$ have means and covariances equal to zero. Random permutations of these, $\tilde{e}_{j.}^{(i)}$, $i=1, \ldots, M$, are obtained and used to form pseudo-observations:

$$\tilde{y}_{j.}^{(i)} = \hat{y}_{j.} + \phi^{1/2} \tilde{e}_{j.}^{(i)}$$

This permutation scheme preserves the null model and enforces its correlation structure asymptotically.

In certain embodiments, the contribution of each type of cell does not depend on what other cell types are present in the sample. However, there can be instances in which contribution of each type of cell does depend on other cell types present in the sample. It may happen that putatively 'normal' cells exhibit genomic features that influence both their expression profiles and their potential to become malignant. Such cells would exhibit the same expression pattern when located in normal tissue, but are more likely to be found in samples that also have tumor cells in them. Another possible effect is that signals generated by tumor cells trigger expression changes in nearby cells that would not be seen if those same cells were located in wholly normal tissue. In either case, the contribution of a cell may be more or less than in another tissue environment leading to a setup in which the contributions of individual cell types to the overall profile depend on the proportions of all types present, viz.

$$g_j(y|X_k) = \sum_i x_{ki} f_{ij}(y|X_k)$$

as do the expected proportions $$E_{g_j}(y|X_k) = \sum_i x_{ki} E_{f_{ij}}(y|X_k)$$

or $$y_{jk} = \sum_i x_{ki}\beta_{ij} + (X_k) + \epsilon_{jk}$$

The methods used herein above can still be applied in the context provided some calculable form is given for $\beta_{ij}(X_k)$. One choice is given by $$\beta_{ij}(X_k)=(\phi_j R(X_k))_i$$

where $\Phi_j$ is a 4×m matrix of unknown coefficients and $R(X_k)$ is a column vector of m elements. This reduces to the case in which each cell's expression level depends only on the type of cell when $\Phi_j$ is 4×1 matrix and $R(X_k)$ is just '1'.

Consider the case:

$$\phi_j(X_k)R(X_k) = \begin{pmatrix} v_{Bj} & v_{Bj} & v_{Bj} & v_{Bj} \\ v_{Tj} & v_{Tj} & v_{Tj} & v_{Tj} \\ v_{Sj} & v_{Sj}+\delta_j & v_{Sj} & v_{Sj} \\ v_{Cj} & v_{Cj} & v_{Cj} & v_{Cj} \end{pmatrix} \begin{pmatrix} x_{k,B} \\ x_{k,T} \\ x_{k,S} \\ x_{k,C} \end{pmatrix} = \begin{pmatrix} v_{Bj} \\ v_{Tj} \\ v_{Sj}+\delta_j x_{k,T} \\ v_{Cj} \end{pmatrix}$$

$$\phi_j(X_k)R(X_k) = \begin{pmatrix} v_{Bj} & v_{Bj} & v_{Bj} & v_{Bj} \\ v_{Tj} & v_{Tj} & v_{Tj} & v_{Tj} \\ v_{Sj} & v_{Sj}+\delta_j & v_{Sj} & v_{Sj} \\ v_{Cj} & v_{Cj} & v_{Cj} & v_{Cj} \end{pmatrix} \begin{pmatrix} x_{k,B} \\ x_{k,T} \\ x_{k,S} \\ x_{k,C} \end{pmatrix} = \begin{pmatrix} v_{Bj} \\ v_{Tj} \\ v_{Sj}+\delta_j x_{k,T} \\ v_{Cj} \end{pmatrix}$$

(and recall that $\Sigma_j X_{k,j}=1$) Here the subscript for Tumor has been abbreviated T etc., for brevety. This setup provides that BPH (B), tumor, and cystic atrophy (C) cells have expression profiles that do not depend on the other cell types in the sample. However, the expression levels of stromal cells (S) depend on the proportion of tumor cells as reflected by the coefficient $\delta_j$. Notice that is linear in $X_{k,B}$, $X_{k,T}$, $X_{k,S}$, $X_{k,C}$, and $X_{k,S}X_{k,T}$ with the unknown $$X_k \phi_j R(X_k) = x_{k,B} v_{Bj} + x_{k,T} v_{Tj} + x_{k,S} v_{Sj} + x_{k,S} x_{k,T} \delta_j + x_{k,C} v_{Cj}$$

coefficients being multipliers of those terms. So, the unknowns in this case are linear functions of the gene expression levels and can be determined using standard linear models as was done earlier. The only change here is the addition of the product of $X_{k,s}$ and $X_{k,T}$. Such a product, when significant, is termed an "interaction" and refers to the product archiving a significance level owing to a correlation of $X_{k,S}$ with $X_{k,T}$. Thus, it is possible to accommodate variations in gene expression that occur when the level of a transcript in one cell type is influenced by the amount of another cell type in the sample. In one aspect, a setup involving a dependency of tumor on the amount of stroma $$\phi_j(X_k)R(X_k) = \begin{pmatrix} v_{Bj} & v_{Bj} & v_{Bj} & v_{Bj} \\ v_{Tj} & v_{Tj} & v_{Tj}+\delta_j & v_{Tj} \\ v_{Sj} & v_{Sj} & v_{Sj} & v_{Sj} \\ v_{Cj} & v_{Cj} & v_{Cj} & v_{Cj} \end{pmatrix} \begin{pmatrix} x_{k,B} \\ x_{k,T} \\ x_{k,S} \\ x_{k,C} \end{pmatrix} = \begin{pmatrix} v_{Bj} \\ v_{Tj}+\delta_j x_{k,T} \\ v_{Sj} \\ v_{Cj} \end{pmatrix}$$

the expression for $X_k \Phi_j R(X_k)$ is precisely as it was just above.

Accordingly, one can screen for dependencies by including as regressors products of the proportions of cell types. In certain embodiments, it may not be possible to detect interactions if two different cell types experience equal and opposite changes—one type expressing more with increases in the other and the other expressing less with increases in the first. In one embodiment, dependence of gene expression refers to the dependence of gene expression in one cell type on the level of gene expression in another cell type. In another embodiment, dependence of gene expression refers to the dependence of gene expression in one cell type on the amount of another cell type.

The contribution of each type of cell can depend on what other cell types are present in the sample, but also can depend on other characteristics of the sample, such as clinical characteristics of the subject who contributed it. For example, clinical characteristics such as disease symptoms, disease prognosis such as relapse and/or aggressiveness of disease, likelihood of success in treating a disease, likelihood of survival, condition in which a particular treatment regimen is likely to be more effective than another treatment regimen, can be correlated with cell expression. For example, cell type specific gene expression can differ between a subject with a cancer that does not relapse after treatment and a subject with a cancer that does relapse after treatment. In this case, the contribution of a cell type may be more or less than in another subject leading to an instance in which the contributions of individual cell types to the overall profile depend on the characteristics of the subject or sample. Here, the model used earlier is extended to allow for dependence on a vector of sample specific covariates, $Z_k$:

$$g_j(y|X_k, Z_k) = \sum_i x_{ki} f_{ij}(y|X_k, Z_k)$$

as do the expected proportions:

$$E_{g_j}(y|X_k, Z_k) = \sum_i x_{ki} E_{f_{ij}}(y|X_k, Z_k)$$

or $$y_{jk} = \sum_i x_{ki}\beta_{ij} + (X_k, Z_k) + \epsilon_{jk}$$

where $$E_{f_{ij}}(y|X_k, Z_k) = \beta_{ij}(X_k, Z_k)$$

and $$\epsilon_{jk} = y_{jk} - E_{g_j}(y|X_k, Z_k).$$

The methods used herein above can still be applied in this context provided some reasonable form is given for $\beta_{ij}(X_k, Z_k)$. One useful choice is given by:

$$\beta_{ij}(X_k, Z_k)=(\phi_j R(Z_k))_i$$

Where $\Phi_j$ is a 4×m matrix of unknown coefficients and $R(Z_k)$ is a column vector of m elements.

Consider how this would be used to study differences in gene expression among subjects who relapse and those who do not. In this case, $Z_k$ is an indicator variable taking the value zero for samples of subjects who do not relapse and one for those who do. Then $$R(Z_k) = \begin{pmatrix} 1 \\ Z_k \end{pmatrix}$$

and $\Phi_j$ is a four by two matrix of coefficients:

$$\phi_j = \begin{pmatrix} v_{Bj} & \delta_{Bj} \\ v_{Tj} & \delta_{Tj} \\ v_{Sj} & \delta_{Sj} \\ v_{Cj} & \delta_{Cj} \end{pmatrix}$$

Notice that this leads to $$X_k\phi_j R(Z_k) = x_{k,B}v_{Bj} + x_{k,T}v_{Tj} + x_{k,S}v_{Sj} + x_{k,C}v_{Cj} + x_{k,B}Z_k\delta_{Bj} + x_{k,T}Z_k\delta_{Tj} + x_{k,S}Z_k\delta_{Sj} + x_{k,C}Z_k\delta_{Cj}$$

The v coefficients give the average expression of the different cell types in subjects who do not relapse, while the δ coefficients give the difference between the average expression of the different cell types in subjects who do relapse and those who do not. Thus, a non-zero value of $\delta_T$ would indicate that in tumor cells, the average expression level differs for subjects who relapse and those who do not. The above equation is linear in its coefficients, so standard statistical methods can be applied to estimation and inference on the coefficients. Extensions that allow β to depend on both cell proportions and on sample covariates can be determined according to the teachings provided herein or other methods known in the art.

Nucleic Acids

Provided herein are nucleic acid molecules that contain one or more nucleotide sequences provided in SEQ ID NO:1-38,826 or a complement thereof. For purposes of brevity and clarity, reference to one or more nucleotide sequences in SEQ ID NO: 1-38,826 also is intended to refer to the nucleotide sequence complementary thereto, as will be understood by one skilled in the art. In some embodiments, a nucleic acid molecule that contains one or more nucleotide sequences provided in SEQ ID NO:1-38,826 is a gene that encodes RNA and/or a polypeptide. Also provided herein are splice variants of the nucleotide sequences listed in SEQ ID NO:35,580-38,826. Such splice variants also can encode a polypeptide. In particular, nucleic acid molecules encoding genes containing the nucleotide sequences listed in SEQ ID NO:35,580-38,826 from animals, including splice variants thereof are provided. The encoded proteins are also provided. Also provided are functional domains thereof. For each of the nucleic acid molecules provided, the nucleic acid can be DNA or RNA or PNA or other nucleic acid analogs or can include non-natural nucleotide bases. Also provided are isolated nucleic acid molecules that include a sequence of nucleotides complementary to a nucleotide sequence provided in SEQ ID NO:1-38,826. In some embodiments, the nucleotide sequences selected from SEQ ID NO:1-38,826 are selected from SEQ ID NO:35,580-38,826.

Provided herein are tables listing probe sets; nucleotide sequences of the probes in the probe sets; genes associated with the probe set, including, for some tables, genbank accession number, locus ID, nucleotide sequence of the genes, splice regions for the genes, start and stop translation sites for the genes; modified t statistics for each probe set, and additional information described with reference to the individual table. One skilled in the art will recognize the relationship between the tables, such that nucleotide sequence information associated with particular probe sets in a first table can thereby be associated with other features such as modified t statistics by virtue of one or more additional tables that associate probe sets with those features such as modified t statistics. For example, Table 15 lists Probe ID, Probe SEQ ID NOs and Gene SEQ ID NOs to identify the nucleotide sequences of the enclosed sequence listing correspond to each Probe set (Probe ID); subsequent tables (e.g., Table 2 or Table 8) that describe information (e.g., modified t statistics) relating to a particular Probe ID, are therefore contemplated herein to also describe information relating to each nucleotide sequence identified with that Probe ID.

Table 2 provides modified t statistics for an Affymetrix U95Av2 microarray, including Bstat (modified t statistic for BPH), Sstat (modified t statistic for stroma), Tstat (modified t statistic for tumor). The Probe IDs for the U95Av2 microarray that map to a Probe ID for the U133a microarray, and the mapping itself, is provided in Table 17, where the mapping represents Probe IDs of microarrays that can hybridize to the same gene. Probe IDs with identical names for the two arrays are identical. Accordingly, by virtue of the mapping of Table 17, Table 2 Probe IDs can be associated with nucleotide sequences via Table 15. Table 8 provides Probe IDs for Affymetrix U133a microarray, and associated t statistics for BPH, tumor, stroma and cystic atrophy. Table 8 also identifies cell type for which the modified t statistic is greater than 2.5. Table 8 also identifies cell type for which the calculated expression for the associated gene is greater than two-fold more than in other cell types; such information can be used in selection of probes for a classifier, as described elsewhere herein. Table 9 provides the top genes identified as up- and down-regulated in prostate tumor cells of relapse patients, calculated by linear regression including all samples with prostate cancer; in Table 9, "1" is the top up-regulated gene, and "−1" is the top down-regulated gene. The gene(s) referred to in Table 9 (which lists Probe ID) can be determined by way of Table 15. Other tables describing genes in terms of Probe ID also can be interpreted according to Table 15. Tables 9-13 also contains a column that indicates with a "D" those genes that have a greater than 1.5 fold ratio of predicted expression between relapse and non-relapse tissue, as well as an absolute difference in expression that exceeds the expression level reported for most genes queried by the array.

Table 10 provides top genes identified as up- and down-regulated in prostate stroma of relapse patients, calculated by linear regression including all samples with prostate cancer, with numbering as in Table 9. Table 11 identifies exemplary genes whose expression can be examined in methods for identifying or characterizing a sample; and also identifies Probe IDs that can be used for such gene expression identification.

Table 12 provides top 144 genes identified as down-regulated in prostate stroma cells of relapse patients, calculated by linear regression including only samples that did not have detectable tumor cells, with ranking as with Table 9. In some embodiments, Table 13 provides top 100 genes identified as up-regulated in prostate stroma of relapse patients when only samples free of tumor were examined from cases of prostate cancer. Thus, Tables 12 and 13 demonstrate that genes in stroma can be used to determine a prognosis such as relapse, aggressiveness, and indolence of prostate tumor.

Table 15 provides splice variants of the genes provided herein. Each row identifies one or more pairs of numbers that identify the first and last residues of an exon in the gene, where the numbers in the pair are separated by a comma, and different pairs are separated by semicolons. Table 15 also provides the start and stop site of translation of the gene into a polypeptide. As will be understood in the art, multiple splicing combinations are provided for some genes. One skilled in the art can apply the splicing taught in Table 15 and nucleotide sequences listed herein to generate the nucleotide sequence of a spliced mRNA transcript. One skilled in the art also can apply the splicing taught in Table 15 and nucleotide sequences listed herein to generate the amino acid sequence of a polypeptide translated from the spliced transcript. Reference herein to one or more genes (including reference to products of genes) by referring to the SEQ ID NO of the gene or the SEQ ID NO of a nucleotide contained in the gene also contemplates reference to spliced gene sequences for the corresponding SEQ ID NO in accordance with Table 15. Similarly, reference herein to one or more protein gene products also contemplates proteins translated from the splice variants identified in Table 15.

Table 14 provides a list of 35 (nonunique) genes that have been associated with differential expression in aggressive prostate cancer. Among the cell-specific genes identified here (see, e.g., Tables 8-10), those not previously known to be indicator of aggressive prostate cancer are contemplated herein. For example, Table 14 lists genes associated with aggressive prostate cancer that are also found among the genes identified here (see, e.g., Table 9-10). Thus, contemplated herein all genes of Tables 1-13 and 15-17 that are not present in Table 14 represent genes identified herein as genes whose differential expression can be indicative of prostate cancer (in accordance with the corresponding table). For example, cell-specific genes statistically significantly differentially expressed in early relapse prostate cancer by tumor cells (Table 9) or stroma cells (Table 10) of early relapse prostate cancer are biomarkers when used individually or in combination to form panels or profiles of genes for use in the examination of gene expression of prostate tissue by the methods described herein in order to determine whether the examined prostate tissue is similar in gene expression to the pattern of, for example, early relapsed or aggressive disease or indolent disease. When used alone as markers, the methods, compositions and kits provided herein exclude those genes identified in Table 14. When used in combination, genes identified in Table 14 also can be used in the methods, combinations, compositions and kits provided herein, with the exception of use of PSA and PMSA in a combination of only those two genes.

Exemplary, non-limiting examples of genes whose products can be detected in the methods provided herein include, IGF-1, microsimino protein, and MTA-1. In one embodiment detection of the expression of one or more of these genes can be performed in combination with detection of expression of one or more additional genes containing a sequence provided in SEQ ID NO:1-38,826.

Uses of Probes and detection of genes identified in the tables are described herein and exemplified below. It is contemplated herein that uses and methods similar to those exemplified below can be applied to the probe and gene nucleotide sequences in accordance with the teachings provided herein.

Also provided are nucleic acid molecules that have at least 60%, 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity with a nucleotide of SEQ ID NO:1-38,826, or that hybridizes along their full-length or along at least about 70%, 80% or 90% of the full-length nucleic acid to a nucleic acids under conditions of moderate, or high, stringency. In some embodiments, the nucleotide sequences selected from SEQ ID NO:1-38,826 are selected from SEQ ID NO:35,580-38,826.

The isolated nucleic acids can contain least 10 nucleotides, 25 nucleotides, 50 nucleotides, 100 nucleotides, 150 nucleotides, or 200 nucleotides or more, contiguous nucleotides of a sequence provided in SEQ ID NO:1-38,826. In another embodiment, the nucleic acids are smaller than 35, 200 or 500 nucleotides in length. In some embodiments, the nucleotide sequences selected from SEQ ID NO:1-38,826 are selected from SEQ ID NO:35,580-38,826.

Also provided are fragments of the above nucleic acids that can be used as probes or primers and that contain at least about 10 nucleotides, at least about 14 nucleotides, at least about 16 nucleotides, or at least about 30 nucleotides. The length of the probe or primer is a function of the size of the genome probed; the larger the genome, the longer the probe or primer required for specific hybridization to a single site. Those of skill in the art can select appropriately sized probes and primers. Probes and primers as described can be single-stranded. Double stranded probes and primers also can be used, if they are denatured when used. Probes and primers derived from the nucleic acid molecules are provided. Such probes and primers contain at least 8, 14, 16, 30, 100 or more contiguous nucleotides. The probes and primers are optionally labeled with a detectable label, such as a radiolabel or a fluorescent tag, or can be mass differentiated for detection by mass spectrometry or other means. Also provided is an isolated nucleic acid molecule that includes the sequence of molecules that is complementary to the nucleotides provided in SEQ ID NO:1-38,826. Double-stranded RNA (dsRNA), such as RNAi is also provided. In some embodiments, the nucleotide sequences selected from SEQ ID NO:1-38,826 are selected from SEQ ID NO:35,580-38,826.

Plasmids and vectors containing the nucleic acid molecules are also provided. Cells containing the vectors, including cells that express the encoded proteins are provided. The cell can be a bacterial cell, a yeast cell, a fungal cell, a plant cell, an insect cell or an animal cell.

For recombinant expression of one or more of the genes containing a nucleotide sequence provided in SEQ ID NO:1-38,826, the nucleic acid containing all or a portion of the nucleotide sequence encoding the genes can be inserted into an appropriate expression vector, i.e., a vector that contains the elements for the transcription and translation of the inserted protein coding sequence. In some embodiments, the nucleotide sequences selected from SEQ ID NO:1-38,826 are selected from SEQ ID NO:35,580-38,826. The transcriptional and translational signals can also be supplied by the native promoter for the genes, and/or their flanking regions.

Also provided are vectors that contain nucleic acid encoding a gene containing a sequence provided in SEQ ID NO:1-38,826 In some embodiments, the nucleotide sequences selected from SEQ ID NO:1-38,826 are selected from SEQ ID NO:35,580-38,826. Cells containing the vectors are also provided. The cells include eukaryotic and prokaryotic cells, and the vectors are any suitable for use therein.

Prokaryotic and eukaryotic cells containing the vectors are provided. Such cells include bacterial cells, yeast cells, fungal cells, plant cells, insect cells and animal cells. The cells can be used to produce an oligonucleotide or polypeptide gene products by (a) growing the above-described cells under conditions whereby the encoded gene is expressed by the cell, and then (b) recovering the expressed compound.

A variety of host-vector systems can be used to express the protein coding sequence. These include but are not limited to mammalian cell systems infected with virus (e.g. vaccinia virus, adenovirus, etc.); insect cell systems infected with virus (e.g. baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system used, any one of a number of suitable transcription and translation elements can be used.

Any methods known to those of skill in the art for the insertion of nucleic acid fragments into a vector can be used to construct expression vectors containing a chimeric gene containing appropriate transcriptional/translational control signals and protein coding sequences. These methods can include in vitro recombinant DNA and synthetic techniques and in vivo recombinants (genetic recombination). Expression of nucleic acid sequences encoding polypeptide can be regulated by a second nucleic acid sequence so that the genes or fragments thereof are expressed in a host transformed with the recombinant DNA molecule(s). For example, expression of the proteins can be controlled by any promoter/enhancer known in the art.

Proteins

Protein products of the genes provided in SEQ ID NO:35, 580-38,826, derivatives and analogs can be produced by various methods known in the art. For example, once a recombinant cell expressing such a polypeptide, or a domain, fragment or derivative thereof, is identified, the individual gene product can be isolated and analyzed. This is achieved by assays based on the physical and/or functional properties of the protein, including, but not limited to, radioactive labeling of the product followed by analysis by gel electrophoresis, immunoassay, cross-linking to marker-labeled product, and assays of protein activity or antibody binding.

The polypeptides can be isolated and purified by standard methods known in the art (either from natural sources or recombinant host cells expressing the complexes or proteins), including but not restricted to column chromatography (e.g., ion exchange, affinity, gel exclusion, reversed-phase high pressure and fast protein liquid), differential centrifugation, differential solubility, or by any other standard technique used for the purification of proteins. Functional properties can be evaluated using any suitable assay known in the art.

Manipulations of polypeptide sequences can be made at the protein level. Also contemplated herein are polypeptide proteins, domains thereof, derivatives or analogs or fragments thereof, which are differentially modified during or after translation, e.g., by glycosylation, acetylation, phosphorylation, amidation, derivatization by known protecting/blocking groups, proteolytic cleavage, linkage to an antibody molecule or other cellular ligand. Any of numerous chemical modifications can be carried out by known techniques, including but not limited to specific chemical cleavage by cyanogen bromide, trypsin, chymotrypsin, papain, V8 protease, NaBH4, acetylation, formulation, oxidation, reduction, metabolic synthesis in the presence of tunicamycin and other such agents.

In addition, domains, analogs and derivatives of a polypeptide provided herein can be chemically synthesized. For example, a peptide corresponding to a portion of a polypeptide provided herein, which includes the desired domain or which mediates the desired activity in vitro can be synthesized by use of a peptide synthesizer. Furthermore, if desired, nonclassical amino acids or chemical amino acid analogs can be introduced as a substitution or addition into the polypeptide sequence. Non-classical amino acids include but are not limited to the D-isomers of the common amino acids, a-amino isobutyric acid, 4-aminobutyric acid, Abu, 2-aminobutyric acid, .epsilon.-Abu, e-Ahx, 6-amino hexanoic acid, Aib, 2-amino isobutyric acid, 3-amino propionoic acid, ornithine, norleucine, norvaline, hydroxyproline, sarcosine, citrulline, cysteic acid, t-butylglycine, t-butylalanine, phenylglycine, cyclohexylalanine, .beta.-alanine, fluoro-amino acids, designer amino acids such as .beta.-methyl amino acids, Ca-methyl amino acids, Na-methyl amino acids, and amino acid analogs in general. Furthermore, the amino acid can be D (dextrorotary) or L (levorotary).

Screening Methods

The oligonucleotide or polypeptide gene products provided herein can be used in a variety of methods to identify compounds that modulate the activity thereof. As provided herein, the nucleotide sequences and genes identified in SEQ ID NO:35,580-38,826 can be identified in different cell types and in the same cell type in which subject have different phenotypes. Methods are provided herein for screening compounds can include contacting cells with a compound and measuring gene expression levels, wherein a change in expression levels relative to a reference identifies the compound as a compound that modulates a gene expression.

Also provided herein are methods for identification and isolation of agents, such as compounds that bind to products of genes identified in SEQ ID NO:35,580-38,826. The assays are designed to identify agents that bind to the RNA or polypeptide gene product. The identified compounds are candidates or leads for identification of compounds for treatments of tumors and other disorders and diseases.

A variety of methods can be used, as known in the art. These methods can be performed in solution or in solid phase reactions.

Methods for identifying an agent, such as a compound, that specifically binds to an oligonucleotide or polypeptide encoded by a gene identified in SEQ ID NO:35,580-38,826 are provided herein. The method can be practiced by (a) contacting the gene product with one or a plurality of test agents under conditions conducive to binding between the gene product and an agent; and (b) identifying one or more agents within the one or plurality that specifically binds to the gene product. Compounds or agents to be identified can originate from biological samples or from libraries, including, but are not limited to, combinatorial libraries. Exemplary libraries can be fusion-protein-displayed peptide libraries in which random peptides or proteins are presented on the surface of phage particles or proteins expressed from plasmids; support-bound synthetic chemical libraries in which individual compounds or mixtures of compounds are presented on insoluble matrices, such as resin beads, or other libraries known in the art.

Modulators of the Activity of Gene products

Provided herein are compounds that modulate the activity of a gene product from SEQ ID NO:35,580-38,826. These compounds act by directly interacting with the polypeptide or by altering transcription or translation thereof. Such molecules include, but are not limited to, antibodies that specifically bind the polypeptide, antisense nucleic acids or double-stranded RNA (dsRNA) such as RNAi, that alter expression of the polypeptide, antibodies, peptide mimetics and other such compounds.

Antibodies, including polyclonal and monoclonal antibodies, that specifically bind to a polypeptide gene product provided herein are provided. The antibody can be a monoclonal antibody, and the antibody can specifically bind to the polypeptide. The polypeptide and domains, fragments, homologs and derivatives thereof can be used as immunogens to generate antibodies that specifically bind such immunogens. Such antibodies include but are not limited to polyclonal, monoclonal, chimeric, single chain, Fab fragments, and an Fab expression library. In a specific embodiment, antibodies to human polypeptides are produced. Methods for monoclonal and polyclonal antibody production are known in the art. Antibody fragments that specifically bind to the polypeptide or epitopes thereof can be generated by techniques known in the art. For example, such fragments include but are not limited to: the F(ab')2 fragment, which can be produced by pepsin digestion of the antibody molecule; the Fab' fragments that can be generated by reducing the disulfide bridges of the F(ab')2 fragment, the Fab fragments that can be generated by treating the antibody molecular with papain and a reducing agent, and Fv fragments.

Peptide analogs are commonly used in the pharmaceutical industry as non-peptide drugs with properties analogous to those of the template peptide. These types of non-peptide compounds are termed peptide mimetics or peptidomimetics (Luthman et al., A Textbook of Drug Design and Development, 14:386-406, 2nd Ed., Harwood Academic Publishers (1996); Joachim Grante (1994) Angew. Chem. Int. Ed. Engl., 33:1699-1720; Fauchere (1986) J. Adv. Drug Res., 15:29; Veber and Freidinger (1985) TINS, p. 392; and Evans et al. (1987) J. Med. Chem. 30:1229). Peptide mimetics that are structurally similar to therapeutically useful peptides can be used to produce an equivalent or enhanced therapeutic or prophylactic effect. Preparation of peptidomimetics and structures thereof are known to those of skill in this art.

Prognosis and Diagnosis

Products of genes in SEQ ID NO:35,580-38,826 can be detected in diagnostic methods, such as diagnosis of tumors and other diseases or disorders. Such methods can be used to detect, prognose, diagnose, or monitor various conditions, diseases, and disorders. Exemplary compounds that can be used in such detection methods include polypeptides such as antibodies or fragments thereof that specifically bind polypeptides encoded by the genes of SEQ ID NO:35,580-38,826, and oligonucleotides such as DNA probes or primers that specifically bind oligonucleotides such as RNA encoded by the genes of SEQ ID NO:35,580-38,826.

A set of one or more, or two or more compounds for detection of markers containing a nucleotide sequence provided in SEQ ID NO:1-38,826, complements thereof, fragments thereof, or polypeptides encoded thereby, can be selected for any of a variety of assay methods provided herein. For example, one or more, or two or more such compounds can be selected as diagnostic or prognostic indicators. Methods for selecting such compounds and using such compounds in assay methods such as diagnostic and prognostic indicator applications are known in the art. For example, the Tables provided herein list a modified t statistic associated with each marker, where the modified t statistic indicate the ability of the associated marker to indicate (by presence or absence of the marker, according to the modified t statistic) the presence or absence of a particular cell type in a prostate sample.

In another embodiment, marker selection can be performed by considering both modified t statistics and expected intensity of the signal for a particular marker. For example, markers can be selected that have a strong signal in a cell type whose presence or absence is to be determined, and also have a sufficiently large modified t statistic for gene expression in that cell type. Also, markers can be selected that have little or no signal in a cell type whose presence or absence is to be determined, and also have a sufficiently large negative modified t statistic for gene expression in that cell type.

Exemplary assays include immunoassays such as competitive and non-competitive assay systems using techniques such as western blots, radioimmunoassays, ELISA (enzyme linked immunosorbent assay), sandwich immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays. Other exemplary assays include hybridization assays which can be carried out by a method by contacting a sample containing nucleic acid with a nucleic acid probe, under conditions such that specific hybridization can occur, and detecting or measuring any resulting hybridization.

Kits for diagnostic use are also provided, that contain in one or more containers an anti-polypeptide antibody, and, optionally, a labeled binding partner to the antibody. A kit is also provided that includes in one or more containers a nucleic acid probe capable of hybridizing to the gene-encoding nucleic acid. In a specific embodiment, a kit can include in one or more containers a pair of primers (e.g., each in the size range of 6-30 nucleotides) that are capable of priming amplification. A kit can optionally further include in a container a predetermined amount of a purified control polypeptide or nucleic acid.

The kits can contain packaging material that is one or more physical structures used to house the contents of the kit, such as invention nucleic acid probes or primers, and the like. The packaging material is constructed by well known methods, and can provide a sterile, contaminant-free environment. The packaging material has a label which indicates that the compounds can be used for detecting a particular oligonucleotide or polypeptide. The packaging materials employed herein in relation to diagnostic systems are those customarily utilized in nucleic acid or protein-based diagnostic systems. A package is to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed. The kits also can include instructions for use, which can include a tangible expression describing the reagent concentration or at least one assay method parameter, such as the relative amounts of reagent and sample to be admixed, maintenance time periods for reagent/sample admixtures, temperature, buffer conditions, and the like.

Pharmaceutical Compositions and Modes of Administration

Pharmaceutical compositions containing the identified compounds that modulate expression of a gene in SEQ ID NO:35,580-38,826 or bind to a gene product are provided herein. Also provided are combinations of such a compound and another treatment or compound for treatment of a disease or disorder, such as a chemotherapeutic compound.

Expression modulator or binding compound and other compounds can be packaged as separate compositions for administration together or sequentially or intermittently. Alternatively, they can provided as a single composition for administration or as two compositions for administration as a single composition. The combinations can be packaged as kits.

Compounds and compositions provided herein can be formulated as pharmaceutical compositions, for example, for single dosage administration. The concentrations of the compounds in the formulations are effective for delivery of an amount, upon administration, that is effective for the intended treatment. In certain embodiments, the compositions are formulated for single dosage administration. To formulate a composition, the weight fraction of a compound or mixture thereof is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds can be formulated as the sole pharmaceutically active ingredient in the composition or can be combined with other active ingredients. The active compound is included in the pharmaceutically acceptable carrier in an amount sufficient to exert a therapeutically useful effect in the absence of undesirable side effects on the subject treated. The therapeutically effective concentration can be determined empirically by testing the compounds in known in vitro and in vivo systems. The concentration of active compound in the drug composition depends on absorption, inactivation and excretion rates of the active compound, the physicochemical characteristics of the compound, the dosage schedule, and amount administered as well as other factors known to those of skill in the art. Pharmaceutically acceptable derivatives include acids, salts, esters, hydrates, solvates and prodrug forms. The derivative can be selected such that its pharmacokinetic properties are superior to the corresponding neutral compound. Compounds are included in an amount effective for ameliorating or treating the disorder for which treatment is contemplated.

Formulations suitable for a variety of administrations such as perenteral, intramuscular, subcutaneous, alimentary, transdermal, inhaling and other known methods of administration, are known in the art. The pharmaceutical compositions can also be administered by controlled release means and/or delivery devices as known in the art. Kits containing the compositions and/or the combinations with instructions for administration thereof are provided. The kit can further include a needle or syringe, which can be packaged in sterile form, for injecting the complex, and/or a packaged alcohol pad. Instructions are optionally included for administration of the active agent by a clinician or by the patient.

The compounds can be packaged as articles of manufacture containing packaging material, a compound or suitable derivative thereof provided herein, which is effective for treatment of a diseases or disorders contemplated herein, within the packaging material, and a label that indicates that the compound or a suitable derivative thereof is for treating the diseases or disorders contemplated herein. The label can optionally include the disorders for which the therapy is warranted.

Methods of Treatment

The compounds provided herein can be used for treating or preventing diseases or disorders in an animal, such as a mammal, including a human. In one embodiment, the method includes administering to a mammal an effective amount of a compound that modulates the expression of a gene provided in SEQ ID NO:35,580-38,826 or a compound that binds to a product of a gene provided in SEQ ID NO:35,580-38,826, whereby the disease or disorder is treated or prevented. Exemplary inhibitors provided herein are those identified by the screening assays. In addition, antibodies and antisense nucleic acids or double-stranded RNA (dsRNA), such as RNAi, are contemplated.

In a specific embodiment, as described hereinabove, gene expression can be inhibited by antisense nucleic acids. The therapeutic or prophylactic use of nucleic acids of at least six nucleotides, up to about 150 nucleotides, that are antisense to a gene or cDNA is provided. The antisense molecule can be complementary to all or a portion of the gene. For example, the oligonucleotide is at least 10 nucleotides, at least 15 nucleotides, at least 100 nucleotides, or at least 125 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide can include other appending groups such as peptides, or agents facilitating transport across the cell membrane, hybridization-triggered cleavage agents or intercalating agents.

RNA interference (RNAi) (see, e.g. Chuang et al. (2000) Proc. Natl. Acad. Sci. U.S.A. 97:4985) can be employed to inhibit the expression of a gene provided in SEQ ID NO:35, 580-38,826. Interfering RNA (RNAi) fragments, such as double-stranded (ds) RNAi, can be used to generate loss-of-gene function. Methods relating to the use of RNAi to silence genes in organisms including, mammals, C. elegans, Drosophila and plants, and humans are known. Double-stranded RNA (dsRNA)-expressing constructs are introduced into a host, such as an animal or plant using, a replicable vector that remains episomal or integrates into the genome. By selecting appropriate sequences, expression of dsRNA can interfere with accumulation of endogenous mRNA. RNAi also can be used to inhibit expression in vitro. Regions include at least about 21 (or 21) nucleotides that are selective (i.e. unique) for the selected gene are used to prepare the RNAi. Smaller fragments of about 21 nucleotides can be transformed directly (i.e., in vitro or in vivo) into cells; larger RNAi dsRNA molecules can be introduced using vectors that encode them. dsRNA molecules are at least about 21 bp long or longer, such as 50, 100, 150, 200 and longer. Methods, reagents and protocols for introducing nucleic acid molecules in to cells in vitro and in vivo are known to those of skill in the art.

In an exemplary embodiment, nucleic acids that include a sequence of nucleotides encoding a polypeptide of a gene provided in SEQ ID NO:35,580-38,826, are administered to promote polypeptide function, by way of gene therapy. Gene therapy refers to therapy performed by the administration of a nucleic acid to a subject. In this embodiment, the nucleic acid produces its encoded protein that mediates a therapeutic effect by promoting polypeptide function. Any of the methods for gene therapy available in the art can be used (see, Goldspiel et al., Clinical Pharmacy 12:488-505 (1993); Wu and Wu, Biotherapy 3:87-95 (1991); Tolstoshev, An. Rev. Pharmacol. Toxicol. 32:573-596 (1993); Mulligan, Science 260:926-932 (1993); and Morgan and Anderson, An. Rev. Biochem. 62:191-217 (1993); TIBTECH 11 (5):155-215 (1993).

In one embodiment, vaccines based on the genes and polypeptides provided herein can be developed. For example genes can be administered as DNA vaccines, either single genes or combinations of genes. Naked DNA vaccines are generally known in the art. Methods for the use of genes as DNA vaccines are well known to one of ordinary skill in the art, and include placing a gene or portion of a gene under the control of a promoter for expression in a patient with cancer. The gene used for DNA vaccines can encode full-length proteins, but can encode portions of the proteins including peptides derived from the protein. For example, a patient can be immunized with a DNA vaccine comprising a plurality of nucleotide sequences derived from a particular gene. In another embodiment, it is possible to immunize a patient with a plurality of genes or portions thereof. Without being bound by theory, expression of the polypeptide encoded by the DNA vaccine, cytotoxic T-cells, helper T-cells and antibodies are induced that recognize and destroy or eliminate cells expressing the proteins provided herein.

DNA vaccines include a gene encoding an adjuvant molecule with the DNA vaccine. Such adjuvant molecules include cytokines that increase the immunogenic response to the polypeptide encoded by the DNA vaccine. Additional or alternative adjuvants are known to those of ordinary skill in the art and find use in the invention.

Animal Models and Transgenics

Also provided herein, the nucleotide the genes, nucleotide molecules and polypeptides disclosed herein find use in generating animal models of cancers, such as lymphomas and carcinomas. As is appreciated by one of ordinary skill in the art, when one of the genes provided herein is repressed or diminished, gene therapy technology wherein antisense RNA directed to the gene will also diminish or repress expression of the gene. An animal generated as such serves as an animal model that finds use in screening bioactive drug candidates. In another embodiment, gene knockout technology, for example as a result of homologous recombination with an appropriate gene targeting vector, will result in the absence of the protein. When desired, tissue-specific expression or knockout of the protein can be accomplished using known methods.

It is also possible that the protein is overexpressed in cancer. As such, transgenic animals can be generated that overexpress the protein. Depending on the desired expression level, promoters of various strengths can be employed to express the transgene. Also, the number of copies of the integrated transgene can be determined and compared for a determination of the expression level of the transgene. Animals generated by such methods find use as animal models and are additionally useful in screening for bioactive molecules to treat cancer.

Computer Programs and Methods

The various techniques, methods, and aspects of the methods provided herein can be implemented in part or in whole using computer-based systems and methods. In another embodiment, computer-based systems and methods can be used to augment or enhance the functionality described above, increase the speed at which the functions can be performed, and provide additional features and aspects as a part of or in addition to those of the invention described elsewhere in this document. Various computer-based systems, methods and implementations in accordance with the above-described technology are presented below.

A processor-based system can include a main memory, such as random access memory (RAM), and can also include a secondary memory. The secondary memory can include, for example, a hard disk drive and/or a removable storage drive, representing a floppy disk drive, a magnetic tape drive, an optical disk drive, etc. The removable storage drive reads from and/or writes to a removable storage medium. Removable storage medium refers to a floppy disk, magnetic tape, optical disk, and the like, which is read by and written to by a removable storage drive. As will be appreciated, the removable storage medium can comprise computer software and/or data.

In alternative embodiments, the secondary memory may include other similar means for allowing computer programs or other instructions to be loaded into a computer system. Such means can include, for example, a removable storage unit and an interface. Examples of such can include a program cartridge and cartridge interface (such as the found in video game devices), a movable memory chip (such as an EPROM or PROM) and associated socket, and other removable storage units and interfaces, which allow software and data to be transferred from the removable storage unit to the computer system.

The computer system can also include a communications interface. Communications interfaces allow software and data to be transferred between computer system and external devices. Examples of communications interfaces can include a modem, a network interface (such as, for example, an Ethernet card), a communications port, a PCMCIA slot and card, and the like. Software and data transferred via a communications interface are in the form of signals, which can be electronic, electromagnetic, optical or other signals capable of being received by a communications interface. These signals are provided to communications interface via a channel capable of carrying signals and can be implemented using a wireless medium, wire or cable, fiber optics or other communications medium. Some examples of a channel can include a phone line, a cellular phone link, an RF link, a network interface, and other communications channels.

In this document, the terms computer program medium and computer usable medium are used to refer generally to media such as a removable storage device, a disk capable of installation in a disk drive, and signals on a channel. These computer program products are means for providing software or program instructions to a computer system.

Computer programs (also called computer control logic) are stored in main memory and/or secondary memory. Computer programs can also be received via a communications interface. Such computer programs, when executed, permit the computer system to perform the features of the invention as discussed herein. In particular, the computer programs, when executed, permit the processor to perform the features of the invention. Accordingly, such computer programs represent controllers of the computer system.

In an embodiment where the elements are implemented using software, the software may be stored in, or transmitted via, a computer program product and loaded into a computer system using a removable storage drive, hard drive or communications interface. The control logic (software), when executed by the processor, causes the processor to perform the functions of the invention as described herein.

In another embodiment, the elements are implemented in hardware using, for example, hardware components such as PALs, application specific integrated circuits (ASICs) or other hardware components. Implementation of a hardware state machine so as to perform the functions described herein will be apparent to person skilled in the relevant art(s). In yet another embodiment, elements are implanted using a combination of both hardware and software.

In another embodiment, the computer-based methods can be accessed or implemented over the World Wide Web by providing access via a Web Page to the methods of the invention. Accordingly, the Web Page is identified by a Universal Resource Locator (URL). The URL denotes both the server machine and the particular file or page on that machine. In this embodiment, it is envisioned that a consumer or client computer system interacts with a browser to select a particular URL, which in turn causes the browser to send a request for that URL or page to the server identified in the URL. The server can respond to the request by retrieving the requested page and transmitting the data for that page back to the requesting client computer system (the client/server interaction can be performed in accordance with the hypertext transport protocol (HTTP)). The selected page is then displayed to the user on the client's display screen. The client may then cause the server containing a computer program of the invention to launch an application to, for example, perform an analysis according to the methods provided herein.

Prostate-Associated Genes

Provided herein are probe and gene sequences that can be indicative of the presence and/or absence of prostate cancer in a subject. Also provided herein are probe and gene sequences that can be indicative of presence and/or absence of benign prostatic hyperplasia (BPH) in a subject. Also provided herein are probe and gene sequences that can be indicative of a prognosis of prostate cancer, where such a prognosis can include likely relapse of prostate cancer, likely aggressiveness of prostate cancer, likely indolence of prostate cancer, likelihood of survival of the subject, likelihood of success in treating prostate cancer, condition in which a particular treatment regimen is likely to be more effective than another treatment regimen, and combinations thereof. In one embodiment, the probe and gene sequences can be indicative of the likely aggressiveness or indolence of prostate cancer.

As provided in the methods and Tables herein, probes have been identified that hybridize to one or more nucleic acids of a prostate sample at different levels according to the presence or absence of prostate tumor, BPH and stroma in the sample. The probes provided herein are listed in conjunction with modified t statistics that represent the ability of that particular probe to indicate the presence or absence of a particular cell type in a prostate sample. Use of modified t statistics for such a determination is described elsewhere herein, and general use of modified t statistics is known in the art. Accordingly, provided herein are nucleotide sequences of probes that can be indicative of the presence or absence of prostate tumor and/or BPH cells, and also can be indicative of the likelihood of prostate tumor relapse in a subject.

Also provided in the methods and Tables herein are nucleotide and predicted amino acid sequences of genes and gene products associated with the probes provided herein. Accordingly, as provided herein, detection of gene products (e.g., mRNA or protein) or other indicators of gene expression, can be indicative of the presence or absence of prostate tumor and/or BPH cells, and also can be indicative of the likelihood of prostate tumor relapse in a subject. As with the probe sequences, the nucleotide and amino acid sequences of these gene products are listed in conjunction with modified t statistics that represent the ability of that particular gene product or indicator thereof to indicate the presence or absence of a particular cell type in a prostate sample.

Methods for determining the presence of prostate tumor and/or BPH cells, the likelihood of prostate tumor relapse in a subject, the likelihood of survival of prostate cancer, the aggressiveness of prostate tumor, the indolence of prostate tumor, survival, and other prognoses of prostate tumor, can be performed in accordance with the teachings and examples provided herein. Also provided herein, a set of probes or gene products can be selected according to their modified t statistic for use in combination (e.g., for use in a microarray) in methods of determining the presence of prostate tumor and/or BPH cells, and/or the likelihood of prostate tumor relapse in a subject.

Also provided herein, the gene products identified as present at increased levels in prostate cancer or in subjects with likely relapse of cancer, can serve as targets for therapeutic compounds and methods. For example an antibody or siRNA targeted to a gene product present at increased levels in prostate cancer can be administered to a subject to decrease the levels of that gene product and to thereby decrease the malignancy of tumor cells, the aggressiveness of a tumor, indolence of a tumor, survival, or the likelihood of tumor relapse. Methods for providing molecules such as antibodies or siRNA to a subject to decrease the level of gene product in a subject are provided herein or are otherwise known in the art.

In another embodiment, the gene products identified as present at decreased levels in prostate cancer or in subjects with likely relapse of cancer, can serve as subjects for therapeutic compounds and methods. For example a nucleic acid molecule, such as a gene expression vector encoding a particular gene, can be administered to a individual with decreased levels of the particular gene product to increase the levels of that gene product and to thereby decrease the malignancy of tumor cells, the aggressiveness of a tumor, indolence of a tumor, likelihood of survival, or the likelihood of tumor relapse. Methods for providing gene expression vectors to a subject to increase the level of gene product in a subject are provided herein or are otherwise known in the art.

The following examples are included for illustrative purposes only and are not intended to limit the scope of the invention.

EXAMPLES

Example 1

Tissue Samples. Prostate samples were obtained from patients that were preoperatively staged as having organ-confined prostate cancer. Institutional Review Board-approved informed consent for participation in this project was obtained from all patients. Tissue samples were collected in the operating room, and specimens were immediately transported to institutional pathologists who provided fresh portions of grossly identifiable or suspected tumor tissue and separate portions of uninvolved tissues. All tissue was snap frozen upon receipt and maintained in liquid nitrogen until used for frozen section preparation at −22° C. Thirty-eight of the contributed cases contained carcinomas. An additional 50 additional samples, consisting of paired adjacent nontumor tissue and separate nontumor bearing cases, also were used, making a total of 88 specimens for analysis. Tissue for expression analysis was provided as 20-µm-thick serial cryosections sections.

Tissue samples for expression analysis were prepared as 10- to 400-mm$^3$ pieces, an amount that was found to be sufficient to yield 10 µg or more of total RNA. Before RNA preparation, 5-µm frozen sections were prepared at −22° C. The first section and a section every 200 µm thereafter were stained with hematoxylin and eosin for histopathological assessment, and all other intervening sections were prepared at 20-µm thickness for RNA extraction. Typically four to eight thin sections were examined per specimen by four pathologists. Preparative (20-µm) sections were lysed in RNA extraction buffer (RNeasy, Qiagen, Valencia, Calif.) and stored at −80° C. Thin sections were examined by four pathologists in a single session using a multihead microscope. Each pathologist assessed each specimen and completed a standardized form indicating the fraction of total area of the section occupied by the aggregate of all prostate carcinoma cells, benign prostatic hypertrophy (BPH) epithelial cells, dilated gland (dilated cystic atrophy) epithelial cells, and stromal cells. Clear spaces of glandular lumina, edema, defects, etc., were not considered, and minor proportions of neural, vascular, or other components were marked as other (median value, 3.1%). Average percentages of estimates from the four pathologists were calculated for epithelial cells of tumor, BPH, and cystic glands and total stromal cells for each sample.

Data Collection. Preoperative and follow-up demographic and clinical variables, histologic scoring, and DNA array data were collected into an internet accessible, secure Oracle database. Each physical object in the study was issued a unique identifier, and relationships between samples, subsamples, patients, and data were maintained.

Amplification and GeneChip Hybridization. Total cellular RNA was isolated by using RNeasy kits (Qiagen) and quantified by RiboGreen fluorescent assay (Molecular Probes, Eugene, Oreg.), and the quality of preparation was examined by using a BioAnalyzer 2100 (Agilent Technologies, Palo Alto, Calif.). Generation of cRNA was performed according to the known Affymetrix protocol. Briefly, double stranded cDNA was synthesized from total RNA by using a reverse transcriptase with a purified oligo(dT) primer containing a RNA polymerase promoter sequence at it's 5'-end. The second cDNA strand was synthesized using DNA polymerase I, RNase H and DNA ligase. The double-stranded cDNA was placed in RNase-free buffer. Labeled cRNA was generated from cDNA by in vitro transcription and incorporating biotinylated nucleotides. Fifteen micrograms of the resulting biotinylated cRNA was fragmented and hybridized to U95Av2 GeneChip® arrays Affymetrix according to the manufacturer's instructions.

Data Analysis. Array images (.dat files) were digitized by using MAS version 5 (Affymetrix). Gene expression values were generated from the resulting raw numerical data (.cel files) by the dCHIP program of Li and Wong (Li and Wong, Proc. Natl. Acad. Sci. USA 98, 31-36, 2001). Most subsequent analyses were carried out by using the R environment and language including the gee-library for generalized estimated equations (Iheka and Gentleman, J. Comput. Graph. Stat. 5, 299-314, 1996; Zeger and Liang, Biometrics 42, 121-130, 1986). Differential expression between dichotomous variables (tumor/no tumor) was detected by a modification of the permutation method in Efron et al. (J. Am. Stat. Assoc. 96, 1151-1160, 2001). Class predictive genes were identified via the nearest shrunken centroids method by using the PAM package of R software (Tibshirani et al. Proc. Natl. Acad. Sci. USA 99, 6567-6572, 2002).

Immunohistochemistry. Selected gene expression results were validated by the direct examination of the distribution of the protein in paraffin sections of five or more of the cases. Indirect immunohistochemistry was performed. The antibodies were obtained and used as follows: directed against desmin and prostate-specific membrane antigen (PSMA) (DAKO, Carpinteria, Calif.), keratin 15 and tubulin β4 (Neo-Markers, Lab Vision Corporation, Fremont, Calif.), prostaglandin-D2 synthase (Cayman Chemical, Ann Arbor, Mich.), and prostate-specific antigen (PSA) (Biodesign International, Saco, Me.).

Laser Capture Microdissection (LCM). Microdissection of freshly prepared frozen sections was performed by using an Arcturus (Mountain View, Calif.) Mark PixCell II LCM apparatus to isolate prostate cancer epithelium, stroma, and hypertrophic benign epithelial prostate cells. Total RNA was prepared from these samples and used in quantitative RT-PCR (qPCR) to validate cell-specific expression analysis as described in detail together with the gene list, primers, graphical relationships of Affymetrix (modified t statistic) to LCM (LCM/qPCR endpoint). From each flash-frozen tissue, 5-μm-thick frozen sections were prepared. Sections were subsequently dehydrated in graded ethanol solutions (70% once, 5-second rinse, 95% twice, 5-second rinse each, 100% two times, 5-second rinse each) and cleared in xylene (two times, 5 min each). After air-drying for 10 min, the PixCell II LCM System from Acturus Engineering (Mountain View, Calif.) was used for laser capture following the manufacturer's protocol. Total RNA was extracted using resin spin-column system (PicoPure RNA isolation kit, Arcturus Engineering).

Figure 2:
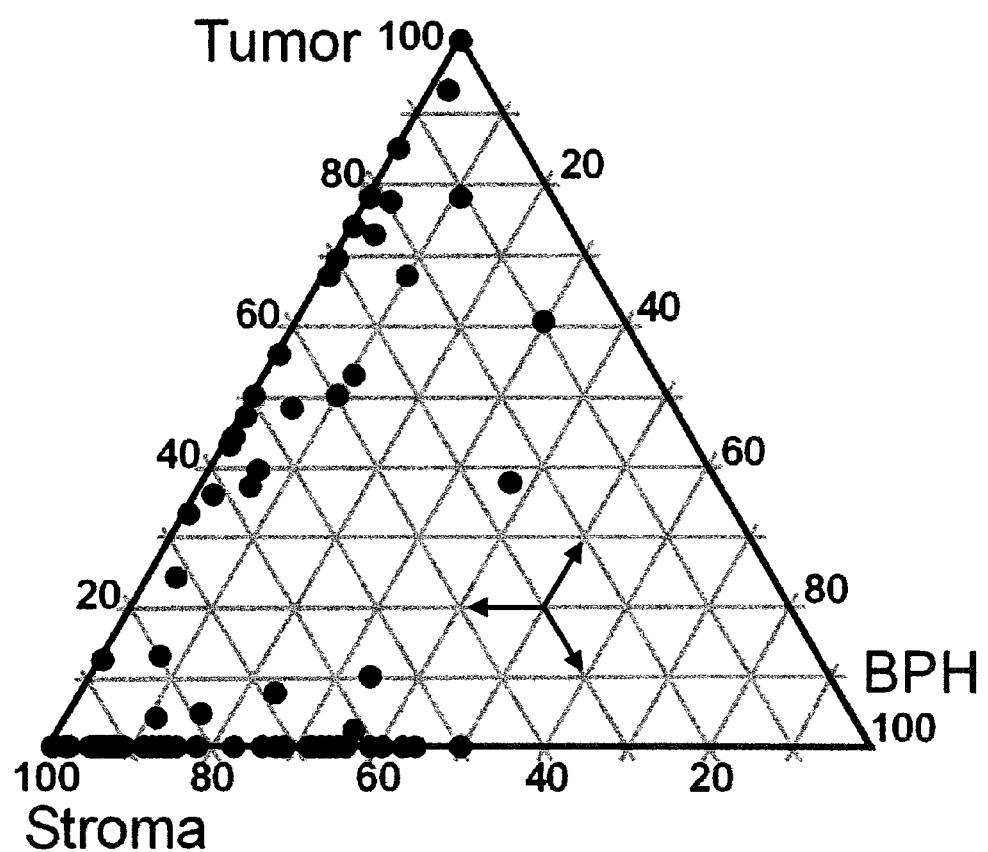
FIG. 2 shows a ternary graph of sample characteristics. Eighty-eight prostatectomy samples from 41 individuals comprising 50 nontumor and 38 tumor-containing specimens were scored for proportional content of tumor, BPH, stroma, and dilated cystic glands. Vertices represent pure tissue types. Epithelia of dilated cystic glands, nerves, and vessels are small components. Note the wide range of proportions of tumor and stromal cells. Estimated tumor percentages ranged from 0.3% through 100%. The proportions were used in the linear models ($x_{kj}$ in Equation 1) for cell-associated gene expression.

The 88 tissue samples from 41 subjects undergoing prostatectomy for clinically early stage localized prostate carcinoma were independently scored by a panel of four pathologists for fractional composition of the four cell types. Agreement analysis on the continuous measures of fractional cell type as estimated by four pathologists were assessed as interobserver Pearson correlation coefficients. The average coefficients for tumor, stroma, BPH, and dilated gland cells were 0.92, 0.77, 0.73, and 0.49, respectively, indicating reproducibility of scoring for the predominant cell types. The lesser reproducibility for the dilated gland category was due to the relative paucity of this cell type in the samples (median proportion=5%). The samples were found to contain a wide range of relative tumor cell numbers ranging, in the case of tumor cells, from a low of 0.3% to a high of 100% tumor cells (FIG. 2).

Despite inclusion of samples with very low tumor content, some 1,197 genes were identified as differentially expressed between tumor and nontumor samples (posterior probability >0.95, see supporting information) according to empirical Bayes estimates. Because tumor samples contained, on average, 53.4% cells of epithelial origin (tumor, BPH, dilated glands), and nontumor samples had an average epithelial composition of 24.7% (P=3.5×10-11), differences in gene expression reflected stromal content were suspected. An illustrative subset of transcripts differentially expressed according to class was identified through nearest shrunken centroids discriminant analysis. Of 37 highly discriminant genes, 23 were predictive of nontumor and were mostly archetypal smooth muscle transcripts such as myosin, tropomyosin, actin, and others. Thus, a corollary notion is that tumor markers identified through standard microarray studies may have little significance with respect to tumor-cell biology, being more reflective of fundamental differences between cells of epithelial versus mesenchymal lineage.

To assign gene expression to particular cell types within tumor specimens, a linear model was constructed in which it was assumed that the contribution to gene expression of any one cell type depends only on the proportion of that cell type and its corresponding characteristic cell-type expression level, $\beta_{ij}$, but not on the proportions of other cell types present. In Equation 1, the average expression level $G_{jk}$ of gene j in a sample k is the average of cell type expectations, $\beta_{ij}$, weighted by cell type fractions $x_{ki}$.

$$G_{jk} = \sum_i x_{ki} \beta_{ij} + \varepsilon_{jk} \qquad \text{(Equation 1)}$$

Comparing tumor versus no tumor expression levels amounts to using two cell types whose proportions are taken as either 1 and 0 (all tumor) or 0 and 1 (no tumor) in model (Equation 1) and taking the difference of the coefficients. Another procedure uses the proportions assessed by pathologists in a two-cell-type model. Coefficients, standard errors, and intercepts were calculated according to a two-cell type model (e.g., tumor vs. nontumor via simple linear regression of expression level on proportion of tumor cells) for each gene expression vector in 88 microarrays as a function of fractional content of tumor, then of stroma, and then of BPH. Thus, the expected cell type expression level is given as the regression coefficient, β, in the linear model (Equation 1). Modified t statistics incorporating goodness of fit and effect size were calculated according to Tusher (Proc. Natl. Acad. Sci. USA 98, 5116-5121, 2001), where ρβ is the standard error of the coefficient, and k is a small constant.

$$t = \beta/(k+\sigma_\beta) \qquad \text{(Equation 2)}$$

Figure 3:
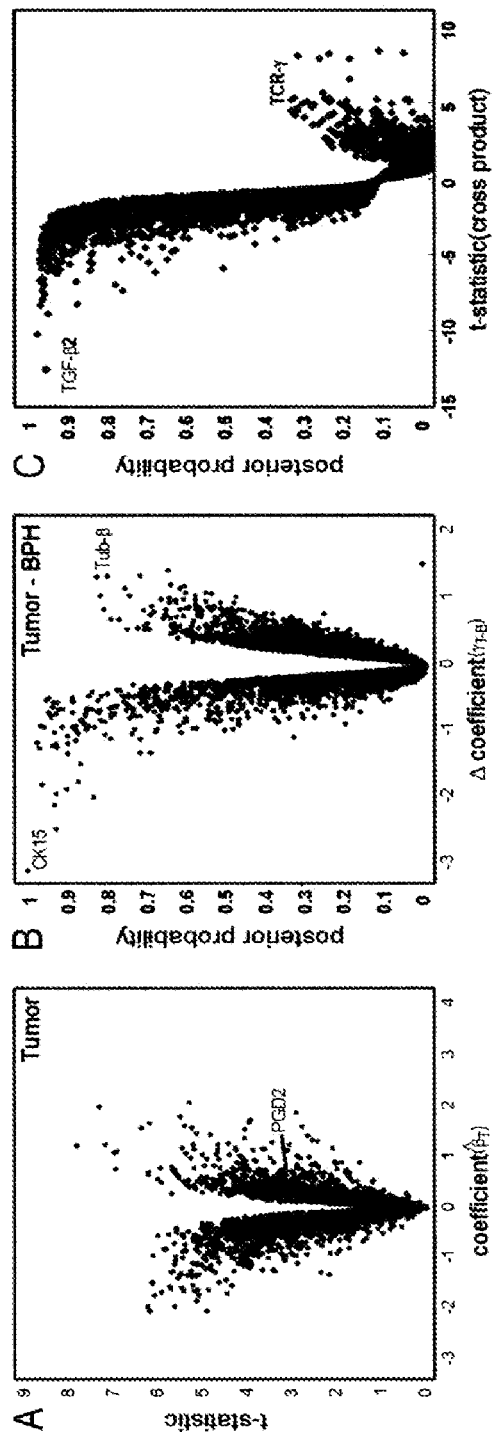
FIG. 3A-C shows statistical modeling. (A) Regression on cell type. The expected cell type expression levels are the coefficients β in models of gene expression as a linear function of fractional cell type (Equation 1) and were calculated by using the lsfit function in R. Modified t statistics were calculated as $t=\beta/(0.0029+\beta_{se})$, where se is the standard error of the coefficient. Volcano plot representations of the data reveal genes associated with the tumor cell type with high confidence in the upper right portion of the graph. (B) Multiple regression on percentage stroma, BPH, and tumor allows direct identification of tumor-BPH differences beyond the effect of stroma. Posterior probabilities akin to those in Efron et al. (J. Am. Stat. Assoc. 96, 1151-1160, 2001) used an estimating equations approach (gee library for R) (R Development Core Team (2004). R: A language and environment for statistical computing. R Foundation for Statistical Computing, Vienna, Austria. ISBN 3-900051-07-0, URL http://www.R-project.org.). BPH-specific gene expression is in the upper left (note CK15), and tumor-specific gene expression is in the upper right (tubulin-β) of the graph. (C) Tumor-stroma interaction model. Inclusion of cross-product terms in the linear model identifies genes in which the contribution of a cell may be more or less than in another tissue environment; i.e., the contributions of individual cell types to the overall profile depend on the proportions of other types present. Data show tumor-stroma cross-product modified t statistics versus probabilities (y axis), which were calculated as in B by comparing actual with permuted modified t statistics. The upper left portion of graph represents a large number of stroma-associated genes with a high likelihood deviation from a strictly linear model. The right portion of the graph reveals a number of tumor-associated genes that deviate from linearity. Among these is TCRγ, which is among the most discriminant tumor/no tumor genes even at low proportions of tumor; i.e., the expression of TCRγ is greater than that predicted by proportion of tumor cells alone. The stromal gene with the greatest deviation was TGF-β2, a candidate paracrine signaling molecule in prostate cancer.
Figure 4:
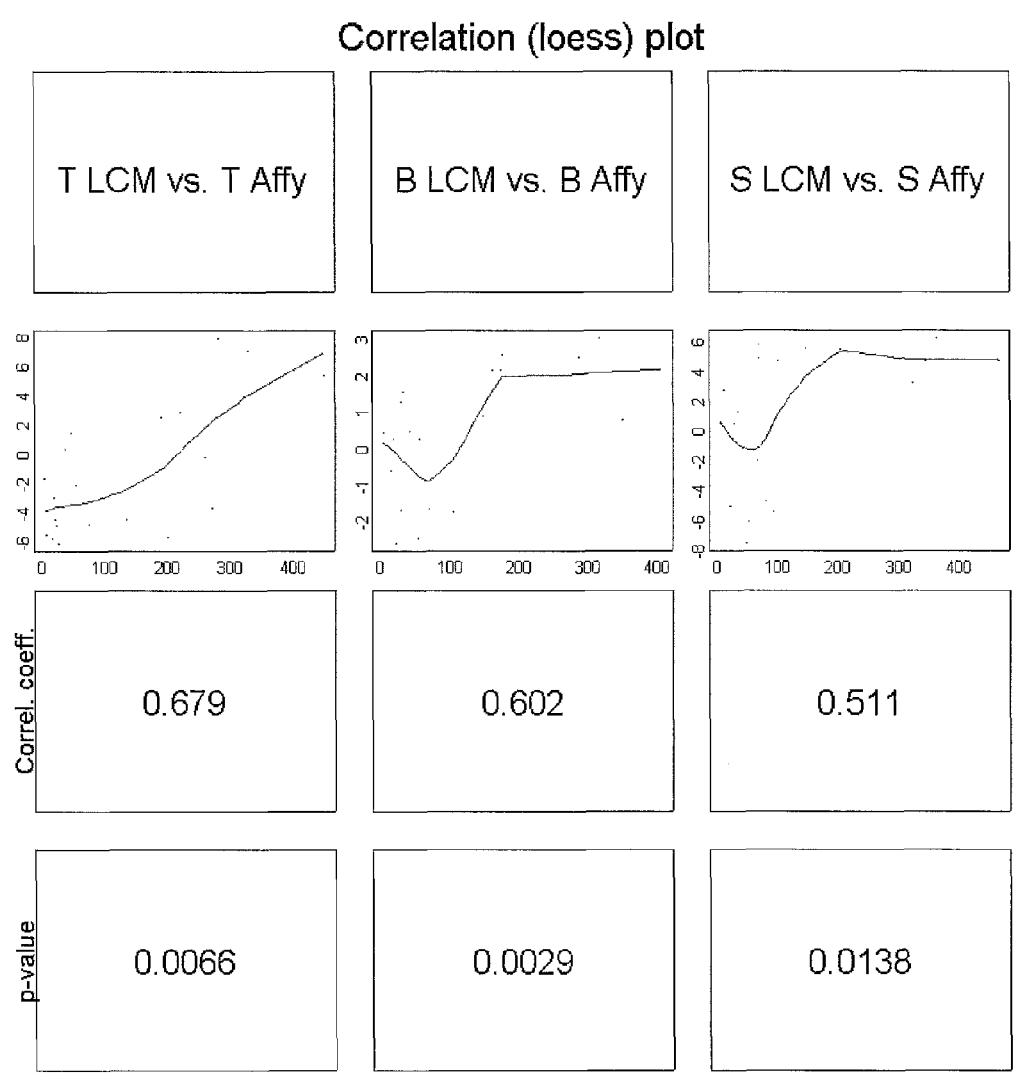
FIG. 4. Validation the GeneChip analysis with LCM/qPCR. Six prostate specimens were used for isolation of each cell type by laser capture microdissection (LCM). Primer sets for 31 selected genes including house keeping genes, including several genes validated by IHC (e.g. Tubulin-β, PSA, Desmin, and Cytokeratin-15), were used for assay of target gene expression by quantitative RT-PCR (qPCR). The qPCR data were subjected to quantile normalization. To assess the independence between modified t-statistics from Table 2 and the specific expression levels obtained by qPCR, Spearman Rank-Order correlation coefficients were evaluated for 20 genes with modified t-statistic >2.4 for at least one cell type (i.e. genes included on Table 2). The levels of significance (the p-values) of these correlation coefficients were estimated by test for association/correlation between paired samples from R (ref. 11). This analysis yielded coefficients of 0.679 ($p=0.0066$), 0.602 ($p=0.0029$), and 0.511 ($p=0.0138$) for the tumor, BPH, and stroma cell types, respectively. Thus, the qRT-PCR specific expression levels correlated with low probability to the cell-type modified t-statistic, determined for the same genes, as generated from the analysis of the GeneChip data. The graphs plot modified t-statistic along the ordinate against qPCR endpoint value (abscissa).

For n 88, a modified t statistic of 2.4 sets thresholds corresponding >4-fold expected differences in expression between the respective cell types (P<0.02). By these criteria, many transcripts were found to have strong association with a particular cell type (FIG. 3). A global view of predicted cell-specific gene expression was obtained by hierarchical clustering of the modified t statistics from the linear model. A total of 3,384 transcripts displayed cell-type-associated gene expression patterns according to the criteria. The procedure revealed that tumor- and nontumor-associated transcripts could be interpreted in terms of cell type specificity. Thus, 1,096 genes have strong tumor association, yet the majority (683) of these represent primarily differences in tumor-stroma gene expression (tumor>stroma). Conversely, a large number of transcripts are predicted to be stroma associated (stroma and stroma>tumor). Interestingly, a number of genes are strongly associated with BPH cell content (492). A subset of these (196) also showed a strong negative association with tumor cell content, indicating potential clinically useful markers of BPH. In addition, this analysis predicts 413 genes to be tumor specific, being strongly associated with tumor and displaying negative associations with both BPH and stroma.

The transcript groups were characterized by distinct personalities in terms of gene function. The BPH cell-associated groups (B>S, B>T) included a number of previously identified nonmalignant prostate epithelial markers including 15-lipoxygenase-II, CD38, and p63. This group contained a number of neuroendocrine markers such as cystatin-A, chromogranin-A, cholecystokinin, and cholecystokinin receptor. Notably, the BPH group of genes included IL-1 convertase. IL-1 is a putative neuroendocrine morphogen in prostate. The stroma cell compartment was dominated by archetypal smooth muscle and connective tissue-associated genes: vimentin, myosins, actin, and dystrophin. Other strong stroma associations included participants in transforming growth factor (TGF)-β and fibroblast growth factor signaling pathways.

Transcripts with strong tumor associations that were also anticorrelated with other cell types included hepsin, macmarcks, LIM protein, and α-methyl CoA racemase, as noted. A number of enzymes involved in O— and N-linked glycosylation were strongly tumor-specific, including UDP N-acetylglucosamine pyrophosphorylase-1, which in this study carried the third highest cell-type-associated modified t statistic of 7.2. Also noted were several genes participating in small GTP protein signaling pathways. The set of transcripts that were associated with both tumor and BPH cell content included, not surprisingly, PSA. In fact, six separate GeneChip probe sets for this gene present on the Affymetrix arrays segregated into this group.

Specific differences between BPH and tumor cell expression are of interest diagnostically and may shed light on pathogenesis. A four-cell-type model (via multiple regression of expression level on the tissue proportions using no intercept) allows direct and unbiased estimates of differences in expression between two cell types. Simultaneous regression holding the effect of stroma constant accounts for the fact that in the prostate, cell-type-associated differences in gene expression were dominated by the inverse relationship between fractional content of tumor cells and stromal cells. Because multiple samples are used from some subjects, the estimating equations approach implemented in the gee library for R was used. The procedure identified a number of transcripts predicted to be specific for either BPH or tumor cells (FIG. 3B). Cytokeratin-15 (CK15) expression was predicted with high confidence to be associated with the BPH cell type. Other putative BPH epithelial cell markers included the intermediate filament protein NF-H, histone H2A1B, CD38, and 15-lipoxygenase. Transcripts predicted to be specifically expressed in tumor as opposed to BPH cells included β-tubulin, UDP N-acetyl glucosamine pyrophosphorylase 1, and SGP-28, among others.

Including a term dependent on both the tumor cell proportion and the stroma cell proportion (i.e., the cross-product $x_{kT}x_{kS}$) in Equation 1 for the four-cell-type multiple regression model, the gene expression in stroma (or tumor) cells which is not independent but, rather, dependent on the proportion of tumor (or stroma) was calculated (FIG. 3C). Many genes displayed expression profiles with high tumor-stroma cross product terms including TGF-β2, which in the linear model is predicted to be in stroma. Also among stroma-associated genes with high cross products was desmin. Immunohistochemical staining (see below) supports this finding. High cross-product tumor-associated genes were also identified and included the T cell receptor γ (TCRγ) transcript (Affymetrix probe set 41468_at). In this instance, the high cross-product is the result of TCRγ transcript being a very highly discriminant tumor marker. That is, even relatively low percentage tumor samples display high expression, an exception to the linear model consistent with stromal modulation of tumor TCR expression.

Immunohistochemical Validation. Selected predicted cell-type-specific gene expression patterns were tested by examining the distribution of gene expression on the protein level by using immunohistochemistry. At least five cases of tumor-bearing tissue with adjacent BPH, stroma, and dilated glands were examined with each antibody. β-Tubulin is predicted to be a strongly tumor-associated gene. Immunohistochemical staining revealed uniform expression in tumor cells of crowded gland-like structures of the tumor but negative in stroma or epithelial cells of adjacent BPH and dilated glands. Prostaglandin-D2 synthase (PD2S) is predicted to be a moderately tumor-associated gene. Apical surfaces of the epithelial cells of tumor-gland structures were highly immunoreactive, whereas BPH glands displayed little or no immunoreactivity. Prostate-specific membrane antigen (PSMA) is predicted to be strongly tumor associated. Staining revealed strong immunoreactivity that was strictly confined to the apical membranes of tumor gland cells, but only weak reactivity was observed in adjacent BPH cells. Desmin is predicted to be a stromal gene with high likelihood of tumor-stroma cell interaction. Numerous desmin-positive spindle shaped cells forming files and parallel clusters fill the stroma tissue component, whereas all epithelial cells are negative. The stroma within zones of tumor is distinct from adjacent normal stroma in that the desmin-positive spindle cell population is sparse, suggesting a distinct remodeling of cells in the tumor-associated stroma. CK15 is predicted to be strongly associated with BPH. Uniform labeling of most cells of myoepithelial of hyperplastic epithelium was apparent, whereas no expression could be detected in adjacent tumor cells of the same cases. PSA is predicted to be present in BPH and tumor cells. Strong immunoreactivity was noted in both tumor and BPH glands. These observations provide direct confirmation of the cell-type-specific expression of proteins as predicted on the basis of the dissection of transcript expression described here.

LCM-qPCR Validation. Five independent specimens and one specimen used for expression analysis were used for isolation of tumor, BPH, and stromal cells by LCM. Primer sets for 28 genes, including several genes validated by immunohistochemistry, were examined by qPCR, such as PSA, β-tubulin, desmin, and Cytokeratin-15, 504 PCR runs in all. The overall pattern of qPCR results exhibited a clear correlation with the expression level based on cell type. To quantitatively examine the relationship, the Pearson correlation coefficient and associated probability for each cell type was calculated between qPCR end points from the LCM samples, and the corresponding modified t statistics derived from the in silico dissection for the same cell type across the 20 genes with complete data. This analysis yielded correlation coefficients of 0.689 (P=0.004), 0.609 (P=0.0042), and 0.524 (P=0.0144) for the tumor, BPH, and stroma cell types, respectively. Thus, all correlation coefficients are statistically significant. It is apparent, therefore, that for all three cell types there is a significant correlation between these two independent and multistep methods of cell-type-specific analysis for the genes examined.

The analysis was conducted in order to discriminate true markers of tumor cells, BPH cells, and stromal cells of Prostate Cancer. Conventional least squares regression using individual cell-type proportions produces clear predictions of cell specific expression for a large number of genes. Many predictions are readily accepted on the basis of prior knowledge of prostate gene expression and biology, which provides confidence in the method. These are strikingly illustrated by numerous genes predicted to be preferentially expressed by stromal cells that are characteristic of connective tissue and only poorly expressed or absent in epithelial cells.

This analysis allows segregation of molecular tumor and non-tumor markers into more discrete and informative groups. Thus, genes identified as tumor-associated may be further categorized into tumor versus stroma (epithelial versus mesenchymal) and tumor versus BPH (perhaps reflecting true differences between the malignant cell and its hyperplastic counterpart). A recent meta-analysis produced a list of 500 genes up-regulated in prostate cancer. Of these 338 (unique Unigene identifiers) were identified in the analysis provided herein as tightly correlated with the presence of tumor. The method presented here indicates that 157 of these tumor-associated transcripts represent a tumor-stroma dichotomy. Another 26 are associated with BPH cells and tumor cells, and 89 are relatively unique to tumor cells. Notably, only 2 transcripts associated by the herein disclosed method with stroma were classified as tumor-associated in the meta-analysis. Conversely, 296 of 500 genes identified in the meta-analysis as indicative of normal prostate can be divided into 271 stromal genes and only 15 genes associated with BPH cells and not malignant cells. Thus, the vast majority of markers associated with normal prostate tissues in recent microarray-based studies are related to cells of the stroma. This result is not surprising given that, at least here, normal samples are composed of a relatively greater proportion of stromal cells.

The strongest single discriminator between BPH cells and tumor cells in this study was cytokeratin-15 (CK15), a result confirmed by immunohistochemistry. CK15 has previously received little attention in this context, but BPH markers play an important role in the diagnosis of ambiguous clinical cases. The clinical utility of CK15 and other predicted BPH markers will require further study.

It was expected that not all genes would be expressed as a linear function of cell-type. Transcripts with high cross-products in the covariance matrix suggest that expression in one cell type was not independent of the proportion of another tissue as would be expected in a paracrine mechanism. The stroma transcript with the highest dependence on tumor percentage was TGF-b2, a cytokine previously identified as important in prostate cell proliferation. Another such stroma cell gene for which immunohistochemistry was practical was desmin which showed considerably altered staining in the tumor associated stroma. In fact, a large number of typical stroma cell genes displayed dependence on the proportion of tumor adding evidence to the speculation that tumor-associated stroma differs fundamentally from non-associated stroma. Tumor-stroma paracrine signaling may be reflected in peri-tumor halos of altered gene expression that may be present a much bigger target for detection than the tumor cells alone.

Recently, a group of genes was identified that correlated with Gleason score and clinical outcome. These studies were restricted to specimens with very high proportions of tumor cells. Therefore, in contrast to the study provided herein, the previous study could not assess the role of cells neighboring the cancer, which may participate in the gene expression signature of tumor and, possibly, its biology.

The experiments have employed a straightforward bioinformatics approach using simple and multiple linear regression to identify genes whose expression is specifically correlated with either tumor cells, BPH epithelial cells or stromal cells. These results confirm a variety of previous observations and importantly identify a large number of gene candidates as specific products of various cells involved in prostate cancer pathogenesis. Context-dependent expression that is not readily attributable to single cell types is also recognized. The investigative approach described here is applicable to a wide variety of tumor marker discovery investigations in other organs.

Laser Capture Microdissection and Extraction. From each flash-frozen tissue, 5μ thick frozen sections were prepared. Sections were subsequently dehydrated in graded ethanol solutions (70% once, 5 second rinse, 95% twice, 5 second rinse each, 100% two times, 5 second rinse each) and cleared in xylene (two times, 5 min each). After air-drying for 10 min, we used the PixCell II LCM System from Acturus Engineering (Mountain View, Calif.) for laser capture and followed the manufacturer's protocol. Total RNA was extracted using resin spin-column system (PicoPure RNA isolation Kit, Arcturus Engineering).

Analysis of Gene Expression by Real-Time Quantitative (qPCR). First strand cDNA synthesis was performed using all extracted total RNA from each sample (preheated at 65° C., 5 min with oligo-dT(15) and dNTPs) in 0.5 μg oligo-dT(15), 50 mM Tris-HCl (pH 8.3 at room temperature), 75 mM KCl, 3 mM $MgCl_2$, 10 mM dithiothereitol, 0.5 mM dNTPs, 2 units/ul of RNase Inhibitor (Roche) and 10 units/ul SuperScript II RNase H-Reverse Transcriptase (Invitrogen Corporation). Reverse Transcriptase was added after two minutes of incubation at 42° C., then incubate for 50 minutes at 42° C. The reaction was inactivated at 70° C. for 15 min. 20 μl cDNA reaction was diluted to 400 μl and 6 μl was used for analysis of each gene. Real-time quantitative PCR (ABI Prism 7900 Sequence Detection System, Applied Biosystems, Foster City, Calif.) was carried out for the analysis of gene expression by the use of SybrGreen. Real-time PCR reaction contained 1× HotStartTaq PCR Buffer (with 1.5 mM MgCl2), 1:25,000 dilution of SybrGreen I (Molecular Probes), 0.35 μM 6-ROX (Molecular Probes), 0.2 mM dNTPs, 4 mM MgCl2, 0.025 unit/μl HotStartTaq DNA polymerase (Qiagen) and 0.8 μM each primer. Real-time PCR was done in 95° C. for 15 minutes; 50 cycles of 95° C. for 15 seconds, 60° C. for 15 seconds and 72° C. for 30 seconds; followed by a dissociation stage (95° C. 15 seconds, 60° C. 15 seconds, 95° C. 15 seconds, 2% ramping rate from 60° C. to 95° C.). Relative standard curves representing decreasing dilutions of stock cDNA were used for monitoring efficiency of target amplification of each gene. Thirty-one genes were amplified. The primer pair sequences for each of the specific RNA transcripts assayed are listed in Table 1.

Quantile normalization. The intensity values of each LCM sample were quantile normalized; the kth ranked intensity among the K=24 genes for each LCM sample was replaced by the average of the kth ranked values across all samples. For a few LCM samples readings were not been obtained for some genes. These samples were not included in the averaging, but normalized values for the non-missing genes were obtained by replacing the rank, j, among the J valid values for a sample with (j−1)*(K−1)/(J−1)+1 and using this to interpolate among the K averages.

Table 8. Selected Cell-type specific Expressed Genes. The table provides a modified t-statistic calculated as described herein (Equation 2) for each cell type (tumor (T), BPH, (B), and stroma (S)) defined and selected differences (T-B) for each gene with t>2.4. The modified t-statistics $t_{ij}$ incorporates goodness of fit and effect size for every gene j and every tissue type i, where $\sigma_\beta$ the standard error of the coefficient, $\beta_{ij}$, and k is a small constant: $t_{ij}=\beta_{ij}(k+\sigma_\beta)$. The $\beta_{ij}$ are determined according to equation (1) as described. For N=88, a modified t-statistic of 2.4 sets thresholds-corresponding greater than four-fold expected differences in expression between the respective cell types (p<0.02). 3384 transcripts displayed cell-type associated gene expression patterns according to the threshold and are listed here. 1096 genes have strong tumor association, yet the majority (683) of these represent primarily differences in tumor-stroma gene expression (tumor>stroma). Conversely, a large number of transcripts are predicted to be stroma associated (groups stroma and stroma>tumor). 492 are strongly associated with BPH cell content. A subset of these (196) also showed a strong negative association with tumor cell content indicating potential clinically useful markers of BPH. 413 are predicted to be tumor specific, being strongly associated with tumor and displaying negative associations with both BPH and stroma (tumor). Columns B, C, and D labeled BSTAT, SSTAT, and TSTAT respectively are the corresponding modified t-statistic values for simple regression using percent composition for each tissue type alone (cf. equation 1), i.e. BPH epithelial cells content, stroma cell content, or tumor epithelial cell content respectively. The modified t-statistic value are color coded Red for modified t-statistic >2.0; Tan for 2.0>modified t-statistic >1.0, Green for t-static ←2.0, and Blue for −2.0<modified t-statistic ←1.0.

The modified t statistics calculated from two-cell-type linear models embody the direction and magnitude as well as goodness of fit of the coefficients. The modified t statistics were filtered to include genes with >4-fold predicted changes in between pure and 0% specific cell type sample composition and an absolute correlation coefficient of >0.25. By these criteria, 3,387 transcripts displayed cell-type-associated gene expression, and the modified t statistics are visualized here by hierarchical clustering. Red corresponds to a positive correlation, and green corresponds to a negative correlation between cell type (B, BPH; S, stroma; T, tumor) and gene expression. Representative genes from each group are at right. Previously available tumor/no tumor distinction is represented by middle labels. The analysis provides for further classification of no tumor markers into stromal (the vast majority) and BPH-associated genes. Likewise, tumor markers can be subdivided. Markers of the tumor-stroma difference may reflect epithelial mesenchymal differences in gene expression. Genes that differ according to the tumor-BPH distinction may reflect changes between malignant and non-malignant states of prostate epithelium.

Example 2

Identification of Differences in Expression Between Cell-Types and Between Relapse and Non-Relapse Patients Methods have been developed which have promise to distinguish cell-specific and relapse-specific differential gene expression which will be assessed on available clinical cases in a prospective observational trial design.

1. Sample Evaluation. Percent sample composition determination. All samples used in microarray analysis were evaluated by four pathologists, who independently estimated percentage of tumor-, stroma-, BPH- and Cystic-Atrophy-cells in every sample using serial frozen sections as described in Example 1. Tissue between these analytical sections was utilized for RNA preparation and expression analysis. The reliability of tissue composition estimates by this method has been checked by carrying out a variety of agreement analyses among the four pathologists such as calculation of agreement of presence or absence of tissue types (kappa) and Pearson correlation coefficient calculations for percent assignments. An example of such an analysis in the case of estimating tumor cell content is shown in FIG. 1 and a summary for the four cells types estimated is shown in Table 3. The percent estimates averaged over the four contributing pathologists for each sample were used to derive cell-specific gene expression estimates as described below and summarized in Example 1; averaged values were used in the analysis.

2. Gene Expression Data Processing.

Total RNA was prepared from samples of known cellular composition and analyzed on Affymetrix GeneChip platforms as described by the manufacturer. The data of the hybridized microarrays were processed by Affymetrix Microarray Suite 5.0. (Affymetrix (2000). Microarray Suite 5.0—User Guide. Affymetrix, Inc. (www.affymetrix.com)). The background estimation and gene expression evaluation was carried out using BioConductor's Affymetrix package (Rafael A. Irizarry, Laurent Gautier, Benjamin Milo Bolstad, Crispin Miller, with contributions from Magnus Astr, Leslie M. Cope, Robert Gentleman Jeff Gentry Wolfgang Huber James MacDonald Benjamin I. P. Rubinstein Christopher Workman and John Zhang (2004). Affymetrix: Methods for Affymetrix oligonucleotide Arrays. R package version 1.5.8.).

3. Two GeneChip data sets. Samples from 55 patients were hybridized to 118 U95Av2 GeneChips and samples from 91 patients were hybridized to 146 U133A GeneChips. Samples from 34 patients were hybridized to both chip types. 54 samples were hybridized to both chip types. These data sets and the distribution among relapse and nonrelapse samples are summarized in Tables 4 & 5.

4. Determination of Cell-Specific Gene Expression by Regression analysis for Four Cell-types. In accord with the common histology of prostate, we assume (1) that the vast majority of cell types of tumor-bearing prostate tissue is accounted for by four cell types: Tumor epithelial cells, BPH epithelial cells, stromal cells (combined smooth muscle and connective tissue cells, and the flattened epithelial lining of dilated cystic glands). We assume (2) that the amount of mRNA of a given gene in extracted prostate tissue is derived from these four cell types in proportion to the amount of that cell type observed in a given case. That is, we postulate that a linear model accounts for the Affymetrix GeneChip Intensity:

$$y_{ij}=\beta_{BPH,j}x_{BPH,i}+\beta_{T,j}x_{T,j}+\beta_{S,j}x_{S,j}+\beta_{G,j}x_{G,j}+\epsilon_{i,j}, \quad (3)$$

where $y_{ij}$ is the observed gene expression intensity of a gene j in a sample i, $x_{xi}$ is a percentage of cell-type X in sample i and $\beta_{xj}$ is a regression coefficient for gene j and cell-type X, defining the contribution of the proportion of the cell-type X to the overall gene expression intensity of the gene j, obtained fitting the model.

The β coefficients are the change in gene expression per unit cell (i.e. the slope of plots of gene intensity vs. percent composition) and therefore are cell specific gene intensity coefficients. For the model of equation 3, no distinction has been made in the gene expression properties of tumor cells from different samples which may have different Gleason scores or varying phenotypes such as aggressive growth (Example 1). These β coefficients are, therefore, average characteristic gene expression properties of a given cell type. Aggressive versus indolent disease is treated below in section 6 below.

The coefficients of the model, equation 3, may be obtained by regression analysis (Draper N and Smith H. Applied Regression Analysis. John Wiley and Sons, New York 1981). Because there are multiple samples for some patients and samples for one patient generally have a different correlation structure then other patients, we fitted the model with Generalized Estimation Equation (GEE) by means of the package gee in R (Diggle, P. J., P. Heagerty, et al. (2002). Analysis of Longitudinal Data. Oxford University Press 2nd edition, Oxford, England). The procedure minimizes the residual by an iterative process.

To determine significant $\beta_{xj}$ values, i.e. significant correlation of gene expression with the amount of a given cell type, we test the null-hypothesis, that correlation coefficient $\beta_{xj}=0$. $\beta_{xj}$ may be significant for only some genes, the significant genes. The tuned modified t-statistic after Tusher (Tusher, V. G., R. Tibshirani, et al. (2001). Significance analysis of microarrays applied to the ionizing radiation response. Proc Natl Acad Sci USA 98(9): 5116-21) was computed. It evaluates the correlation of gene j with the proportion of the cell-type X:

$$t_{j,X} = \frac{\beta_{X,j}}{(\sigma_j + k)}, \quad (4)$$

where $\sigma_j$ is a standard error of the coefficient $\beta_{xj}$ and k is a small constant penalizing the weakly expressed genes (Tusher and Tibshirani 2001).

Cell-specific expression lists have been derived herein. For N=88 GeneChips, a modified t-statistic of 2.4 sets thresholds corresponding to greater than four-fold expected differences in expression between the respective cell types (p<0.02). 3384 transcripts displayed cell-type associated gene expression patterns according to the threshold and are listed here. 1096 genes have strong tumor association, yet the majority (683) of these represent primarily differences in tumor-stroma gene expression (tumor>stroma). Conversely, a large number of transcripts are predicted to be stroma associated (groups stroma and stroma>tumor). 492 are strongly associated with BPH cell content. A subset of these (196) also showed a strong negative association with tumor cell content indicating potential clinically useful markers of BPH. 413 are predicted to be tumor specific, being strongly associated with tumor and displaying negative associations with both BPH and stroma.

5. Independent Replication of Cell-Specific Gene Expression. The analysis of 53 samples on U95Av2 in Example 1 indicated that cell-specific gene expression could be deduced from a knowledge of cell composition. A test was undertaken to determine whether the cell-specific results of multiple regression analysis of sample of known cellular composition was reproducible and general. The multiple linear regression results were quantitatively compared for the samples analyzed by the U95Av2 GeneChips with independent samples analyzed on U133A GeneChips with independent probe sets. First, a mapping between common samples genes of each platform was created.

Mapping between U95Av2 and U133A: replication of Example 1. The mapping of the probe sets from U95Av2 to probe sets of U133A was based on Affymetrix Best Mapping (Affymetrix, Palo Alto, Calif.). 10,507 probe sets of the U95Av2 GeneChip were mapped to 9530 probe sets on the U133A GeneChip. There are approximately 22,000 probe sets on the U133A GeneChip. Thus, the mapped probe sets represents most of the U95Av2 probe sets and over 40% of the U133A probe sets. The 9530 probe sets correspond to approximately 6235 human genes.

Comparison of 4 cell-type regression analysis results for U95 and U133. Regression analysis for 4 cell-types was performed for both the U95Av2 and U133a data sets using the intensities of the mapped probe sets. The respective modified t-statistics for four cell types of both GeneChips were determined. The comparison is for 110 samples measured on the U95Av2 and 93 different samples measured by U133A. The results may be assessed by correlating modified t-statistics for these probe sets for each cell type (Table 5).

For modified t-statistics >2.4, i.e. uniformly cell-specifically expressed genes across all samples, the comparison yielded positive Pearson correlation coefficients between modified t-statistics for a given gene are in the range of 0.72 to 0.94 for the four cell types indicating excellent agreement for the determination of the same genes as cell specific in both analyses. Indeed, when all genes represented by the mapped probe sets were considered, significant positive correlations were still observed (Table 5). Since the results represent independent samples and independent gene expression analyses, these observations argue that the method of cell specific gene expression determination is reproducible and robust. Genes that are tissue specific in the U133A set are presented in Table 8.

6. Regression analysis for four cell-types and the categorical variable 'relapse case', rs: identification of differentially expressed genes in early relapse Prostate Carcinoma.

During the course of this study a number of patients exhibited postoperative PSA values greater than the test threshold. For the purposes of an interim calculation, all such patients were taken as having exhibited chemical relapse. Relapse in turn is taken as a surrogate marker of Aggressive prostate cancer. To obtain the molecular signature of 'being a relapse sample', an extended linear model was built to determine the cell-specific significant genes correlated with the categorical variable rs ('being a relapse case'):

$$y_{ij} = \beta'_{BPH,j} x_{BPH,i} + \beta'_{T,j} x_{T,i} + \beta'_{S,j} x_{S,i} + \beta'_{G,j} x_{G,i} + rs(\gamma_{BPH,j} x_{BPH,i} + \gamma_{T,j} x_{T,i} + \gamma_{S,j} x_{S,i} + \gamma_{G,j} x_{G,i}) + \epsilon_{ij}, \quad (5)$$

where $\beta'_{x,j}$ values define the contribution of the nonrelapsed cell-type expression for gene j and cell-type X; and the $\gamma_{xj}$ are the regression coefficients, defining the contribution of the relapsed cell-type X to the overall gene expression intensity of gene j. There are two-way interactions of type rs*$x_{xj}$ in the model.

Further, the False Discovery Rate (FDR) was estimated by means of a permutation schema (Good, Phillip: Permutation Tests, A Practical Guide to Resampling Methods for Testing Hypotheses, 1993, Springer Verlag, New York). FDR is a proportion of false positives in a set of significant genes, discovered by some rule. The null-hypothesis was, $\beta_{xj}=0$—'being a relapse case' has no influence on the overall gene expression. The permutation schema honored the null model and enforced its correlation structure as provided herein. This process was repeated 20-times. The distribution of the modified t-statistic considering the 20 repetitions for every cell-type gave the null-distribution of the modified t-statistics, which was compared to the actual data. The resulting FDR values are in parentheses in Table 6. ~1100 probe sets of the ~22,000 probe sets on the Affymetrix U133A GeneChip are significantly differentially expressed between nonrelapsed and early relapse Prostate Cancer. Of these, approximately 13% are false positives. Table 9 contains a list of the most significantly different genes discovered tumor that are changed in patient that have a higher risk of relapse. Table 10 contains genes that are different in stroma in relapse versus non-relapse patients.

Several particular observations are noted. First, although cell specific expression by BPH epithelium is readily apparent (Example 1), no significant gene expression changes in BPH were resolved when comparing relapsed status. This is consistent with the general observation that BPH is not a precursor lesion or factor in progression (Chung, L., Isaacs, W., and Simons, J. Prostate Cancer, Biology, Genetics, and the New Therapeutics. 2001, Human Press, New York). Second, most changes are associated with a negative γ indicating decreased gene expression with aggression, which correlates with dedifferentiation with progression (Chung et al. 2001). Third, many of the most significant gene expression changes are associated with stromal cells. The large number of differential changes in stroma may correlate with growing indications that stroma is an integral part of Prostate Cancer Progression through paracrine interactions.

The identification of genes specific to stroma and early relapse predicts that analysis of stroma alone as in negative clinical prostate biopsies may be predictive of the presence of cancer and whether indolent or aggressive disease is present. This hypothesis is readily testable both experimentally by validation studies and analytically by, for example, application of classifiers to independent data sets. A stroma classifier is developed in section 7.

When the original distribution of modified t-statistics for a particular cell-type X (e.g. stroma cell) is compared with the appropriate null-distribution, an increased frequency of modified t-statistics is apparent for (modified t-statistic)/(standard deviation) <~–1. FDR is determined as the as the ratio of areas of interest of the null distribution to the original distribution of modified t-statistics.

7. Development of Candidate Classifier of Aggressive Prostate Cancer by use of genes differentially expressed in early relapse Prostate Cancer: the 43-gene classifier.

We sought to develop a classification rule based on known samples that could be applied to the classification of unknown samples. The modified t-statistics calculated in Section 5 (U133A samples) were used as the basis for building the classifying rule. We selected 1024 genes contributing the best 1024 modified t-statistics for all cell types. Some genes contributed more that one modified t-statistic owing to the presence of multiple probe sets for that gene on the U133A GeneChip. We built a restricted model of the type of Eqn (5) by setting a gamma=0 except for the 1024 genes with the best modified t-statistics. The model was fitted by employing a version of diagonal linear discriminant analysis. The generalization error and standard deviation was estimated by repeated 10-fold cross validation by serially leaving out the gene with the lowest modified t-statistic. A set of 43 genes was selected that had generalization errors less than one standard deviation from the minimum generalization error, as provided in Table 11.

The results of the classifier when applied to various data sets are in Table 7.

These results are likely underestimates since the nonrelapse data of this interim analysis necessarily contains gene signatures of cases that will relapse within 5 years (~20% of all radical prostatectomy patients relapse; ~40% relapse within 2 years of surgery, ~49% relapse within 3 years; Chung et al 2001).

It should be noted that the classifier does not directly account for cell-specific gene expression.

8. Development of a nontumor-based Stromal classifier for aggressive Prostate Cancer.

Samples from tumor-bearing prostate glands that were confirmed by serial frozen sections to be free of tumor cells were used to predict genes associated with relapse in stroma, and BPH. The top 144 down-regulated genes in the permutation analysis are listed in Table 12. In addition, the top 100 up-regulated genes are also listed in Table 13.

The 144 genes were all tested as the starting set for a Support Vector Machine (SVM) application. This method seeks a subset of genes that discriminate two or more data sets in a manner that is independent of cell composition. Thus, a classifier derived in this was may be applied to independent data sets of unknown cell composition.

The result for the application of the 144 gene classifier to our nontumor samples was the correct classification of relapse status in 79.1% of the samples. The classifier has been tested on an entirely independent data set composed of known relapsed and nonrelapsed cases of Febbo et al. (Febbo P G, Sellers W R. Use of expression analysis to predict outcome after radical prostatectomy. J Urol. December 2003; 170(6 Pt 2):S11-9; discussion S19-20) with a result of 76%. However, the Febbo at al. 2003 are tumor samples only, with high percentage of tumor. These results far exceed random expectation. As before, these performance results are likely underestimates owing to the use of nonrelapse data in this interim analysis, which almost certainly contains late relapsing cases.

A number of embodiments are been described herein. Nevertheless, it will be understood that various modifications may be made without departing from the spirit and scope of the methods, compositions and kits. Accordingly, since modifications will be apparent to those of skill in this art, it is intended that this invention be limited only by the scope of the appended claims.

TABLE 1

Genes and Sequences of real-time quantitative RT-PCR primers of measured gene transcripts
(Fwd Primer column discloses SEQ ID NO: 38,827-38,857, respectively, in order of appearance.
Rev Primer column discloses SEQ ID NOS: 38,858-38,888, respectively, in order of appearance.)

| HUGO Name | Accession No. | UniGene | Fwd Primer (5'-3') | Rev Primer (5'-3') | Llength (bp) |
|---|---|---|---|---|---|
| | | | G | | |
| glyceraldehyde-3-phosphate dehydrogenase | NM_002046 | Hs.169476 | GAAGGTGAAGGTCGGAGTC | GAAGATGGTGATGGGATTTC | 226 |

TABLE 1-continued

Genes and Sequences of real-time quantitative RT-PCR primers of measured gene transcripts
(Fwd Primer column discloses SEQ ID NO: 38,827-38,857, respectively, in order of appearance.
Rev Primer column discloses SEQ ID NOS: 38,858-38,888, respectively, in order of appearance.)

| HUGO Name | Accession No. | UniGene | Fwd Primer (5'-3') | Rev Primer (5'-3') | Length (bp) |
|---|---|---|---|---|---|
| kallikrein 3, (prostate specific antigen) | NM_001648 | Hs.171995 | TGGTGCTGCACCCCTCAT | CCAGGGTTGGGAATGCTTCT | 70 |
| tropomyosin 1 (alpha) | NM_000366 | Hs.77899 | GAAGATGCCGACCGCAAAT | CGTTCCAGGTCGCTCTCAAT | 68 |
| actin, alpha 2, smooth muscle, aorta | NM_001613 | Hs.195851 | TGGTCATCCTCCCTTGAGAAGA | CGTTCATTTCCGATGGTGATC | 68 |
| collagen, type I, alpha 1 | NM_000088 | Hs.172928 | GGCTTCCCTGGTCCTCTTG | GGGACCACGTTCACCACTTG | 78 |
| hepsin (transmembrane protease, serine 1) | NM_002151 | Hs.823 | TTTGTGTGTGAGGACAGCATCTC | GCCCCAACTCACAATGCC | 66 |
| MARCKS-like protein | NM_023009 | Hs.75061 | GCGCTGAGCAGAATGAGTAGCT | ACCTCACAAGGACAGCACAGTTT | 79 |
| LIM | NM_006457 | Hs.154103 | CCTGGAAGCTCTGGGCTACAC | TTCCAAACTTTCACAACACACTGA | 70 |
| thymosin, beta 4, Y chromosome | NM_004202 | Hs.159201 | GCGACCTGGGCTCCATTT | AGCCACTTCCGCGTTCAAG | 63 |
| kallikrein 2, prostatic | NM_005551 | Hs.181350 | CGTGCCCCTCATCCAGTCT | GCCAGGGTTGGGAATGCT | 65 |
| acid phosphatase, prostate | NM_001099 | Hs.1852 | TTTCTCAGGGCAGATGATGCT | AAGCCCATTTTCCTCAAAGCT | 71 |
| keratin 15 | NM_002275 | Hs.80342 | CTCCAGTCCCTGCCTTCAGA | GCATGCAAAGCCCTGAAATAA | 66 |
| keratin 5 (epidermolysis bullosa simplex, Dowling-Meara/Kobner/Weber-Cockayne types) | NM_000424 | Hs.433845 | CACAGAGATGAACCGGATGATC | TTGGCGCACTGTTTCTTGAC | 69 |
| prostaglandin D2 synthase (21 kD, brain) | NM_000954 | Hs.8272 | GGGCTTCACAGAGGATACCATT | AGTCCTATTGTTCCGTCATGCA | 68 |
| CD44 antigen (homing function and Indian blood group system) | NM_000610 | Hs.169610 | CCTCTGCAAGGCTTTCAATAGC | CGATGCTCAGAGCTTTCTCCAT | 65 |
| tropomyosin 2 (beta) | NM_003289 | Hs.300772 | CGAGAGCCGAGCCAGACA | CTCTGAGGCCATCAGGGACTT | 76 |
| Desmin | NM_001927 | Hs.279604 | CCAGTCCTACACCTGCGAGATT | CCTCCAATTCCCGCATCTG | 77 |
| Transforming growth factor, beta 1 (Camurati-Engelmann disease) | NM_000660 | Hs.1103 | CTCTCCGACCTGCCACAGA | AACCTAGATGGGCGCGATCT | 72 |
| filamin A, alpha (actin binding protein 280) | NM_001456 | Hs.195464 | CAGGCTTGGTGTCTGCTTACG | TCCCGCATTGCTCGTGTT | 89 |
| myosin, light polypeptide 9, regulatory | NM_006097 | Hs.9615 | TTAAGGAGGCTTTCAACATGATTG | GTCGTGCAGGTCCTCCTTGT | 68 |
| myosin, heavy polypeptide 11, smooth muscle | NM_002474 | Hs.78344 | ACGGGAGAGCTGGAAAAGC | TTTTGGCGTTGCCGAAAG | 67 |
| Synaptogyrin 1 | NM_004711 | Hs.6139 | CCAAAGGACAGCAGTGATGGA | CCGGATTGGAAAATGAAGTCA | 79 |
| eukaryotic translation elongation factor 1 alpha 1 | NM_001402 | Hs.181165 | CTGAACCATCCAGGCCAAAT | GCCGTGTGGCAATCCAAT | 59 |

TABLE 1-continued

Genes and Sequences of real-time quantitative RT-PCR primers of measured gene transcripts
(Fwd Primer column discloses SEQ ID NO: 38,827-38,857, respectively, in order of appearance.
Rev Primer column discloses SEQ ID NOS: 38,858-38,888, respectively, in order of appearance.)

| HUGO Name | Accession No. | UniGene | Fwd Primer (5'-3') | Rev Primer (5'-3') | Llength (bp) |
|---|---|---|---|---|---|
| single-minded homolog 2 (Drosophila) | NM_005069.2 | Hs.27311 | TTTAGGACCGTGGGTCATGC | ATAGCTGAGTGCGTGGAGAGG | 77 |
| alpha-methylacyl-CoA racemase | NM_014324.2 | Hs.128749 | GTGAAACAGAGTGATTGGTTGCA | GAATGTGCTTAGAGGGAGATCATGA | 70 |
| UDP-N-acteylglucosamine pyrophosphorylase 1 | NM_003115.2 | Hs.21293 | CTCTCCTCTTATCTCCTATGCTGGA | CGATGATTAGAGGTGCATGGAA | 80 |
| RAB4A, member RAS oncogene family | NM_004578.2 | Hs.119007 | GAGACAGCTGAGGTCACCGC | ATTGTGTCCCAAATGCCACTG | 104 |
| CD38 antigen (p45) | NM_001775.1 | Hs.66052 | CACCATAAAAGAGCTGGAATCGAGTAGTGGAATATGTCTTCTGTATAA | GTGCAAGATGAATCCTCAGGATTT | 120 |
| homeo box A9 | NM_002142.3 | | CTAGGCT | CATCCCCGAGAACACTTAAAATTT | 108 |
| tubulin, alpha 1 (testis specific) | NM_006000.1 | Hs.75318 | TCTGTTTGCTGTTCATGACCCT | AAGAACCCCTTTGCAGGTCTC | 65 |
| Arachidonate 15-lipoxygenase, second type | NM_001141.1 | Hs.111256 | CATGCGAGGGCTTCATAGC | GATGCCCCTCGAGATCTGG | 197 |

TABLE 3

Summary of Agreement Analysis Among Four
Pathologists
126 Sample Slides
363 Ratings
Average Pearson Correlation Coefficients:

| Tumor epithelial cells | 0.92 |
|---|---|
| BPH epithelial cells | 0.73 |
| Stroma-all cells | 0.77 |
| Dilated Cystic Glands epithelial cells | 0.49 |

TABLE 4

Summary of Prostate Carcinoma Cases with known Cell Composition and Clinical Follow-up Analyzed by Affymetrix GeneChips.

| Set | Patients | Micro Chips | Tumor-Bearing Samples | Non Tumor-Bearing Samples | Relapse Tumor Samples | Non relapse Tumor Samples | Patients Analyzed on both U95/U133 | RNA Extracts Analyzed on both U95/U133 |
|---|---|---|---|---|---|---|---|---|
| U95Av2 | | 88 | 38 | 50 | | | 34 | 54 |
| Example 1 | | 30 | | | | | | |
| Recent | | 64 | | | | | | |
| Unique to | | 110 | | | | | | |
| U95Av2 Also run on U133A[2] | | 118 | 50 | 68 | 13 | 35 | | |
| TOTAL | | | | | | | | |
| U133A | 57 | 146 | 74 | 52 | 28 | 46 | | |
| Also run on U95[2] | | 93 | | | | | | |
| TOTAL | 91 | 146 | | | | | | |

[1]As of July 2004; refers to relapse tumor samples and nonrelapse tumor samples.

[2]For the comparison of cell-specific genes derived following the methods of Example 1 using U95Av2 GeneChips, 110 patients analyzed on the U95Av2 platform were compared to 93 independent patients analyzed on the U133A platform. T-statistics for the four cell types were determined and compared as described in Section 5.

TABLE 5

Agreement Analysis of Cell-type Specific Gene Expression as determined using U95A GeneChip expression data (Example 1) and additional samples and by U113A GeneChip Expression data

| Cell Type | Pearson Correlation Coefficient for U95 vs. U133 with probability | |
|---|---|---|
| | t-statistic >2.4 | No t-statistic cutoff |
| TUMOR EPITHELIAL CELLS | 0.827 | 0.51 |
| | p < 2.23e**−16 | p < 2.2e**−16 |
| BPH EPITHELIAL CELLS | 0.723 | 0.366 |
| | p < 2.2e**−16 | p < 2.2e**−16 |
| STROMA CELLS | 0.937 | 0.734 |
| | p < 2.2e**−16 | p < 2.2e**−16 |
| DILATED CYSTIC GLAND EIPTHELIAL CELLS | 0.750 | 0.323 |
| | p < 7.4e**−13 | p < 2.2e**−16 |

TABLE 6

Identification of 1098 probe sets that are significantly differentially expressed in early relapse Prostate Cancer by Cell-type based on analysis of 146 U133A GeneChips. False discovery rates are in parentheses.

SAMPLES

| | |
|---|---|
| Relapsed within 2 years | 28 |
| NonRelapsed tumors (2-3 years) | 46 |
| Control: tissue from relapsed cases | 46 |
| Control: tissue from nonrelapsed cases | 26 |
| TOTAL | 146 |

RESULTS

Tumor cells of relapse tumor vs. nonrelapsed tumor

| | |
|---|---|
| 394 | significant differences in gene expression |
| 110 (0.22) | increased in expression |
| 284 (0.19) | decreased in expression |

Stromal cells of relapse tumor vs. nonrelapsed tumor

| | |
|---|---|
| 704 | significant differences |
| 78 (0.22) | increased in expression |
| 626 (0.06) | decreased in expression |

BPH cells - no significant differences

TABLE 7

| Data Set | Classification success % |
|---|---|
| 146 U133A Arrays | 67.75% of relapse and nonrelapse cases correct |
| | 80% of relapse cases correct |
| Probe Sets Common to U133A & U95 | 69.89% |

TABLE 9

Top genes identified as up- and down-regulated in prostate tumor cells of relapse patients, calculated by linear regression, including all samples with prostate cancer. (negative numbers for down-regulated. −1 is best)

| Affymetrix ProbeID | T statistic | Rank | Large differences |
|---|---|---|---|
| 218509_at | 5.44 | 1 | D |
| 220587_s_at | 5.22 | 2 | |
| 208579_x_at | 4.83 | 3 | |
| 208490_x_at | 4.56 | 4 | |
| 209806_at | 4.55 | 5 | |
| 208527_x_at | 4.55 | 6 | |
| 208676_s_at | 4.51 | 7 | D |
| 218186_at | 4.26 | 8 | |
| 209873_s_at | 4.23 | 9 | |
| 202148_s_at | 4.23 | 10 | D |
| 201618_x_at | 4.13 | 11 | |
| 209391_at | 4.07 | 12 | |
| 200003_s_at | 3.95 | 13 | |
| 212445_s_at | 3.94 | 14 | |
| 64899_at | 3.91 | 15 | |
| 220584_at | 3.87 | 16 | |
| 202041_s_at | 3.86 | 17 | |
| 211982_x_at | 3.86 | 18 | D |
| 215690_x_at | 3.86 | 19 | |
| 218275_at | 3.84 | 20 | |
| 202871_at | 3.8 | 21 | |
| 222067_x_at | 3.79 | 22 | |
| 210243_s_at | 3.71 | 23 | |
| 32837_at | 3.62 | 24 | |
| 211716_x_at | 3.61 | 25 | D |
| 208629_s_at | 3.6 | 26 | |
| 213843_x_at | 3.6 | 27 | |
| 211899_s_at | 3.59 | 28 | |
| 203103_s_at | 3.56 | 29 | |
| 219798_s_at | 3.55 | 30 | |
| 215812_s_at | 3.54 | 31 | |
| 211060_x_at | 3.52 | 32 | |
| 208684_at | 3.51 | 33 | D |
| 206491_s_at | 3.5 | 34 | |
| 218261_at | 3.5 | 35 | |
| 203720_s_at | 3.46 | 36 | |
| 201115_at | 3.45 | 37 | |
| 201388_at | 3.45 | 38 | |
| 220189_s_at | 3.44 | 39 | |
| 208308_s_at | 3.44 | 40 | D |
| 210983_s_at | 3.43 | 41 | D |
| 219360_s_at | 3.41 | 42 | |
| 201378_s_at | 3.37 | 43 | D |
| 202779_s_at | 3.37 | 44 | D |
| 203287_at | 3.36 | 45 | |
| 201168_x_at | 3.35 | 46 | |
| 202525_at | 3.35 | 47 | |
| 210854_x_at | 3.35 | 48 | |
| 208613_s_at | 3.34 | 49 | |
| 209696_at | 3.31 | 50 | |
| 217294_s_at | 3.31 | 51 | D |
| 214784_x_at | 3.31 | 52 | |
| 219223_at | 3.31 | 53 | |
| 200852_x_at | 3.31 | 54 | |
| 209844_at | 3.3 | 55 | |
| 208546_x_at | 3.29 | 56 | |
| 204934_s_at | 3.27 | 57 | |
| 202676_x_at | 3.25 | 58 | |
| 212125_at | 3.25 | 59 | |
| 201771_at | 3.24 | 60 | |
| 202247_s_at | 3.21 | 61 | D |
| 200997_at | 3.21 | 62 | |
| 207722_s_at | 3.21 | 63 | |
| 201709_s_at | 3.2 | 64 | |
| 203228_at | 3.19 | 65 | |
| 204109_s_at | 3.19 | 66 | |
| M33197_5_at | 3.19 | 67 | |
| 208824_x_at | 3.17 | 68 | |
| 212282_at | 3.17 | 69 | |
| 209878_s_at | 3.15 | 70 | |
| 210761_s_at | 3.15 | 71 | |
| 208751_at | 3.15 | 72 | |
| 202758_s_at | 3.14 | 73 | |
| 218164_at | 3.14 | 74 | |

TABLE 9-continued

Top genes identified as up- and down-regulated in prostate
tumor cells of relapse patients, calculated by linear
regression, including all samples with prostate cancer.
(negative numbers for down-regulated. −1 is best)

| Affymetrix ProbeID | T statistic | Rank | Large differences |
|---|---|---|---|
| 201548_s_at | 3.14 | 75 | |
| 209231_s_at | 3.14 | 76 | |
| 214501_s_at | 3.13 | 77 | |
| 58696_at | 3.13 | 78 | |
| 212081_x_at | 3.12 | 79 | |
| 210470_x_at | 3.11 | 80 | D |
| 212563_at | 3.1 | 81 | |
| 202790_at | 3.1 | 82 | |
| 214336_s_at | 3.09 | 83 | |
| 65517_at | 3.09 | 84 | |
| 208523_x_at | 3.09 | 85 | D |
| 208856_x_at | 3.09 | 86 | |
| 200895_s_at | 3.09 | 87 | |
| 208698_s_at | 3.08 | 88 | |
| 208621_s_at | 3.08 | 89 | |
| 202545_at | 3.07 | 90 | |
| 203952_at | 3.06 | 91 | |
| 201946_s_at | 3.06 | 92 | |
| 212772_s_at | 3.05 | 93 | |
| 217791_s_at | 3.05 | 94 | |
| 217784_at | 3.05 | 95 | |
| 201526_at | 3.04 | 96 | |
| 220707_s_at | 3.04 | 97 | |
| 200950_at | 3.03 | 98 | D |
| 212002_at | 3.03 | 99 | |
| 218893_at | 3.03 | 100 | |
| 201587_s_at | 3.03 | 101 | |
| 208693_s_at | 3.03 | 102 | |
| 209516_at | 3.03 | 103 | |
| 217754_at | 3.02 | 104 | |
| 209592_s_at | 3.02 | 105 | |
| 202290_at | 3.02 | 106 | |
| 218695_at | 3.01 | 107 | |
| 220964_s_at | 3.01 | 108 | |
| 213059_at | 3 | 109 | |
| 204480_s_at | 3 | 110 | |
| 212845_at | −3 | −284 | |
| 212535_at | −3.01 | −283 | |
| 212150_at | −3.01 | −282 | |
| 202000_at | −3.01 | −281 | |
| 202133_at | −3.01 | −280 | |
| 201153_s_at | −3.01 | −279 | |
| 200673_at | −3.02 | −278 | |
| 204655_at | −3.02 | −277 | |
| 209658_at | −3.02 | −276 | |
| 213044_at | −3.02 | −275 | |
| 209656_s_at | −3.03 | −274 | |
| 221788_at | −3.03 | −273 | D |
| 209465_x_at | −3.03 | −272 | |
| 212956_at | −3.04 | −271 | |
| 220617_s_at | −3.04 | −270 | D |
| 204345_at | −3.04 | −269 | |
| 203017_s_at | −3.05 | −268 | |
| 203636_at | −3.06 | −267 | |
| 201865_x_at | −3.06 | −266 | |
| 202269_x_at | −3.07 | −265 | |
| 213338_at | −3.07 | −264 | |
| 200762_at | −3.07 | −263 | D |
| 208131_at | −3.08 | −262 | |
| 204753_s_at | −3.09 | −261 | |
| 213158_at | −3.1 | −260 | |
| 211577_s_at | −3.1 | −259 | |
| 211562_s_at | −3.1 | −258 | D |
| 212226_s_at | −3.1 | −257 | |
| 213005_s_at | −3.1 | −256 | |
| 205348_s_at | −3.11 | −255 | |
| 823_at | −3.11 | −254 | |
| 212713_at | −3.11 | −253 | D |
| 200696_s_at | −3.11 | −252 | |
| 204359_at | −3.11 | −251 | |
| 209747_at | −3.11 | −250 | |
| 207876_s_at | −3.11 | −249 | |
| 213878_at | −3.12 | −248 | |
| 211126_s_at | −3.12 | −247 | |
| 211813_x_at | −3.12 | −246 | D |
| 208030_s_at | −3.13 | −245 | |
| 218082_at | −3.13 | −244 | |
| 210764_s_at | −3.13 | −243 | D |
| 200985_s_at | −3.14 | −242 | |
| 209075_s_at | −3.14 | −241 | |
| 209473_at | −3.14 | −240 | |
| 212557_at | −3.14 | −239 | D |
| 212149_at | −3.14 | −238 | |
| 206070_s_at | −3.15 | −237 | |
| 221523_s_at | −3.15 | −236 | D |
| 209297_at | −3.15 | −235 | |
| 212288_at | −3.15 | −234 | |
| 213306_at | −3.15 | −233 | |
| 202074_at | −3.16 | −232 | |
| 203156_at | −3.16 | −231 | |
| 215016_x_at | −3.16 | −230 | |
| 201200_at | −3.17 | −229 | |
| 207738_s_at | −3.17 | −228 | |
| 202037_s_at | −3.17 | −227 | D |
| 209129_at | −3.18 | −226 | |
| 217437_s_at | −3.18 | −225 | |
| 202026_at | −3.18 | −224 | |
| 217362_x_at | −3.18 | −223 | |
| 219747_at | −3.18 | −222 | |
| 209466_x_at | −3.19 | −221 | |
| 200791_s_at | −3.19 | −220 | |
| 202522_at | −3.19 | −219 | |
| 213110_s_at | −3.2 | −218 | |
| 202266_at | −3.2 | −217 | D |
| 209542_x_at | −3.2 | −216 | |
| 201603_at | −3.21 | −215 | |
| 202440_s_at | −3.21 | −214 | |
| 212423_at | −3.22 | −213 | |
| 204963_at | −3.22 | −212 | |
| 209568_s_at | −3.22 | −211 | |
| 211984_at | −3.22 | −210 | |
| 213411_at | −3.23 | −209 | |
| 201150_s_at | −3.23 | −208 | |
| 201336_at | −3.23 | −207 | |
| 201021_s_at | −3.23 | −206 | |
| 214752_x_at | −3.23 | −205 | |
| 209550_at | −3.23 | −204 | |
| 221760_at | −3.24 | −203 | |
| 200899_s_at | −3.24 | −202 | |
| 206332_s_at | −3.24 | −201 | |
| 211737_x_at | −3.24 | −200 | |
| 208747_s_at | −3.24 | −199 | |
| 204412_s_at | −3.24 | −198 | |
| 209770_at | −3.25 | −197 | |
| 206481_s_at | −3.25 | −196 | |
| 212549_at | −3.25 | −195 | |
| 211986_at | −3.26 | −194 | |
| 203687_at | −3.26 | −193 | |
| 212551_at | −3.26 | −192 | |
| 201152_s_at | −3.26 | −191 | |
| 211962_s_at | −3.26 | −190 | |
| 203632_s_at | −3.27 | −189 | |
| 208944_at | −3.27 | −188 | |
| 212558_at | −3.27 | −187 | |
| 201185_at | −3.27 | −186 | |
| 219055_at | −3.27 | −185 | |
| 219647_at | −3.28 | −184 | |
| 203705_s_at | −3.28 | −183 | |
| 205383_s_at | −3.28 | −182 | |
| 204462_s_at | −3.29 | −181 | |
| 213203_at | −3.29 | −180 | |
| 219685_at | −3.3 | −179 | |
| 202646_s_at | −3.3 | −178 | |
| 205564_at | −3.3 | −177 | |

TABLE 9-continued

Top genes identified as up- and down-regulated in prostate tumor cells of relapse patients, calculated by linear regression, including all samples with prostate cancer. (negative numbers for down-regulated. −1 is best)

| Affymetrix ProbeID | T statistic | Rank | Large differences |
|---|---|---|---|
| 203339_at | −3.31 | −176 | |
| 204939_s_at | −3.31 | −175 | |
| 202506_at | −3.31 | −174 | |
| 218718_at | −3.32 | −173 | D |
| 203065_s_at | −3.33 | −172 | |
| 206938_at | −3.33 | −171 | |
| 205051_s_at | −3.33 | −170 | |
| 212063_at | −3.34 | −169 | |
| 216215_s_at | −3.34 | −168 | |
| 213675_at | −3.34 | −167 | |
| 35776_at | −3.36 | −166 | |
| 212690_at | −3.38 | −165 | |
| 204400_at | −3.38 | −164 | |
| 202157_s_at | −3.39 | −163 | |
| 209090_s_at | −3.39 | −162 | |
| 204135_at | −3.39 | −161 | |
| 201409_s_at | −3.4 | −160 | |
| 208158_s_at | −3.4 | −159 | |
| 220911_s_at | −3.42 | −158 | |
| 201957_at | −3.42 | −157 | |
| 209616_s_at | −3.42 | −156 | D |
| 220751_s_at | −3.42 | −155 | |
| 209291_at | −3.42 | −154 | |
| 200986_at | −3.44 | −153 | |
| 206874_s_at | −3.45 | −152 | |
| 209210_s_at | −3.45 | −151 | |
| 204069_at | −3.46 | −150 | |
| 214937_x_at | −3.46 | −149 | |
| 201667_at | −3.46 | −148 | |
| 202362_at | −3.46 | −147 | |
| 201368_at | −3.47 | −146 | |
| 207977_s_at | −3.48 | −145 | |
| 201536_at | −3.48 | −144 | |
| 212829_at | −3.48 | −143 | |
| 210299_s_at | −3.49 | −142 | D |
| 212230_at | −3.49 | −141 | |
| 219167_at | −3.49 | −140 | |
| 209379_s_at | −3.49 | −139 | |
| 208791_at | −3.49 | −138 | D |
| 212233_at | −3.5 | −137 | D |
| 204820_s_at | −3.51 | −136 | |
| 202995_s_at | −3.51 | −135 | |
| 200931_s_at | −3.51 | −134 | |
| 203566_s_at | −3.52 | −133 | D |
| 221816_s_at | −3.53 | −132 | |
| 203680_at | −3.53 | −131 | |
| 212865_s_at | −3.54 | −130 | |
| 218217_at | −3.55 | −129 | |
| 218824_at | −3.56 | −128 | |
| 212111_at | −3.56 | −127 | |
| 212148_at | −3.57 | −126 | |
| 217766_s_at | −3.57 | −125 | |
| 203903_s_at | −3.58 | −124 | |
| 215000_s_at | −3.59 | −123 | |
| 208792_s_at | −3.59 | −122 | |
| 206580_s_at | −3.59 | −121 | |
| 213068_at | −3.6 | −120 | |
| 209337_at | −3.61 | −119 | |
| 208667_s_at | −3.61 | −118 | |
| 213924_at | −3.61 | −117 | |
| 204931_at | −3.62 | −116 | |
| 217792_at | −3.62 | −115 | |
| 202501_at | −3.63 | −114 | |
| 201300_s_at | −3.63 | −113 | |
| 204570_at | −3.65 | −112 | |
| 202946_s_at | −3.65 | −111 | |
| 212097_at | −3.66 | −110 | |
| 200953_s_at | −3.68 | −109 | D |
| 209540_at | −3.7 | −108 | |
| 204754_at | −3.71 | −107 | D |
| 203420_at | −3.72 | −106 | |
| 200816_s_at | −3.72 | −105 | |
| 202172_at | −3.74 | −104 | |
| 212120_at | −3.74 | −103 | |
| 205480_s_at | −3.75 | −102 | |
| 204083_s_at | −3.75 | −101 | |
| 204464_s_at | −3.77 | −100 | |
| 221748_s_at | −3.77 | −99 | |
| 212419_at | −3.79 | −98 | |
| 203037_s_at | −3.79 | −97 | |
| 203640_at | −3.79 | −96 | |
| 212586_at | −3.79 | −95 | |
| 202073_at | −3.8 | −94 | |
| 209496_at | −3.82 | −93 | |
| 212764_at | −3.82 | −92 | D |
| 212043_at | −3.82 | −91 | D |
| 201289_at | −3.83 | −90 | |
| 200621_at | −3.83 | −89 | D |
| 207016_s_at | −3.83 | −88 | |
| 205624_at | −3.84 | −87 | |
| 207547_s_at | −3.84 | −86 | |
| 201893_x_at | −3.85 | −85 | |
| 201787_at | −3.86 | −84 | |
| 211323_s_at | −3.87 | −83 | D |
| 202401_s_at | −3.88 | −82 | |
| 207761_s_at | −3.88 | −81 | |
| 201121_s_at | −3.89 | −80 | D |
| 207071_s_at | −3.89 | −79 | |
| 204793_at | −3.9 | −78 | |
| 218162_at | −3.9 | −77 | |
| 212914_at | −3.9 | −76 | |
| 218730_s_at | −3.91 | −75 | D |
| 201012_at | −3.91 | −74 | D |
| 209541_at | −3.91 | −73 | |
| 200911_s_at | −3.91 | −72 | |
| 201560_at | −3.93 | −71 | |
| 204041_at | −3.93 | −70 | |
| 218698_at | −3.94 | −69 | |
| 201272_at | −3.95 | −68 | |
| 210297_s_at | −3.95 | −67 | |
| 204393_s_at | −3.96 | −66 | D |
| 207961_x_at | −3.98 | −65 | |
| 221584_s_at | −3.99 | −64 | |
| 212509_s_at | −4.02 | −63 | |
| 212730_at | −4.02 | −62 | |
| 218421_at | −4.03 | −61 | |
| 209487_at | −4.03 | −60 | |
| 213071_at | −4.03 | −59 | D |
| 209118_s_at | −4.04 | −58 | |
| 218298_s_at | −4.05 | −57 | |
| 203404_at | −4.06 | −56 | D |
| 203706_s_at | −4.06 | −55 | |
| 213093_at | −4.06 | −54 | |
| 202992_at | −4.09 | −53 | D |
| 201408_at | −4.09 | −52 | |
| 217922_at | −4.1 | −51 | |
| 218087_s_at | −4.1 | −50 | D |
| 218047_at | −4.14 | −49 | |
| 200982_s_at | −4.14 | −48 | |
| 200907_s_at | −4.15 | −47 | |
| 202594_at | −4.15 | −46 | |
| 205364_at | −4.16 | −45 | |
| 212724_at | −4.18 | −44 | |
| 208848_at | −4.2 | −43 | |
| 202565_s_at | −4.25 | −42 | |
| 212757_s_at | −4.25 | −41 | |
| 208789_at | −4.28 | −40 | D |
| 203710_at | −4.31 | −39 | |
| 212195_at | −4.35 | −38 | |
| 203766_s_at | −4.35 | −37 | |
| 201061_s_at | −4.36 | −36 | |
| 213293_s_at | −4.36 | −35 | |
| 209651_at | −4.38 | −34 | |
| 212813_at | −4.41 | −33 | |

TABLE 9-continued

Top genes identified as up- and down-regulated in prostate tumor cells of relapse patients, calculated by linear regression, including all samples with prostate cancer. (negative numbers for down-regulated. −1 is best)

| Affymetrix ProbeID | T statistic | Rank | Large differences |
|---|---|---|---|
| 209687_at | −4.43 | −32 | |
| 202350_s_at | −4.44 | −31 | |
| 210987_x_at | −4.49 | −30 | |
| 202555_s_at | −4.55 | −29 | |
| 209286_at | −4.58 | −28 | |
| 205011_at | −4.58 | −27 | |
| 212077_at | −4.6 | −26 | |
| 218418_s_at | −4.64 | −25 | |
| 209948_at | −4.64 | −24 | D |
| 202228_s_at | −4.66 | −23 | |
| 217897_at | −4.66 | −22 | D |
| 209763_at | −4.67 | −21 | |
| 202994_s_at | −4.67 | −20 | |
| 207480_s_at | −4.67 | −19 | |
| 207430_s_at | −4.67 | −18 | D |
| 201540_at | −4.72 | −17 | |
| 216231_s_at | −4.72 | −16 | |
| 203951_at | −4.72 | −15 | |
| 209288_s_at | −4.75 | −14 | |
| 221958_s_at | −4.76 | −13 | |
| 201431_s_at | −4.8 | −12 | |
| 200974_at | −4.82 | −11 | |
| 221667_s_at | −4.99 | −10 | |
| 202432_at | −5.02 | −9 | |
| 200897_s_at | −5.15 | −8 | |
| 209074_s_at | −5.16 | −7 | D |
| 201891_s_at | −5.19 | −6 | |
| 201497_x_at | −5.23 | −5 | |
| 202274_at | −5.72 | −4 | |
| 200795_at | −5.89 | −3 | |
| 201022_s_at | −5.93 | −2 | |
| 210986_s_at | −6.14 | −1 | |

TABLE 10

Top genes identified as up- and down-regulated in prostate stroma of relapse patients, calculated by linear regression, including all samples with prostate cancer. (negative numbers for down-regulated. −1 is best)

| Affymetrix number Probe Set Name | T statistic | Rank | Probe Set Name |
|---|---|---|---|
| | | | D |
| 204436_at | 4.19 | 1 | |
| 212076_at | 3.94 | 2 | |
| 202401_s_at | 3.93 | 3 | |
| 211323_s_at | 3.85 | 4 | D |
| 211991_s_at | 3.81 | 5 | |
| 212713_at | 3.77 | 6 | D |
| 207547_s_at | 3.73 | 7 | |
| 209473_at | 3.68 | 8 | |
| 200953_s_at | 3.61 | 9 | D |
| 202501_at | 3.61 | 10 | |
| 205988_at | 3.59 | 11 | |
| 212151_at | 3.57 | 12 | |
| 203735_x_at | 3.55 | 13 | |
| 205456_at | 3.51 | 14 | |
| 218525_s_at | 3.5 | 15 | |
| 208789_at | 3.49 | 16 | D |
| 204882_at | 3.48 | 17 | |
| 201148_s_at | 3.47 | 18 | |
| 207691_x_at | 3.47 | 19 | |
| 200610_s_at | 3.46 | 20 | |
| 215826_x_at | 3.46 | 21 | |
| 209582_s_at | 3.45 | 22 | D |

TABLE 10-continued

Top genes identified as up- and down-regulated in prostate stroma of relapse patients, calculated by linear regression, including all samples with prostate cancer. (negative numbers for down-regulated. −1 is best)

| Affymetrix number | T statistic | Rank | |
|---|---|---|---|
| 209071_s_at | 3.4 | 23 | 0 |
| 201080_at | 3.39 | 24 | |
| 210105_s_at | 3.39 | 25 | |
| 200621_at | 3.38 | 26 | D |
| 218581_at | 3.37 | 27 | |
| 209070_s_at | 3.35 | 28 | |
| 221958_s_at | 3.35 | 29 | |
| 211203_s_at | 3.35 | 30 | |
| 201893_x_at | 3.34 | 31 | |
| 205011_at | 3.34 | 32 | |
| 203853_s_at | 3.34 | 33 | |
| 221447_s_at | 3.34 | 34 | |
| 212972_x_at | 3.33 | 35 | |
| 214760_at | 3.3 | 36 | |
| 202048_s_at | 3.28 | 37 | |
| 217187_at | 3.27 | 38 | |
| 204754_at | 3.26 | 39 | D |
| 217362_x_at | 3.25 | 40 | |
| 210976_s_at | 3.25 | 41 | |
| 209057_x_at | 3.2 | 42 | D |
| 205405_at | 3.19 | 43 | |
| 200974_at | 3.19 | 44 | |
| 213958_at | 3.18 | 45 | |
| 204795_at | 3.17 | 46 | |
| 219035_s_at | 3.16 | 47 | |
| 217580_x_at | 3.16 | 48 | D |
| 209947_at | 3.15 | 49 | |
| 212822_at | 3.15 | 50 | |
| 217925_s_at | 3.15 | 51 | |
| 211697_x_at | 3.15 | 52 | D |
| 38521_at | 3.14 | 53 | |
| 204341_at | 3.14 | 54 | D |
| 216033_s_at | 3.14 | 55 | |
| 209646_x_at | 3.14 | 56 | |
| 208306_x_at | 3.13 | 57 | |
| 210444_at | 3.13 | 58 | |
| 209297_at | 3.13 | 59 | |
| 214738_s_at | 3.1 | 60 | |
| 202074_s_at | 3.1 | 61 | |
| 205482_x_at | 3.09 | 62 | |
| 201320_at | 3.09 | 63 | |
| 214694_at | 3.08 | 64 | |
| 212344_at | 3.08 | 65 | |
| 206868_at | 3.08 | 66 | |
| 211504_x_at | 3.08 | 67 | |
| 206057_x_at | 3.07 | 68 | |
| 219093_at | 3.07 | 69 | |
| 203950_s_at | 3.06 | 70 | |
| 200795_at | 3.06 | 71 | |
| 212239_at | 3.05 | 72 | |
| 211296_x_at | 3.05 | 73 | |
| 210288_at | 3.04 | 74 | |
| 205151_s_at | 3.03 | 75 | |
| 38149_at | 3.02 | 76 | |
| 211123_at | 3.02 | 77 | |
| 218338_at | 3.01 | 78 | |
| 217782_s_at | −2.5 | −626 | |
| 211972_x_at | −2.5 | −625 | |
| 220477_s_at | −2.5 | −624 | |
| 201485_s_at | −2.5 | −623 | |
| 203201_at | −2.51 | −622 | |
| 217950_at | −2.51 | −621 | |
| 209917_at | −2.51 | −620 | |
| 203164_at | −2.51 | −619 | |
| 218186_at | −2.51 | −618 | |
| 218617_at | −2.51 | −617 | |
| 203573_at | −2.51 | −616 | |
| 203721_s_at | −2.51 | −615 | |
| 201568_at | −2.51 | −614 | |
| 209110_s_at | −2.51 | −613 | |
| 209471_s_at | −2.51 | −612 | |
| 208721_s_at | −2.51 | −611 | |

TABLE 10-continued

Top genes identified as up- and down-regulated in prostate stroma of relapse patients, calculated by linear regression, including all samples with prostate cancer.
(negative numbers for down-regulated. −1 is best)

| Affymetrix number | T statistic | Rank | |
|---|---|---|---|
| 208649_s_at | −2.52 | −610 | |
| 212168_at | −2.52 | −609 | |
| 209377_s_at | −2.52 | −608 | |
| 217870_s_at | −2.52 | −607 | |
| 218557_at | −2.52 | −606 | |
| 209177_at | −2.52 | −605 | |
| 202868_s_at | −2.52 | −604 | |
| 209472_at | −2.52 | −603 | |
| 214243_s_at | −2.52 | −602 | |
| 218681_s_at | −2.52 | −601 | |
| 217755_at | −2.53 | −600 | |
| 221587_s_at | −2.53 | −599 | |
| 220945_x_at | −2.53 | −598 | |
| 211070_x_at | −2.53 | −597 | |
| 216958_s_at | −2.53 | −596 | |
| 213399_x_at | −2.53 | −595 | |
| 209228_x_at | −2.53 | −594 | |
| 201077_s_at | −2.53 | −593 | |
| 218434_s_at | −2.53 | −592 | |
| 218795_at | −2.54 | −591 | |
| 202769_at | −2.54 | −590 | |
| 201219_at | −2.54 | −589 | |
| 200925_at | −2.54 | −588 | |
| 211596_s_at | −2.54 | −587 | |
| 208650_s_at | −2.54 | −586 | |
| 221570_s_at | −2.54 | −585 | |
| 202343_x_at | −2.54 | −584 | |
| 202758_s_at | −2.54 | −583 | |
| 212508_at | −2.54 | −582 | |
| 204246_s_at | −2.54 | −581 | |
| 217973_at | −2.55 | −580 | |
| 216532_x_at | −2.55 | −579 | |
| 201705_at | −2.55 | −578 | |
| 221939_at | −2.55 | −577 | |
| 222075_s_at | −2.55 | −576 | |
| 219203_at | −2.55 | −575 | |
| 215091_s_at | −2.56 | −574 | |
| 209696_at | −2.56 | −573 | |
| 217875_s_at | −2.56 | −572 | |
| 217976_s_at | −2.56 | −571 | |
| 212449_s_at | −2.56 | −570 | |
| 201003_x_at | −2.56 | −569 | |
| 200078_s_at | −2.57 | −568 | |
| 202166_s_at | −2.57 | −567 | |
| 203007_x_at | −2.57 | −566 | |
| 202697_at | −2.57 | −565 | |
| 221434_s_at | −2.57 | −564 | |
| 215947_s_at | −2.57 | −563 | |
| 200819_s_at | −2.57 | −562 | |
| 209364_at | −2.57 | −561 | |
| 218685_s_at | −2.57 | −560 | |
| 204168_at | −2.58 | −559 | |
| 203041_s_at | −2.58 | −558 | |
| 209389_x_at | −2.58 | −557 | |
| 208930_s_at | −2.58 | −556 | |
| 203351_s_at | −2.58 | −555 | |
| 209171_at | −2.58 | −554 | |
| 201698_s_at | −2.58 | −553 | |
| 206066_s_at | −2.58 | −552 | |
| 213828_x_at | −2.59 | −551 | |
| 214522_x_at | −2.59 | −550 | |
| 203360_s_at | −2.59 | −549 | |
| 206491_s_at | −2.59 | −548 | |
| 219176_at | −2.59 | −547 | |
| 212833_at | −2.59 | −546 | |
| 201625_s_at | −2.59 | −545 | |
| 204922_at | −2.59 | −544 | |
| 207088_s_at | −2.59 | −543 | |
| 207707_s_at | −2.59 | −542 | |
| 209625_at | −2.59 | −541 | |
| 202121_s_at | −2.59 | −540 | |
| 221041_s_at | −2.6 | −539 | |
| 210387_at | −2.6 | −538 | |
| 218095_s_at | −2.6 | −537 | D |
| 215726_s_at | −2.6 | −536 | |
| 204170_s_at | −2.6 | −535 | |
| 201624_at | −2.6 | −534 | |
| 213716_s_at | −2.6 | −533 | |
| 206469_x_at | −2.6 | −532 | |
| 205542_at | −2.6 | −531 | |
| 217800_s_at | −2.6 | −530 | |
| 208932_at | −2.6 | −529 | |
| 200777_s_at | −2.6 | −528 | |
| 201273_s_at | −2.61 | −527 | |
| 203646_at | −2.61 | −526 | |
| 208788_at | −2.61 | −525 | |
| 41047_at | −2.61 | −524 | |
| 220547_s_at | −2.61 | −523 | |
| 201900_s_at | −2.61 | −522 | |
| 212204_at | −2.61 | −521 | |
| 212006_at | −2.61 | −520 | |
| 217752_s_at | −2.61 | −519 | |
| 221637_s_at | −2.61 | −518 | |
| 210927_x_at | −2.61 | −517 | |
| 209014_at | −2.61 | −516 | |
| 217850_at | −2.61 | −515 | |
| 202545_at | −2.61 | −514 | |
| 209407_s_at | −2.61 | −513 | |
| 203030_s_at | −2.61 | −512 | |
| 214765_s_at | −2.62 | −511 | |
| 204427_s_at | −2.62 | −510 | |
| 204050_s_at | −2.62 | −509 | |
| 214542_x_at | −2.62 | −508 | |
| 203511_s_at | −2.63 | −507 | |
| 209694_at | −2.63 | −506 | |
| 209482_at | −2.63 | −505 | |
| 217770_at | −2.63 | −504 | |
| 205597_at | −2.63 | −503 | |
| 200790_at | −2.63 | −502 | |
| 220334_at | −2.63 | −501 | |
| 201095_at | −2.64 | −500 | |
| 208651_x_at | −2.64 | −499 | D |
| 205449_at | −2.64 | −498 | |
| 209100_at | −2.64 | −497 | |
| 216088_s_at | −2.64 | −496 | |
| 201114_x_at | −2.64 | −495 | |
| 210541_s_at | −2.65 | −494 | |
| 213892_s_at | −2.65 | −493 | |
| 202737_s_at | −2.65 | −492 | |
| 218341_at | −2.65 | −491 | D |
| 210024_s_at | −2.65 | −490 | |
| 201177_s_at | −2.65 | −489 | |
| 220587_s_at | −2.65 | −488 | |
| 213971_s_at | −2.65 | −487 | |
| 213738_s_at | −2.66 | −486 | |
| 212246_at | −2.66 | −485 | |
| 216230_x_at | −2.66 | −484 | |
| 203857_s_at | −2.66 | −483 | |
| 212191_x_at | −2.66 | −482 | |
| 202890_at | −2.66 | −481 | |
| 209217_s_at | −2.66 | −480 | |
| 202433_at | −2.66 | −479 | |
| 201600_at | −2.66 | −478 | |
| 209340_at | −2.67 | −477 | |
| 208024_s_at | −2.67 | −476 | |
| 202993_at | −2.67 | −475 | |
| 200852_x_at | −2.67 | −474 | |
| 204212_at | −2.67 | −473 | |
| 203667_at | −2.67 | −472 | |
| 213175_s_at | −2.68 | −471 | |
| 211423_s_at | −2.68 | −470 | |
| 213735_s_at | −2.68 | −469 | |
| 209808_x_at | −2.68 | −468 | |
| 218283_at | −2.68 | −467 | |

TABLE 10-continued

Top genes identified as up- and down-regulated in prostate stroma of relapse patients, calculated by linear regression, including all samples with prostate cancer. (negative numbers for down-regulated. −1 is best)

| Affymetrix number | T statistic | Rank | |
|---|---|---|---|
| 203272_s_at | −2.68 | −466 | |
| 202139_at | −2.69 | −465 | |
| 220192_x_at | −2.69 | −464 | |
| 217861_s_at | −2.69 | −463 | |
| 217868_s_at | −2.69 | −462 | |
| 200960_x_at | −2.69 | −461 | |
| 202927_at | −2.69 | −460 | |
| 219075_at | −2.69 | −459 | |
| 203791_at | −2.69 | −458 | |
| 218074_at | −2.69 | −457 | |
| 218320_s_at | −2.69 | −456 | |
| 200903_s_at | −2.7 | −455 | |
| 222256_s_at | −2.7 | −454 | |
| 200710_at | −2.7 | −453 | |
| 201019_s_at | −2.71 | −452 | |
| 218548_x_at | −2.71 | −451 | |
| 217942_at | −2.71 | −450 | |
| 209911_x_at | −2.71 | −449 | |
| 1729_at | −2.71 | −448 | |
| 213726_x_at | −2.71 | −447 | |
| 203478_at | −2.71 | −446 | |
| 212767_at | −2.72 | −445 | |
| 217898_at | −2.72 | −444 | |
| 213133_s_at | −2.72 | −443 | |
| 218789_s_at | −2.72 | −442 | |
| 221566_s_at | −2.72 | −441 | |
| 202122_s_at | −2.72 | −440 | |
| 207063_at | −2.72 | −439 | |
| 203954_x_at | −2.72 | −438 | |
| 209080_x_at | −2.72 | −437 | |
| 202942_at | −2.72 | −436 | |
| 209797_at | −2.73 | −435 | |
| 212255_s_at | −2.73 | −434 | |
| 213581_at | −2.73 | −433 | |
| 212680_x_at | −2.73 | −432 | |
| 216905_s_at | −2.73 | −431 | |
| 218732_at | −2.73 | −430 | |
| 209478_at | −2.73 | −429 | |
| 218216_x_at | −2.74 | −428 | |
| 202457_s_at | −2.74 | −427 | |
| 205780_at | −2.74 | −426 | |
| 203034_s_at | −2.74 | −425 | |
| 209063_x_at | −2.74 | −424 | |
| 217761_at | −2.74 | −423 | D |
| 208864_s_at | −2.74 | −422 | |
| 201963_at | −2.75 | −421 | |
| 201543_s_at | −2.75 | −420 | |
| 201619_at | −2.75 | −419 | |
| 209076_s_at | −2.75 | −418 | |
| 202308_at | −2.75 | −417 | |
| 211404_s_at | −2.75 | −416 | |
| 204340_at | −2.75 | −415 | |
| 220980_s_at | −2.76 | −414 | |
| 215952_s_at | −2.76 | −413 | |
| 201791_s_at | −2.76 | −412 | |
| 216308_x_at | −2.76 | −411 | |
| 204231_s_at | −2.76 | −410 | |
| 213061_s_at | −2.76 | −409 | |
| 218652_s_at | −2.76 | −408 | |
| 206656_s_at | −2.76 | −407 | |
| 213190_at | −2.76 | −406 | |
| 201923_at | −2.76 | −405 | |
| 209605_at | −2.76 | −404 | |
| 218192_at | −2.76 | −403 | |
| 218872_at | −2.76 | −402 | |
| 209114_at | −2.76 | −401 | D |
| 218447_at | −2.77 | −400 | |
| 202839_s_at | −2.77 | −399 | |
| 207431_s_at | −2.77 | −398 | |
| 214274_s_at | −2.77 | −397 | |
| 215631_s_at | −2.77 | −396 | |
| 204608_at | −2.77 | −395 | |
| 216483_s_at | −2.77 | −394 | |
| 218533_s_at | −2.77 | −393 | |
| 221437_s_at | −2.77 | −392 | |
| 208653_s_at | −2.78 | −391 | |
| 217956_s_at | −2.78 | −390 | |
| 211558_s_at | −2.78 | −389 | |
| 204084_s_at | −2.78 | −388 | D |
| 209825_s_at | −2.78 | −387 | |
| 209130_at | −2.78 | −386 | |
| 204160_s_at | −2.78 | −385 | |
| 204017_at | −2.78 | −384 | |
| 217930_s_at | −2.78 | −383 | |
| 207168_s_at | −2.78 | −382 | |
| 202525_at | −2.78 | −381 | |
| 204985_s_at | −2.78 | −380 | |
| 214112_s_at | −2.79 | −379 | |
| 215779_s_at | −2.79 | −378 | D |
| 218086_at | −2.79 | −377 | |
| 214882_s_at | −2.79 | −376 | |
| 214092_x_at | −2.79 | −375 | |
| 219117_s_at | −2.79 | −374 | |
| 202406_s_at | −2.79 | −373 | |
| 203373_at | −2.79 | −372 | |
| 217720_at | −2.79 | −371 | |
| 210825_s_at | −2.79 | −370 | |
| 218203_at | −2.79 | −369 | D |
| 202477_s_at | −2.8 | −368 | |
| 221512_at | −2.8 | −367 | |
| 201338_x_at | −2.8 | −366 | |
| 212116_at | −2.8 | −365 | |
| 206352_s_at | −2.8 | −364 | |
| 201066_at | −2.8 | −363 | |
| 206302_s_at | −2.81 | −362 | |
| 201740_at | −2.81 | −361 | |
| 201284_s_at | −2.81 | −360 | |
| 200805_at | −2.81 | −359 | |
| 204387_x_at | −2.81 | −358 | |
| 202130_at | −2.81 | −357 | |
| 204295_at | −2.82 | −356 | |
| 202708_s_at | −2.82 | −355 | |
| 202428_x_at | −2.82 | −354 | |
| 214107_x_at | −2.82 | −353 | |
| 217803_at | −2.82 | −352 | |
| 205329_s_at | −2.82 | −351 | |
| 204616_at | −2.82 | −350 | |
| 207721_x_at | −2.83 | −349 | |
| 200598_s_at | −2.83 | −348 | |
| 202429_s_at | −2.83 | −347 | |
| 211052_s_at | −2.83 | −346 | |
| 214214_s_at | −2.83 | −345 | D |
| 209132_s_at | −2.83 | −344 | |
| 213246_at | −2.84 | −343 | |
| 219920_s_at | −2.84 | −342 | |
| 203931_s_at | −2.84 | −341 | |
| 204934_s_at | −2.84 | −340 | |
| 209213_at | −2.84 | −339 | D |
| 221567_at | −2.84 | −338 | |
| 200620_at | −2.85 | −337 | |
| 201033_s_at | −2.85 | −336 | |
| 208826_x_at | −2.85 | −335 | |
| 204386_s_at | −2.85 | −334 | |
| 219061_s_at | −2.85 | −333 | |
| 203042_at | −2.85 | −332 | |
| 214455_at | −2.85 | −331 | D |
| 201745_at | −2.85 | −330 | |
| 212032_s_at | −2.85 | −329 | |
| 74694_s_at | −2.85 | −328 | |
| 201411_s_at | −2.86 | −327 | |
| 213152_s_at | −2.86 | −326 | |
| 209222_s_at | −2.86 | −325 | |
| 205353_s_at | −2.86 | −324 | |
| 213026_at | −2.86 | −323 | |

TABLE 10-continued

Top genes identified as up- and down-regulated in prostate stroma of relapse patients, calculated by linear regression, including all samples with prostate cancer. (negative numbers for down-regulated. −1 is best)

| Affymetrix number | T statistic | Rank | |
|---|---|---|---|
| 205164_at | −2.87 | −322 | |
| 212773_s_at | −2.87 | −321 | |
| 214875_x_at | −2.87 | −320 | |
| 204078_at | −2.87 | −319 | |
| 203192_at | −2.87 | −318 | |
| 210638_s_at | −2.87 | −317 | |
| 214257_s_at | −2.87 | −316 | |
| 211177_s_at | −2.87 | −315 | |
| 200969_at | −2.87 | −314 | |
| 222191_s_at | −2.88 | −313 | |
| 201612_at | −2.88 | −312 | |
| 218897_at | −2.88 | −311 | |
| 210059_s_at | −2.88 | −310 | |
| 210187_at | −2.88 | −309 | |
| 208405_s_at | −2.89 | −308 | |
| 218132_s_at | −2.89 | −307 | |
| 202138_x_at | −2.89 | −306 | |
| 207508_at | −2.9 | −305 | |
| 219929_s_at | −2.9 | −304 | |
| 218671_s_at | −2.9 | −303 | |
| 207275_s_at | −2.9 | −302 | |
| 220607_x_at | −2.9 | −301 | |
| 202836_s_at | −2.9 | −300 | |
| 205498_at | −2.9 | −299 | D |
| 213379_at | −2.91 | −298 | |
| 201714_at | −2.91 | −297 | |
| 218555_at | −2.91 | −296 | |
| 218327_s_at | −2.91 | −295 | |
| 203031_s_at | −2.92 | −294 | |
| 203892_at | −2.92 | −293 | |
| 221972_s_at | −2.92 | −292 | |
| 218101_s_at | −2.92 | −291 | |
| 221582_at | −2.92 | −290 | |
| 208918_s_at | −2.92 | −289 | |
| 209113_s_at | −2.92 | −288 | |
| 200740_s_at | −2.92 | −287 | |
| 211475_s_at | −2.93 | −286 | |
| 208941_s_at | −2.93 | −285 | |
| 205241_at | −2.93 | −284 | |
| 210633_x_at | −2.93 | −283 | |
| 218636_s_at | −2.93 | −282 | |
| 212790_x_at | −2.93 | −281 | |
| 59625_at | −2.93 | −280 | |
| 218996_at | −2.93 | −279 | |
| 218150_at | −2.93 | −278 | |
| 200863_s_at | −2.93 | −277 | |
| 205133_s_at | −2.93 | −276 | |
| 203437_at | −2.94 | −275 | |
| 209844_at | −2.94 | −274 | |
| 210041_s_at | −2.94 | −273 | |
| 219575_s_at | −2.94 | −272 | |
| 203524_s_at | −2.94 | −271 | |
| 213129_s_at | −2.94 | −270 | |
| 203219_s_at | −2.94 | −269 | |
| 215090_x_at | −2.94 | −268 | |
| 208817_at | −2.95 | −267 | |
| 217835_x_at | −2.95 | −266 | |
| 218220_at | −2.95 | −265 | |
| 202550_s_at | −2.95 | −264 | |
| 210097_s_at | −2.96 | −263 | |
| 201135_at | −2.96 | −262 | |
| 219807_x_at | −2.96 | −261 | |
| 213287_s_at | −2.96 | −260 | |
| 218046_s_at | −2.96 | −259 | |
| 58696_at | −2.96 | −258 | |
| 219119_at | −2.96 | −257 | |
| 40225_at | −2.96 | −256 | |
| 217824_at | −2.96 | −255 | |
| 221610_s_at | −2.96 | −254 | |
| 211730_s_at | −2.96 | −253 | |
| 222138_s_at | −2.96 | −252 | |
| 219806_s_at | −2.96 | −251 | |
| 201913_s_at | −2.97 | −250 | |
| 208818_s_at | −2.97 | −249 | |
| 217080_s_at | −2.97 | −248 | |
| 209759_s_at | −2.97 | −247 | |
| 49679_s_at | −2.97 | −246 | |
| 202632_at | −2.97 | −245 | |
| 219065_s_at | −2.97 | −244 | |
| 213423_x_at | −2.97 | −243 | |
| 219283_at | −2.97 | −242 | |
| 36936_at | −2.98 | −241 | |
| 203686_at | −2.98 | −240 | |
| 221847_at | −2.98 | −239 | D |
| 205489_at | −2.98 | −238 | |
| 202857_at | −2.98 | −237 | |
| 201955_at | −2.98 | −236 | |
| 218272_at | −2.98 | −235 | |
| 65884_at | −2.99 | −234 | |
| 204599_s_at | −2.99 | −233 | |
| 220597_s_at | −3 | −232 | |
| 202424_at | −3 | −231 | |
| 221688_s_at | −3 | −230 | |
| 202077_at | −3.01 | −229 | |
| 208658_at | −3.01 | −228 | |
| 218328_at | −3.01 | −227 | |
| 205110_s_at | −3.02 | −226 | |
| 219862_s_at | −3.02 | −225 | |
| 222125_s_at | −3.02 | −224 | |
| 218647_s_at | −3.02 | −223 | |
| 203594_at | −3.02 | −222 | |
| 206055_s_at | −3.02 | −221 | |
| 201903_at | −3.02 | −220 | |
| 218582_at | −3.02 | −219 | |
| 208722_s_at | −3.03 | −218 | |
| 201128_s_at | −3.03 | −217 | |
| 217772_s_at | −3.04 | −216 | |
| 204238_s_at | −3.04 | −215 | |
| 211940_x_at | −3.04 | −214 | |
| 209796_s_at | −3.04 | −213 | |
| 218206_x_at | −3.04 | −212 | |
| 220526_s_at | −3.04 | −211 | |
| 201588_at | −3.05 | −210 | |
| 218436_at | −3.05 | −209 | |
| 220161_s_at | −3.05 | −208 | |
| 203397_s_at | −3.05 | −207 | |
| 203228_at | −3.05 | −206 | |
| 201490_s_at | −3.05 | −205 | |
| 219015_s_at | −3.06 | −204 | |
| 202838_at | −3.06 | −203 | |
| 51200_at | −3.06 | −202 | |
| 202718_at | −3.07 | −201 | |
| 215111_s_at | −3.07 | −200 | |
| 203606_at | −3.07 | −199 | |
| 209309_at | −3.08 | −198 | |
| 203189_s_at | −3.08 | −197 | |
| 217014_s_at | −3.08 | −196 | |
| 202154_x_at | −3.09 | −195 | |
| 201016_at | −3.09 | −194 | |
| 203190_at | −3.09 | −193 | |
| 218123_at | −3.09 | −192 | |
| 220966_x_at | −3.09 | −191 | |
| 209398_at | −3.1 | −190 | |
| 212411_at | −3.1 | −189 | |
| 202096_s_at | −3.1 | −188 | |
| 209104_s_at | −3.1 | −187 | |
| 212085_at | −3.1 | −186 | |
| 208837_at | −3.1 | −185 | |
| 217812_at | −3.1 | −184 | |
| 208929_x_at | −3.1 | −183 | |
| 204360_s_at | −3.11 | −182 | |
| 208856_x_at | −3.11 | −181 | |
| 213902_at | −3.11 | −180 | |
| 208654_s_at | −3.11 | −179 | |

TABLE 10-continued

Top genes identified as up- and down-regulated in prostate stroma of relapse patients, calculated by linear regression, including all samples with prostate cancer. (negative numbers for down-regulated. −1 is best)

| Affymetrix number | T statistic | Rank | |
|---|---|---|---|
| 211936_at | −3.12 | −178 | |
| 221255_s_at | −3.12 | −177 | |
| 212347_x_at | −3.12 | −176 | |
| 209391_at | −3.13 | −175 | |
| 203136_at | −3.13 | −174 | |
| 208821_at | −3.13 | −173 | |
| 216338_s_at | −3.13 | −172 | |
| 218188_s_at | −3.13 | −171 | |
| 221844_x_at | −3.14 | −170 | |
| 201192_s_at | −3.14 | −169 | |
| 208910_s_at | −3.14 | −168 | |
| 206303_s_at | −3.14 | −167 | |
| 213062_at | −3.14 | −166 | |
| 200970_s_at | −3.15 | −165 | |
| 216449_x_at | −3.15 | −164 | |
| 208783_s_at | −3.15 | −163 | |
| 202655_at | −3.15 | −162 | |
| 218358_at | −3.16 | −161 | |
| 221827_at | −3.16 | −160 | |
| 200700_s_at | −3.17 | −159 | |
| 210312_s_at | −3.17 | −158 | |
| 213041_s_at | −3.17 | −157 | |
| 218531_at | −3.18 | −156 | |
| 213285_at | −3.18 | −155 | |
| 215071_s_at | −3.19 | −154 | |
| 202286_s_at | −3.19 | −153 | |
| 214469_at | −3.2 | −152 | |
| 220757_s_at | −3.2 | −151 | |
| 218258_at | −3.2 | −150 | |
| 220934_s_at | −3.2 | −149 | |
| 218961_s_at | −3.21 | −148 | |
| 209161_at | −3.22 | −147 | |
| 202168_at | −3.22 | −146 | |
| 208546_x_at | −3.22 | −145 | |
| 208415_x_at | −3.22 | −144 | |
| 208977_x_at | −3.22 | −143 | |
| 201825_s_at | −3.22 | −142 | |
| 218194_at | −3.22 | −141 | |
| 201358_s_at | −3.23 | −140 | |
| 210010_s_at | −3.23 | −139 | |
| 200098_s_at | −3.23 | −138 | |
| 217927_at | −3.24 | −137 | |
| 220741_s_at | −3.24 | −136 | |
| 201119_s_at | −3.24 | −135 | |
| 218552_at | −3.24 | −134 | |
| 208750_at | −3.24 | −133 | |
| 208583_x_at | −3.24 | −132 | |
| 218112_at | −3.25 | −131 | |
| 219762_s_at | −3.25 | −130 | |
| 218962_s_at | −3.25 | −129 | |
| 210719_s_at | −3.25 | −128 | |
| 219118_at | −3.25 | −127 | |
| 203133_at | −3.26 | −126 | |
| 202812_at | −3.26 | −125 | |
| 209302_at | −3.26 | −124 | |
| 202740_at | −3.26 | −123 | |
| 214531_s_at | −3.27 | −122 | |
| 205470_s_at | −3.28 | −121 | D |
| 212685_s_at | −3.28 | −120 | |
| 200654_at | −3.28 | −119 | |
| 219049_at | −3.28 | −118 | |
| 221732_at | −3.29 | −117 | |
| 203517_at | −3.29 | −116 | |
| 201096_s_at | −3.29 | −115 | |
| 213931_at | −3.29 | −114 | D |
| 208751_at | −3.3 | −113 | |
| 203647_at | −3.3 | −112 | |
| 202788_at | −3.31 | −111 | |
| 208923_at | −3.31 | −110 | |
| 218921_at | −3.33 | −109 | |
| 218580_x_at | −3.33 | −108 | |
| 209665_at | −3.34 | −107 | |
| 205347_s_at | −3.34 | −106 | |
| 200022_at | −3.34 | −105 | |
| 217979_at | −3.35 | −104 | |
| 202109_at | −3.36 | −103 | |
| 218313_s_at | −3.37 | −102 | |
| 208909_at | −3.37 | −101 | |
| 201268_at | −3.38 | −100 | |
| 213988_s_at | −3.38 | −99 | D |
| 207157_s_at | −3.38 | −98 | |
| 204331_s_at | −3.39 | −97 | |
| 209404_s_at | −3.39 | −96 | |
| 209806_at | −3.39 | −95 | |
| 204175_at | −3.4 | −94 | |
| 201359_at | −3.4 | −93 | |
| 220094_s_at | −3.41 | −92 | |
| 213315_x_at | −3.41 | −91 | |
| 218070_s_at | −3.41 | −90 | |
| 210386_s_at | −3.42 | −89 | |
| 208726_s_at | −3.43 | −88 | |
| 202941_at | −3.43 | −87 | |
| 213897_s_at | −3.45 | −86 | |
| 204862_s_at | −3.45 | −85 | |
| 200093_s_at | −3.45 | −84 | D |
| 209123_at | −3.45 | −83 | |
| 202427_s_at | −3.46 | −82 | D |
| 203582_s_at | −3.46 | −81 | |
| 204088_at | −3.46 | −80 | |
| 220495_s_at | −3.46 | −79 | |
| 210592_s_at | −3.48 | −78 | |
| 208734_x_at | −3.49 | −77 | |
| 46323_at | −3.49 | −76 | D |
| 211574_s_at | −3.49 | −75 | |
| 210667_s_at | −3.49 | −74 | |
| 217940_s_at | −3.49 | −73 | |
| 200044_at | −3.5 | −72 | |
| 201704_at | −3.5 | −71 | |
| 204034_at | −3.51 | −70 | |
| 212527_at | −3.51 | −69 | |
| 208490_x_at | −3.51 | −68 | |
| 203415_at | −3.51 | −67 | |
| 202297_s_at | −3.52 | −66 | |
| 200820_at | −3.52 | −65 | |
| 52940_at | −3.52 | −64 | |
| 201758_at | −3.53 | −63 | |
| 209420_s_at | −3.53 | −62 | |
| 201944_at | −3.53 | −61 | |
| 212739_s_at | −3.53 | −60 | |
| 201489_at | −3.53 | −59 | |
| 218387_s_at | −3.54 | −58 | |
| 222209_s_at | −3.55 | −57 | |
| 200670_at | −3.56 | −56 | |
| 203372_s_at | −3.57 | −55 | |
| 202418_at | −3.59 | −54 | |
| 36554_at | −3.59 | −53 | |
| 210434_x_at | −3.59 | −52 | |
| 202996_at | −3.6 | −51 | |
| 212961_x_at | −3.66 | −50 | |
| 218898_at | −3.66 | −49 | |
| 218388_at | −3.68 | −48 | |
| 207805_s_at | −3.68 | −47 | |
| 202120_x_at | −3.69 | −46 | |
| 217995_at | −3.7 | −45 | D |
| 208579_x_at | −3.7 | −44 | |
| 208074_s_at | −3.7 | −43 | |
| 200681_at | −3.73 | −42 | |
| 201849_at | −3.73 | −41 | D |
| 200656_at | −3.73 | −40 | D |
| 209149_s_at | −3.74 | −39 | |
| 202475_at | −3.76 | −38 | |
| 208527_x_at | −3.77 | −37 | |
| 204319_s_at | −3.78 | −36 | D |
| 205593_s_at | −3.78 | −35 | |

TABLE 10-continued

Top genes identified as up- and down-regulated in prostate stroma of relapse patients, calculated by linear regression, including all samples with prostate cancer. (negative numbers for down-regulated. −1 is best)

| Affymetrix number | T statistic | Rank | |
|---|---|---|---|
| 219188_s_at | −3.78 | −34 | |
| 203430_at | −3.78 | −33 | |
| 200075_s_at | −3.78 | −32 | D |
| 207023_x_at | −3.79 | −31 | |
| 216295_s_at | −3.81 | −30 | |
| 204392_at | −3.82 | −29 | |
| 222067_x_at | −3.82 | −28 | |
| 200048_s_at | −3.84 | −27 | D |
| 200971_s_at | −3.87 | −26 | |
| 217744_s_at | −3.89 | −25 | |
| 200065_s_at | −3.9 | −24 | |
| 211047_x_at | −3.92 | −23 | |
| 201410_at | −3.93 | −22 | |
| 201201_at | −3.95 | −21 | |
| 218280_x_at | −3.95 | −20 | |
| 214290_s_at | −3.97 | −19 | D |
| 201848_s_at | −4 | −18 | |
| 207549_x_at | −4.02 | −17 | D |
| 201264_at | −4.05 | −16 | D |
| 202929_s_at | −4.07 | −15 | D |
| 200846_s_at | −4.09 | −14 | D |
| 201953_at | −4.09 | −13 | |
| 212280_x_at | −4.09 | −12 | |
| 202041_s_at | −4.1 | −11 | |
| 218592_s_at | −4.2 | −10 | |
| 201079_at | 4.24 | −9 | D |
| 213166_x_at | −4.25 | −8 | |
| 202671_s_at | −4.28 | −7 | |
| 204903_x_at | −4.43 | −6 | |
| 203663_s_at | −4.49 | −5 | D |
| 212995_x_at | −4.67 | −4 | D |
| 217871_s_at | −4.97 | −3 | D |
| 201106_at | −5.02 | −2 | |
| 202296_s_at | −5.11 | −1 | D |

TABLE 11

43 gene classifier for relapse of prostate cancer

| Affymetrix number | |
|---|---|
| 210986_s_at | |
| 201022_s_at | |
| 200795_at | |
| 202274_at | |
| 218509_at | D |
| 201497_x_at | |
| 220587_s_at | |
| 201891_s_at | |
| 209074_s_at | D |
| 200897_s_at | |
| 202296_s_at | D |
| 202432_at | |
| 201106_at | |
| 221667_s_at | |
| 217871_s_at | D |
| 208579_x_at | |
| 200974_at | |
| 201431_s_at | |
| 221958_s_at | |
| 209288_s_at | |
| 203951_at | |
| 216231_s_at | |
| 201540_at | |
| 207430_s_at | D |
| 207480_s_at | |
| 202994_s_at | |

TABLE 11-continued 43 gene classifier for relapse of prostate cancer

| Affymetrix number | |
|---|---|
| 212995_x_at | D |
| 209763_at | |
| 217897_at | D |
| 202228_s_at | |
| 209948_at | D |
| 218418_s_at | |
| 212077_at | |
| 205011_at | |
| 209286_at | |
| 208490_x_at | |
| 209806_at | |
| 208527_x_at | |
| 202555_s_at | |
| 208676_s_at | D |
| 210987_x_at | |
| 203663_s_at | D |
| 202350_s_at | |

TABLE 12

Top 144 genes identified as down-regulated in prostate stroma cells of relapse patients, calculated by linear regression, including only samples from regions of the prostate that did not have detectable tumor cells

| Affymetrix number | T statistic | Rank | |
|---|---|---|---|
| 211047_x_at | −5.79 | 1 | |
| 201106_at | −5.18 | 2 | |
| 208074_s_at | −5.05 | 3 | |
| 202120_x_at | −4.82 | 4 | |
| 212280_x_at | −4.68 | 5 | |
| 202296_s_at | −4.45 | 6 | D |
| 211404_s_at | −4.37 | 7 | |
| 201201_at | −4.34 | 8 | |
| 208923_at | −4.26 | 9 | |
| 204903_x_at | −4.21 | 10 | |
| 210010_s_at | −4.08 | 11 | |
| 208929_x_at | −3.96 | 12 | |
| 52940_at | −3.93 | 13 | |
| 202041_s_at | −3.9 | 14 | |
| 210719_s_at | −3.89 | 15 | |
| 212995_x_at | −3.87 | 16 | D |
| 202671_s_at | −3.85 | 17 | |
| 218552_at | −3.83 | 18 | |
| 217930_s_at | −3.8 | 19 | |
| 203663_s_at | −3.79 | 20 | D |
| 200075_s_at | −3.76 | 21 | D |
| 217744_s_at | −3.73 | 22 | |
| 207023_x_at | −3.72 | 23 | |
| 201848_s_at | −3.69 | 24 | |
| 208726_s_at | −3.69 | 25 | |
| 218388_at | −3.68 | 26 | |
| 212961_x_at | −3.67 | 27 | |
| 200656_s_at | −3.66 | 28 | D |
| 217871_s_at | −3.66 | 29 | D |
| 220757_s_at | −3.63 | 30 | |
| 213624_at | −3.61 | 31 | |
| 202096_s_at | −3.6 | 32 | |
| 209113_s_at | −3.6 | 33 | |
| 221972_s_at | −3.59 | 34 | |
| 221566_s_at | −3.59 | 35 | |
| 202929_s_at | −3.59 | 36 | D |
| 208702_x_at | −3.59 | 37 | |
| 201953_at | −3.57 | 38 | |
| 201119_s_at | −3.57 | 39 | |
| 202996_at | −3.57 | 40 | |
| 201520_s_at | −3.57 | 41 | |
| 219929_s_at | −3.54 | 42 | |

TABLE 12-continued

Top 144 genes identified as down-regulated in prostate stroma cells of relapse patients, calculated by linear regression, including only samples from regions of the prostate that did not have detectable tumor cells

| Affymetrix number | T statistic | Rank | |
|---|---|---|---|
| 214875_x_at | −3.54 | 43 | |
| 209420_s_at | −3.53 | 44 | |
| 201587_s_at | −3.5 | 45 | |
| 201489_at | −3.49 | 46 | |
| 213897_s_at | −3.47 | 47 | |
| 208751_at | −3.45 | 48 | |
| 203517_at | −3.45 | 49 | |
| 204360_s_at | −3.43 | 50 | |
| 201490_s_at | −3.42 | 51 | |
| 201264_at | −3.42 | 52 | D |
| 214882_s_at | −3.41 | 53 | |
| 208669_s_at | −3.4 | 54 | |
| 213931_at | −3.39 | 55 | D |
| 219119_at | −3.37 | 56 | |
| 36554_at | −3.37 | 57 | |
| 202424_at | −3.36 | 58 | |
| 218387_s_at | −3.36 | 59 | |
| 217716_s_at | −3.35 | 60 | |
| 221567_at | −3.35 | 61 | |
| 210097_s_at | −3.33 | 62 | |
| 59625_at | −3.33 | 63 | |
| 207805_s_at | −3.33 | 64 | |
| 213166_x_at | −3.31 | 65 | |
| 212085_at | −3.3 | 66 | |
| 215952_s_at | −3.3 | 67 | |
| 218592_s_at | −3.3 | 68 | |
| 216308_x_at | −3.29 | 69 | |
| 213061_s_at | −3.29 | 70 | |
| 209472_at | −3.28 | 71 | |
| 202308_at | −3.28 | 72 | |
| 208909_at | −3.27 | 73 | |
| 208787_at | −3.27 | 74 | |
| 204238_s_at | −3.27 | 75 | |
| 207157_s_at | −3.27 | 76 | |
| 204981_at | −3.26 | 77 | |
| 209407_s_at | −3.26 | 78 | |
| 218921_at | −3.25 | 79 | |
| 208734_x_at | −3.25 | 80 | |
| 208928_at | −3.25 | 81 | |
| 40225_at | −3.24 | 82 | |
| 210386_s_at | −3.24 | 83 | |
| 220607_x_at | −3.23 | 84 | |
| 212347_x_at | −3.23 | 85 | |
| 217940_s_at | −3.23 | 86 | |
| 210667_s_at | −3.22 | 87 | |
| 200637_s_at | −3.22 | 88 | |
| 41047_at | −3.22 | 89 | |
| 201705_at | −3.21 | 90 | |
| 200022_at | −3.2 | 91 | |
| 209222_s_at | −3.2 | 92 | |
| 218070_s_at | −3.19 | 93 | |
| 212191_x_at | −3.19 | 94 | |
| 222191_s_at | −3.18 | 95 | |
| 203647_s_at | −3.18 | 96 | |
| 203571_s_at | −3.18 | 97 | |
| 200065_s_at | −3.17 | 98 | |
| 208750_s_at | −3.16 | 99 | |
| 201192_s_at | −3.16 | 100 | |
| 208024_s_at | −3.15 | 101 | |
| 204608_at | −3.15 | 102 | |
| 204034_at | −3.15 | 103 | |
| 209149_s_at | −3.14 | 104 | |
| 218150_at | −3.13 | 105 | |
| 201849_at | −3.13 | 106 | D |
| 218132_s_at | −3.13 | 107 | |
| 1729_at | −3.13 | 108 | |
| 203372_s_at | −3.11 | 109 | |
| 220597_s_at | −3.1 | 110 | |
| 209217_s_at | −3.1 | 111 | |
| 214274_s_at | −3.09 | 112 | |
| 218289_s_at | −3.09 | 113 | |
| 210130_s_at | −3.09 | 114 | |
| 209076_s_at | −3.09 | 115 | |
| 202812_at | −3.08 | 116 | |
| 202736_s_at | −3.08 | 117 | |
| 204392_at | −3.08 | 118 | |
| 203582_s_at | −3.07 | 119 | |
| 217912_at | −3.07 | 120 | |
| 201079_at | −3.07 | 121 | D |
| 201095_at | −3.07 | 122 | |
| 218652_s_at | −3.07 | 123 | |
| 208918_s_at | −3.06 | 124 | |
| 219188_s_at | −3.06 | 125 | |
| 51200_at | −3.06 | 126 | |
| 200710_at | −3.05 | 127 | |
| 213062_at | −3.05 | 128 | |
| 200846_s_at | −3.04 | 129 | D |
| 218188_s_at | −3.04 | 130 | |
| 213287_s_at | −3.04 | 131 | |
| 202737_s_at | −3.03 | 132 | |
| 212782_x_at | −3.03 | 133 | |
| 214494_s_at | −3.03 | 134 | |
| 221850_x_at | −3.03 | 135 | |
| 203430_at | −3.02 | 136 | |
| 204862_s_at | −3.02 | 137 | |
| 200654_at | −3.02 | 138 | |
| 200852_x_at | −3.02 | 139 | |
| 201704_at | −3.02 | 140 | |
| 217014_s_at | −3.01 | 141 | |
| 206469_x_at | −3 | 142 | |
| 202139_at | −3 | 143 | |
| 216862_s_at | −3 | 144 | |

TABLE 13

Top 100 genes identified as up-regulated in prostate stroma from patients that had relapsed, including only samples from regions of the prostate that did not have detectable tumor cells

| Affymetrix number | T statistic | Rank | |
|---|---|---|---|
| 204951_at | 4.73 | 1 | |
| 204795_at | 4.64 | 2 | |
| 51774_s_at | 4.54 | 3 | |
| 205456_at | 4.52 | 4 | |
| 211323_s_at | 4.51 | 5 | D |
| 201320_at | 4.28 | 6 | |
| 204436_at | 4.05 | 7 | |
| 205988_at | 3.98 | 8 | |
| 212076_at | 3.97 | 9 | |
| 218525_s_at | 3.94 | 10 | |
| 209671_x_at | 3.89 | 11 | |
| 211991_s_at | 3.73 | 12 | |
| 205405_at | 3.69 | 13 | |
| 58900_at | 3.66 | 14 | |
| 210038_at | 3.65 | 15 | |
| 211599_x_at | 3.59 | 16 | |
| 207834_at | 3.55 | 17 | |
| 204901_at | 3.53 | 18 | |
| 209616_s_at | 3.49 | 19 | D |
| 217187_at | 3.48 | 20 | |
| 219812_at | 3.47 | 21 | |
| 211123_at | 3.44 | 22 | |
| 209582_s_at | 3.42 | 23 | D |
| 211902_x_at | 3.42 | 24 | |
| 221486_at | 3.41 | 25 | |

TABLE 13-continued

Top 100 genes identified as up-regulated in prostate stroma from patients that had relapsed, including only samples from regions of the prostate that did not have detectable tumor cells

| Affymetrix number | T statistic | Rank | |
|---|---|---|---|
| 219035_s_at | 3.39 | 26 | |
| 210972_x_at | 3.38 | 27 | |
| 201080_at | 3.38 | 28 | |
| 219877_at | 3.37 | 29 | |
| 208598_s_at | 3.35 | 30 | |
| 209670_at | 3.35 | 31 | |
| 218581_at | 3.34 | 32 | |
| 210072_at | 3.33 | 33 | D |
| 215826_x_at | 3.33 | 34 | |
| 213193_x_at | 3.3 | 35 | |
| 202501_at | 3.3 | 36 | |
| 207648_at | 3.29 | 37 | |
| 204562_at | 3.29 | 38 | |
| 207691_x_at | 3.24 | 39 | |
| 64064_at | 3.23 | 40 | |
| 211203_at | 3.23 | 41 | |
| 214760_at | 3.22 | 42 | |
| 204341_at | 3.21 | 43 | D |
| 206053_at | 3.21 | 44 | |
| 202401_s_at | 3.21 | 45 | |
| 204852_s_at | 3.21 | 46 | |
| 200610_s_at | 3.21 | 47 | |
| 202964_s_at | 3.2 | 48 | |
| 205011_at | 3.19 | 49 | |
| 202809_s_at | 3.18 | 50 | |
| 38521_at | 3.18 | 51 | |
| 209062_x_at | 3.16 | 52 | |
| 211504_x_at | 3.16 | 53 | |
| 208306_x_at | 3.15 | 54 | |
| 217362_x_at | 3.15 | 55 | |
| 212151_at | 3.15 | 56 | |
| 212100_s_at | 3.14 | 57 | |
| 214738_s_at | 3.14 | 58 | |
| 202578_s_at | 3.14 | 59 | |
| 204882_at | 3.14 | 60 | |
| 204563_at | 3.13 | 61 | D |
| 213386_at | 3.13 | 62 | |
| 206105_at | 3.13 | 63 | |
| 211796_s_at | 3.13 | 64 | |
| 212713_at | 3.13 | 65 | D |
| 217418_x_at | 3.12 | 66 | |
| 204116_at | 3.11 | 67 | |
| 211710_x_at | 3.1 | 68 | |
| 204640_s_at | 3.1 | 69 | |
| 213370_s_at | 3.09 | 70 | |
| 214694_at | 3.08 | 71 | |
| 210444_at | 3.08 | 72 | |
| 218338_at | 3.08 | 73 | |
| 206767_at | 3.08 | 74 | |
| 209473_at | 3.08 | 75 | |
| 203157_s_at | 3.07 | 76 | |
| 200064_at | 3.07 | 77 | |
| 212972_x_at | 3.07 | 78 | |
| 215592_at | 3.06 | 79 | |
| 210915_x_at | 3.06 | 80 | |
| 205821_at | 3.05 | 81 | |
| 213831_at | 3.04 | 82 | |
| 214928_at | 3.04 | 83 | |
| 209057_x_at | 3.03 | 84 | D |
| 208459_s_at | 3.03 | 85 | |
| 213958_at | 3.02 | 86 | |
| 207547_s_at | 3 | 87 | |
| 215946_x_at | 2.99 | 88 | |
| 210356_x_at | 2.99 | 89 | |
| 214450_at | 2.99 | 90 | |
| 204229_at | 2.98 | 91 | |
| 200621_at | 2.98 | 92 | D |
| 208227_x_at | 2.97 | 93 | |
| 215762_at | 2.96 | 94 | |
| 38149_at | 2.96 | 95 | |
| 217925_s_at | 2.95 | 96 | |
| 215379_x_at | 2.95 | 97 | |
| 71933_at | 2.94 | 98 | |
| 211269_s_at | 2.93 | 99 | |
| 206180_x_at | 2.91 | 100 | |

TABLE 14

List of 35 (nonunique) genes associated with differential expression in aggressive prostate cancer found among the statistically differentially expressed genes of early relapse prostate cancer (cf. Tables 9 and 10).

| Set Name | 148_rs_btsg_regcoeff_tstats_nam_Name |
|---|---|
| 211323_s_at | inositol 1,4,5-triphosphate receptor, type 1 |
| 208579_x_at | histone 1, H2bk |
| 208490_x_at | histone 1, H2bf |
| 209806_at | histone 1, H2bk |
| 209844_at | homeo box B13 |
| 222067_x_at | histone 1, H2bd |
| 201893_x_at | decorin |
| 202401_s_at | serum response factor (c-fos serum response element-binding transcription factor) |
| 202525_at | protease, serine, 8 (prostasin) |
| 204934_s_at | hepsin (transmembrane protease, serine 1) |
| 207547_s_at | TU3A protein |
| 208527_x_at | histone 1, H2be |
| 218186_at | RAB25, member RAS oncogene family |
| 200621_at | cysteine and glycine-rich protein 1 |
| 208789_at | polymerase I and transcript release factor |
| 212713_at | microfibrillar-associated protein 4 |
| 205011_at | loss of heterozygosity, 11, chromosomal region 2, gene A |
| 208546_x_at | histone 1, H2bh |
| 209473_at | ectonucleoside triphosphate diphosphohydrolase 1 |
| 209696_at | fructose-1,6-bisphosphatase 1 |
| 221958_s_at | hypothetical protein FLJ23091 |
| 200953_s_at | cyclin D2 |
| 200852_x_at | guanine nucleotide binding protein (G protein), beta polypeptide 2 |
| 202074_s_at | optineurin |
| 206491_s_at | N-ethylmaleimide-sensitive factor attachment protein, alpha |
| 208751_at | N-ethylmaleimide-sensitive factor attachment protein, alpha |
| 204754_at | hepatic leukemia factor |
| 200795_at | SPARC-like 1 (mast9, hevin) |
| 200974_at | actin, alpha 2, smooth muscle, aorta |
| 202041_s_at | fibroblast growth factor (acidic) intracellular binding protein |
| 202501_at | microtubule-associated protein, RP/EB family, member 2 |
| 202545_at | protein kinase C, delta |
| 209297_at | intersectin 1 (SH3 domain protein) |
| 202758_s_at | regulatory factor X-associated ankyrin-containing protein |

TABLE 17

| probeID U133 | probeID U95A |
|---|---|
| AFFX-HUMGAPDH/M33197_M_at | 35905_s_at |
| AFFX-HUMGAPDH/M33197_5_at | 35905_s_at |
| AFFX-HUMGAPDH/M33197_3_at | 35905_s_at |
| AFFX-HSAC07/X00351_M_at | 32318_s_at |
| AFFX-HSAC07/X00351_M_at | AFFX-HSAC07/X00351_3_at |
| AFFX-HSAC07/X00351_M_at | AFFX-HSAC07/X00351_3_st |
| AFFX-HSAC07/X00351_M_at | AFFX-HSAC07/X00351_5_at |
| AFFX-HSAC07/X00351_M_at | AFFX-HSAC07/X00351_5_st |

TABLE 17-continued

| probeID U133 | probeID U95A |
|---|---|
| AFFX-HSAC07/X00351_M_at | AFFX-HSAC07/X00351_M_at |
| AFFX-HSAC07/X00351_5_at | 32318_s_at |
| AFFX-HSAC07/X00351_5_at | AFFX-HSAC07/X00351_3_at |
| AFFX-HSAC07/X00351_5_at | AFFX-HSAC07/X00351_3_st |
| AFFX-HSAC07/X00351_5_at | AFFX-HSAC07/X00351_5_at |
| AFFX-HSAC07/X00351_5_at | AFFX-HSAC07/X00351_5_st |
| AFFX-HSAC07/X00351_5_at | AFFX-HSAC07/X00351_M_at |
| AFFX-HSAC07/X00351_3_at | 32318_s_at |
| AFFX-HSAC07/X00351_3_at | AFFX-HSAC07/X00351_3_at |
| AFFX-HSAC07/X00351_3_at | AFFX-HSAC07/X00351_3_st |
| AFFX-HSAC07/X00351_3_at | AFFX-HSAC07/X00351_5_at |
| AFFX-HSAC07/X00351_3_at | AFFX-HSAC07/X00351_5_st |
| AFFX-HSAC07/X00351_3_at | AFFX-HSAC07/X00351_M_at |
| 39817_s_at | 39817_s_at |
| 39817_s_at | 39818_at |
| 38671_at | 38671_at |
| 37996_s_at | 37996_s_at |
| 37950_at | 37950_at |
| 37408_at | 37408_at |
| 37384_at | 37384_at |
| 37117_at | 37117_at |
| 37022_at | 37022_at |
| 37005_at | 37005_at |
| 35846_at | 35846_at |
| 33850_at | 242_at |
| 33850_at | 243_g_at |
| 33850_at | 32226_at |
| 33767_at | 33767_at |
| 33323_r_at | 33322_i_at |
| 33323_r_at | 33323_r_at |
| 33322_i_at | 33322_i_at |
| 33322_i_at | 33323_r_at |
| 32094_at | 32094_at |
| 243_g_at | 242_at |
| 243_g_at | 243_g_at |
| 243_g_at | 32226_at |
| 222221_x_at | 40098_at |
| 222067_x_at | 38576_at |
| 222043_at | 36780_at |
| 221922_at | 33185_at |
| 221881_s_at | 33891_at |
| 221872_at | 1042_at |
| 221730_at | 38420_at |
| 221729_at | 38420_at |
| 221586_s_at | 1044_s_at |
| 221586_s_at | 1639_s_at |
| 221584_s_at | 40737_at |
| 221564_at | 39348_at |
| 221475_s_at | 32432_f_at |
| 219514_at | 37573_at |
| 219140_s_at | 32552_at |
| 218924_s_at | 37855_at |
| 218831_s_at | 31431_at |
| 218831_s_at | 31432_g_at |
| 218820_at | 41837_at |
| 218215_s_at | 518_at |
| 217871_s_at | 895_at |
| 217826_s_at | 39039_s_at |
| 217826_s_at | 39040_at |
| 217764_s_at | 33371_s_at |
| 217764_s_at | 33372_at |
| 217763_s_at | 33371_s_at |
| 217763_s_at | 33372_at |
| 217762_s_at | 33371_s_at |
| 217762_s_at | 33372_at |
| 217741_s_at | 41542_at |
| 217691_x_at | 33143_s_at |
| 217487_x_at | 1739_at |
| 217487_x_at | 1740_g_at |
| 217437_s_at | 40841_at |
| 217398_x_at | 35905_s_at |
| 217066_s_at | 37996_s_at |
| 217014_s_at | 35834_at |
| 216944_s_at | 32778_at |
| 216944_s_at | 32779_s_at |
| 216944_s_at | 755_at |
| 216905_s_at | 35309_at |
| 216899_s_at | 36091_at |
| 216887_s_at | 34870_at |
| 216866_s_at | 34388_at |
| 216840_s_at | 36917_at |
| 216733_s_at | 36595_s_at |
| 216733_s_at | 36596_r_at |
| 216689_x_at | 39700_at |
| 216689_x_at | 552_at |
| 216689_x_at | 553_g_at |
| 216623_x_at | 37426_at |
| 216602_s_at | 34291_at |
| 216594_x_at | 32805_at |
| 216483_s_at | 38969_at |
| 216474_x_at | 32905_s_at |
| 216442_x_at | 311_s_at |
| 216442_x_at | 31719_at |
| 216442_x_at | 31720_s_at |
| 216438_s_at | 33421_s_at |
| 216397_s_at | 35615_at |
| 216331_at | 36892_at |
| 216251_s_at | 37648_at |
| 216236_s_at | 36979_at |
| 216235_s_at | 1507_s_at |
| 216230_x_at | 32574_at |
| 216230_x_at | 37371_at |
| 216215_s_at | 40260_g_at |
| 216205_s_at | 34369_at |
| 216111_x_at | 41258_at |
| 216100_s_at | 40832_s_at |
| 216100_s_at | 40833_r_at |
| 216074_x_at | 34213_at |
| 216033_s_at | 2039_s_at |
| 216033_s_at | 40480_s_at |
| 215990_s_at | 40091_at |
| 215779_s_at | 32819_at |
| 215711_s_at | 36909_at |
| 215707_s_at | 36159_s_at |
| 215706_x_at | 36958_at |
| 215606_s_at | 37869_at |
| 215537_x_at | 36131_at |
| 215537_x_at | 38621_at |
| 215493_x_at | 32673_at |
| 215485_s_at | 32640_at |
| 215471_s_at | 39732_at |
| 215464_s_at | 39416_at |
| 215438_x_at | 33932_at |
| 215382_x_at | 32905_s_at |
| 215333_x_at | 39054_at |
| 215300_s_at | 37874_at |
| 215222_x_at | 38704_at |
| 215193_x_at | 41723_s_at |
| 215108_x_at | 37426_at |
| 215051_x_at | 33641_g_at |
| 215016_x_at | 40304_at |
| 215000_s_at | 38651_at |
| 214909_s_at | 36131_at |
| 214909_s_at | 38621_at |
| 214894_x_at | 38704_at |
| 214889_at | 34423_at |
| 214875_x_at | 33944_at |
| 214789_x_at | 32038_s_at |
| 214774_x_at | 37426_at |
| 214771_x_at | 38730_at |
| 214761_at | 34950_at |
| 214752_x_at | 32749_s_at |
| 214752_x_at | 32750_r_at |
| 214726_x_at | 32145_at |
| 214643_x_at | 459_s_at |
| 214598_at | 33611_g_at |
| 214582_at | 35872_at |
| 214582_at | 746_at |
| 214577_at | 41373_s_at |
| 214543_x_at | 39759_at |
| 214543_x_at | 39760_at |
| 214508_x_at | 32065_at |
| 214508_x_at | 32066_g_at |
| 214508_x_at | 32067_at |
| 214505_s_at | 32542_at |
| 214501_s_at | 36576_at |

TABLE 17-continued

| probeID U133 | probeID U95A |
|---|---|
| 214500_at | 36576_at |
| 214463_x_at | 34027_f_at |
| 214455_at | 32980_f_at |
| 214449_s_at | 1818_at |
| 214449_s_at | 40555_at |
| 214439_x_at | 459_s_at |
| 214308_s_at | 31844_at |
| 214307_at | 31844_at |
| 214271_x_at | 33668_at |
| 214266_s_at | 39530_at |
| 214265_at | 41005_at |
| 214212_x_at | 36577_at |
| 214170_x_at | 32546_at |
| 214167_s_at | 31538_at |
| 214117_s_at | 37274_at |
| 214077_x_at | 37486_f_at |
| 214040_s_at | 32612_at |
| 214039_s_at | 41188_at |
| 214027_x_at | 40776_at |
| 213994_s_at | 35277_at |
| 213993_at | 35277_at |
| 213992_at | 39939_at |
| 213982_s_at | 34445_at |
| 213982_s_at | 34446_at |
| 213974_at | 38856_at |
| 213947_s_at | 41812_s_at |
| 213901_x_at | 40260_g_at |
| 213892_s_at | 34310_at |
| 213867_x_at | 32318_s_at |
| 213867_x_at | AFFX-HSAC07/X00351_3_at |
| 213867_x_at | AFFX-HSAC07/X00351_3_st |
| 213867_x_at | AFFX-HSAC07/X00351_5_at |
| 213867_x_at | AFFX-HSAC07/X00351_5_st |
| 213867_x_at | AFFX-HSAC07/X00351_M_at |
| 213804_at | 33290_at |
| 213800_at | 32250_at |
| 213798_s_at | 935_at |
| 213791_at | 38291_at |
| 213787_s_at | 32536_at |
| 213746_s_at | 32749_s_at |
| 213746_s_at | 32750_r_at |
| 213702_x_at | 36938_at |
| 213702_x_at | 461_at |
| 213688_at | 41143_at |
| 213688_at | 41144_g_at |
| 213675_at | 39750_at |
| 213620_s_at | 38454_g_at |
| 213600_at | 37831_at |
| 213572_s_at | 33305_at |
| 213541_s_at | 36383_at |
| 213541_s_at | 914_g_at |
| 213524_s_at | 38326_at |
| 213519_s_at | 36917_at |
| 213506_at | 36345_g_at |
| 213506_at | 38247_at |
| 213492_at | 37605_at |
| 213492_at | 598_at |
| 213485_s_at | 36732_at |
| 213476_x_at | 471_f_at |
| 213455_at | 38643_at |
| 213453_x_at | 35905_s_at |
| 213446_s_at | 1825_at |
| 213428_s_at | 38722_at |
| 213422_s_at | 35219_at |
| 213400_s_at | 32554_s_at |
| 213400_s_at | 32555_at |
| 213395_at | 36897_at |
| 213371_at | 34870_at |
| 213338_at | 35692_at |
| 213325_at | 34202_at |
| 213307_at | 37806_at |
| 213293_s_at | 36825_at |
| 213275_x_at | 32372_at |
| 213189_at | 34662_at |
| 213176_s_at | 33137_at |
| 213154_s_at | 40879_at |
| 213152_s_at | 32038_s_at |
| 213151_s_at | 32175_at |
| 213138_at | 38278_at |
| 213134_x_at | 37218_at |
| 213107_at | 32680_at |
| 213102_at | 35271_at |
| 213071_at | 38059_g_at |
| 213068_at | 38059_g_at |
| 213041_s_at | 37992_s_at |
| 213041_s_at | 37993_at |
| 213005_s_at | 37225_at |
| 213004_at | 37573_at |
| 213001_at | 37573_at |
| 212998_x_at | 36773_f_at |
| 212977_at | 34288_at |
| 212937_s_at | 38722_at |
| 212914_at | 39788_at |
| 212886_at | 34183_at |
| 212878_s_at | 39057_at |
| 212865_s_at | 34388_at |
| 212845_at | 40855_at |
| 212843_at | 1566_at |
| 212843_at | 41289_at |
| 212838_at | 34712_at |
| 212826_s_at | 40435_at |
| 212826_s_at | 40436_g_at |
| 212817_at | 38632_at |
| 212793_at | 41098_at |
| 212792_at | 39021_at |
| 212765_at | 34688_at |
| 212764_at | 33440_at |
| 212758_s_at | 33440_at |
| 212757_s_at | 32104_i_at |
| 212757_s_at | 32105_f_at |
| 212747_at | 40971_at |
| 212744_at | 33175_at |
| 212730_at | 39544_at |
| 212724_at | 35803_at |
| 212713_at | 39066_at |
| 212694_s_at | 36561_at |
| 212670_at | 31621_s_at |
| 212670_at | 39098_at |
| 212669_at | 32104_i_at |
| 212669_at | 32105_f_at |
| 212667_at | 671_at |
| 212658_at | 37542_at |
| 212652_s_at | 40605_at |
| 212651_at | 39771_at |
| 212647_at | 1879_at |
| 212647_at | 38338_at |
| 212646_at | 32593_at |
| 212624_s_at | 40512_at |
| 212610_at | 38443_at |
| 212609_s_at | 40781_at |
| 212590_at | 32827_at |
| 212581_x_at | 35905_s_at |
| 212573_at | 40455_at |
| 212572_at | 32182_at |
| 212567_s_at | 242_at |
| 212567_s_at | 243_g_at |
| 212567_s_at | 32226_at |
| 212566_at | 242_at |
| 212566_at | 243_g_at |
| 212566_at | 32226_at |
| 212565_at | 32182_at |
| 212563_at | 35615_at |
| 212561_at | 33924_at |
| 212554_at | 33404_at |
| 212554_at | 33405_at |
| 212554_at | 693_g_at |
| 212551_at | 33404_at |
| 212551_at | 33405_at |
| 212551_at | 693_g_at |
| 212535_at | 41747_s_at |
| 212526_at | 39852_at |
| 212510_at | 38394_at |
| 212504_at | 33407_at |
| 212504_at | 33408_at |
| 212503_s_at | 33407_at |
| 212503_s_at | 33408_at |

TABLE 17-continued

| probeID U133 | probeID U95A |
| --- | --- |
| 212494_at | 35358_at |
| 212470_at | 39419_at |
| 212457_at | 34669_at |
| 212449_s_at | 39396_at |
| 212445_s_at | 39356_at |
| 212430_at | 38661_at |
| 212409_s_at | 40832_s_at |
| 212409_s_at | 40833_r_at |
| 212408_at | 40832_s_at |
| 212408_at | 40833_r_at |
| 212358_at | 36095_at |
| 212354_at | 35832_at |
| 212344_at | 35832_at |
| 212330_at | 37758_s_at |
| 212325_at | 32812_at |
| 212316_at | 41812_s_at |
| 212314_at | 41585_at |
| 212280_x_at | 37041_at |
| 212276_at | 38098_at |
| 212274_at | 38098_at |
| 212272_at | 38098_at |
| 212254_s_at | 40304_at |
| 212253_x_at | 40304_at |
| 212252_at | 38716_at |
| 212240_s_at | 1269_at |
| 212236_x_at | 34301_r_at |
| 212235_at | 38671_at |
| 212230_at | 33862_at |
| 212227_x_at | 33850_at |
| 212203_x_at | 41745_at |
| 212197_x_at | 38730_at |
| 212169_at | 38761_s_at |
| 212157_at | 39757_at |
| 212154_at | 39757_at |
| 212130_x_at | 33850_at |
| 212127_at | 32151_at |
| 212120_at | 1818_at |
| 212120_at | 40555_at |
| 212119_at | 1818_at |
| 212119_at | 40555_at |
| 212118_at | 40176_at |
| 212117_at | 1818_at |
| 212117_at | 40555_at |
| 212116_at | 40176_at |
| 212104_s_at | 40260_g_at |
| 212097_at | 36119_at |
| 212091_s_at | 38722_at |
| 212088_at | 36602_at |
| 212085_at | 40435_at |
| 212085_at | 40436_g_at |
| 212082_s_at | 33994_g_at |
| 212071_s_at | 39556_at |
| 212067_s_at | 39409_at |
| 212041_at | 38686_at |
| 212008_at | 37336_at |
| 211991_s_at | 38833_at |
| 211990_at | 38833_at |
| 211981_at | 39333_at |
| 211980_at | 39333_at |
| 211978_x_at | 33667_at |
| 211966_at | 36659_at |
| 211964_at | 36659_at |
| 211954_s_at | 39028_at |
| 211949_s_at | 36597_at |
| 211945_s_at | 32808_at |
| 211892_s_at | 36533_at |
| 211871_x_at | 38176_at |
| 211864_s_at | 34678_at |
| 211778_at | 36761_at |
| 211765_x_at | 33667_at |
| 211762_s_at | 40407_at |
| 211749_s_at | 35783_at |
| 211719_x_at | 311_s_at |
| 211719_x_at | 31719_at |
| 211719_x_at | 31720_s_at |
| 211678_s_at | 38670_at |
| 211678_s_at | 41698_at |
| 211658_at | 39729_at |
| 211654_x_at | 36773_f_at |
| 211651_s_at | 581_at |
| 211596_s_at | 34800_at |
| 211576_s_at | 33135_at |
| 211574_s_at | 38441_s_at |
| 211573_x_at | 231_at |
| 211573_x_at | 38404_at |
| 211562_s_at | 37765_at |
| 211559_s_at | 1913_at |
| 211559_s_at | 37723_at |
| 211558_s_at | 37722_s_at |
| 211538_s_at | 36925_at |
| 211538_s_at | 645_at |
| 211537_x_at | 36905_at |
| 211536_x_at | 36905_at |
| 211535_s_at | 2056_at |
| 211535_s_at | 2057_g_at |
| 211535_s_at | 424_s_at |
| 211473_s_at | 39939_at |
| 211423_s_at | 33421_s_at |
| 211404_s_at | 33944_at |
| 211378_x_at | 33667_at |
| 211323_s_at | 32778_at |
| 211323_s_at | 32779_s_at |
| 211323_s_at | 755_at |
| 211296_x_at | 1366_i_at |
| 211296_x_at | 32335_r_at |
| 211256_x_at | 32673_at |
| 211203_s_at | 31809_at |
| 211203_s_at | 31810_g_at |
| 211160_x_at | 39329_at |
| 211160_x_at | 39330_s_at |
| 211144_x_at | 41468_at |
| 211126_s_at | 41401_at |
| 211071_s_at | 36941_at |
| 211070_x_at | 37692_at |
| 211043_s_at | 32522_f_at |
| 211031_s_at | 41396_at |
| 211026_s_at | 35792_at |
| 211003_x_at | 231_at |
| 211003_x_at | 38404_at |
| 210990_s_at | 37671_at |
| 210986_s_at | 36790_at |
| 210986_s_at | 36791_g_at |
| 210986_s_at | 36792_at |
| 210982_s_at | 37039_at |
| 210976_s_at | 36196_at |
| 210973_s_at | 2056_at |
| 210973_s_at | 2057_g_at |
| 210973_s_at | 424_s_at |
| 210935_s_at | 38736_at |
| 210907_s_at | 35218_at |
| 210840_s_at | 1825_at |
| 210829_s_at | 32668_at |
| 210794_s_at | 39026_r_at |
| 210787_s_at | 38716_at |
| 210764_s_at | 38772_at |
| 210762_s_at | 37951_at |
| 210738_s_at | 35285_at |
| 210738_s_at | 35871_s_at |
| 210736_x_at | 36467_g_at |
| 210736_x_at | 36469_at |
| 210736_x_at | 36470_s_at |
| 210702_s_at | 36533_at |
| 210648_x_at | 39360_at |
| 210628_x_at | 33137_at |
| 210627_s_at | 38464_at |
| 210592_s_at | 1173_g_at |
| 210592_s_at | 34304_s_at |
| 210588_x_at | 40836_s_at |
| 210582_s_at | 38618_at |
| 210570_x_at | 1238_at |
| 210570_x_at | 38431_at |
| 210547_x_at | 32634_s_at |
| 210544_s_at | 40409_at |
| 210541_s_at | 40176_at |
| 210517_s_at | 37680_at |
| 210495_x_at | 311_s_at |

TABLE 17-continued

| probeID U133 | probeID U95A |
|---|---|
| 210495_x_at | 31719_at |
| 210495_x_at | 31720_s_at |
| 210471_s_at | 32709_at |
| 210470_x_at | 38527_at |
| 210338_s_at | 1180_g_at |
| 210337_s_at | 40881_at |
| 210317_s_at | 1011_s_at |
| 210299_s_at | 32542_at |
| 210298_x_at | 32542_at |
| 210243_s_at | 39445_at |
| 210237_at | 35899_at |
| 210202_s_at | 459_s_at |
| 210201_x_at | 459_s_at |
| 210186_s_at | 151_s_at |
| 210156_s_at | 37737_at |
| 210139_s_at | 38653_at |
| 210110_x_at | 40836_s_at |
| 210105_s_at | 2039_s_at |
| 210105_s_at | 40480_s_at |
| 210101_x_at | 39691_at |
| 210089_s_at | 37671_at |
| 210084_x_at | 32905_s_at |
| 210079_x_at | 32709_at |
| 210036_s_at | 38225_at |
| 210036_s_at | 38858_at |
| 210027_s_at | 2025_s_at |
| 210026_s_at | 41817_g_at |
| 210026_s_at | 41818_at |
| 210024_s_at | 34850_at |
| 209967_s_at | 32065_at |
| 209967_s_at | 32066_g_at |
| 209967_s_at | 32067_at |
| 209948_at | 38298_at |
| 209897_s_at | 39634_at |
| 209896_s_at | 38443_at |
| 209895_at | 38443_at |
| 209872_s_at | 41359_at |
| 209868_s_at | 31671_at |
| 209868_s_at | 31672_g_at |
| 209868_s_at | 333_s_at |
| 209868_s_at | 33867_s_at |
| 209863_s_at | 31791_at |
| 209834_at | 32094_at |
| 209823_x_at | 36773_f_at |
| 209818_s_at | 32970_f_at |
| 209786_at | 35737_at |
| 209786_at | 35738_at |
| 209772_s_at | 266_s_at |
| 209747_at | 1767_s_at |
| 209708_at | 36834_at |
| 209702_at | 37242_at |
| 209696_at | 36495_at |
| 209695_at | 36008_at |
| 209687_at | 32666_at |
| 209687_at | 33834_at |
| 209685_s_at | 1217_g_at |
| 209685_s_at | 1336_s_at |
| 209685_s_at | 160029_at |
| 209665_at | 39752_at |
| 209663_s_at | 36892_at |
| 209656_s_at | 37958_at |
| 209655_s_at | 37958_at |
| 209651_at | 35146_at |
| 209646_x_at | 38503_at |
| 209645_s_at | 38503_at |
| 209625_at | 40629_at |
| 209624_s_at | 36432_at |
| 209623_at | 36432_at |
| 209621_s_at | 39690_at |
| 209608_s_at | 34790_at |
| 209583_s_at | 37716_at |
| 209582_s_at | 37716_at |
| 209576_at | 33809_at |
| 209568_s_at | 37539_at |
| 209563_x_at | 41143_at |
| 209563_x_at | 41144_g_at |
| 209550_at | 36073_at |
| 209539_at | 37543_at |
| 209516_at | 36462_at |
| 209505_at | 1147_at |
| 209496_at | 34407_at |
| 209488_s_at | 1276_g_at |
| 209488_s_at | 34162_at |
| 209488_s_at | 34163_g_at |
| 209488_s_at | 38047_at |
| 209488_s_at | 38049_g_at |
| 209487_at | 1276_g_at |
| 209487_at | 34162_at |
| 209487_at | 34163_g_at |
| 209487_at | 38047_at |
| 209487_at | 38049_g_at |
| 209482_at | 32213_at |
| 209470_s_at | 36939_at |
| 209469_at | 36939_at |
| 209440_at | 36489_at |
| 209437_s_at | 35277_at |
| 209436_at | 35277_at |
| 209433_s_at | 34341_at |
| 209427_at | 31830_s_at |
| 209427_at | 31831_at |
| 209426_s_at | 41706_at |
| 209425_at | 41706_at |
| 209424_s_at | 41706_at |
| 209406_at | 35291_at |
| 209402_s_at | 38625_g_at |
| 209402_s_at | 39521_at |
| 209401_s_at | 38625_g_at |
| 209401_s_at | 39521_at |
| 209398_at | 37018_at |
| 209391_at | 38726_at |
| 209389_x_at | 37692_at |
| 209379_s_at | 37617_at |
| 209368_at | 41473_at |
| 209367_at | 38259_at |
| 209366_x_at | 38458_at |
| 209366_x_at | 38459_g_at |
| 209363_s_at | 34356_at |
| 209363_s_at | 34357_g_at |
| 209360_s_at | 1882_g_at |
| 209360_s_at | 2026_at |
| 209356_x_at | 35347_at |
| 209355_s_at | 33862_at |
| 209340_at | 41242_at |
| 209337_at | 39243_s_at |
| 209323_at | 41141_at |
| 209318_x_at | 36943_r_at |
| 209312_x_at | 41723_s_at |
| 209309_at | 35834_at |
| 209302_at | 35631_at |
| 209292_at | 41536_at |
| 209291_at | 41536_at |
| 209288_s_at | 33362_at |
| 209287_s_at | 33362_at |
| 209265_s_at | 32245_at |
| 209265_s_at | 32246_g_at |
| 209242_at | 39701_at |
| 209210_s_at | 36577_at |
| 209209_s_at | 36577_at |
| 209203_s_at | 40879_at |
| 209200_at | 37710_at |
| 209199_s_at | 37710_at |
| 209198_s_at | 36144_at |
| 209197_at | 36144_at |
| 209194_at | 38410_at |
| 209170_s_at | 37251_s_at |
| 209167_at | 37251_s_at |
| 209154_at | 39416_at |
| 209147_s_at | 34797_at |
| 209142_s_at | 1423_at |
| 209129_at | 39341_at |
| 209118_s_at | 40567_at |
| 209114_at | 34775_at |
| 209113_s_at | 41526_at |
| 209104_s_at | 41322_s_at |
| 209101_at | 36638_at |
| 209091_s_at | 39691_at |

TABLE 17-continued

| probeID U133 | probeID U95A |
|---|---|
| 209090_s_at | 39691_at |
| 209074_s_at | 38044_at |
| 209047_at | 36156_at |
| 209039_x_at | 40098_at |
| 209009_at | 38375_at |
| 208985_s_at | 40616_at |
| 208980_s_at | 1366_i_at |
| 208980_s_at | 32335_r_at |
| 208978_at | 35828_at |
| 208966_x_at | 1456_s_at |
| 208964_s_at | 39372_at |
| 208964_s_at | 39373_at |
| 208964_s_at | 41719_i_at |
| 208964_s_at | 41720_r_at |
| 208962_s_at | 39372_at |
| 208962_s_at | 39373_at |
| 208962_s_at | 41719_i_at |
| 208962_s_at | 41720_r_at |
| 208944_at | 1814_at |
| 208944_at | 1815_g_at |
| 208941_s_at | 39387_at |
| 208910_s_at | 37668_at |
| 208905_at | 35818_at |
| 208904_s_at | 39798_at |
| 208899_x_at | 33854_at |
| 208894_at | 37039_at |
| 208881_x_at | 36985_at |
| 208868_s_at | 35785_at |
| 208853_s_at | 40125_at |
| 208852_s_at | 40125_at |
| 208848_at | 37707_i_at |
| 208848_at | 37708_r_at |
| 208843_s_at | 35806_at |
| 208842_s_at | 35806_at |
| 208837_at | 41163_at |
| 208801_at | 33837_at |
| 208800_at | 33837_at |
| 208792_s_at | 36780_at |
| 208791_at | 36780_at |
| 208787_at | 37726_at |
| 208786_s_at | 39370_at |
| 208781_x_at | 39360_at |
| 208778_s_at | 34791_at |
| 208770_s_at | 35263_at |
| 208767_s_at | 41188_at |
| 208763_s_at | 36629_at |
| 208763_s_at | 36630_at |
| 208756_s_at | 1644_at |
| 208756_at | 32230_at |
| 208747_s_at | 40496_at |
| 208737_at | 38814_at |
| 208702_x_at | 33944_at |
| 208700_s_at | 38789_at |
| 208699_x_at | 38789_at |
| 208698_s_at | 38527_at |
| 208687_x_at | 1180_g_at |
| 208682_s_at | 34859_at |
| 208679_s_at | 1718_at |
| 208675_s_at | 38791_at |
| 208650_s_at | 266_s_at |
| 208637_x_at | 39329_at |
| 208637_x_at | 39330_s_at |
| 208636_at | 39329_at |
| 208636_at | 39330_s_at |
| 208633_s_at | 38704_at |
| 208632_at | 34883_at |
| 208628_s_at | 36140_at |
| 208627_s_at | 36140_at |
| 208591_s_at | 35872_at |
| 208591_s_at | 746_at |
| 208527_x_at | 31523_f_at |
| 208523_x_at | 31524_f_at |
| 208490_x_at | 31522_f_at |
| 208456_s_at | 32827_at |
| 208454_s_at | 32765_f_at |
| 208447_s_at | 36489_at |
| 208430_s_at | 36467_g_at |
| 208430_s_at | 36469_at |
| 208430_s_at | 36470_s_at |
| 208370_s_at | 32168_s_at |
| 208308_s_at | 39122_at |
| 208306_x_at | 32035_at |
| 208264_s_at | 40616_at |
| 208146_s_at | 38323_at |
| 208131_s_at | 36533_at |
| 208112_x_at | 40098_at |
| 208029_s_at | 41188_at |
| 207984_s_at | 34656_at |
| 207977_s_at | 38059_g_at |
| 207961_x_at | 32582_at |
| 207961_x_at | 37407_s_at |
| 207961_x_at | 767_at |
| 207961_x_at | 773_at |
| 207961_x_at | 774_g_at |
| 207957_s_at | 1217_g_at |
| 207957_s_at | 1336_s_at |
| 207957_s_at | 160029_at |
| 207949_s_at | 32634_s_at |
| 207936_x_at | 31941_s_at |
| 207876_s_at | 35330_at |
| 207843_x_at | 38458_at |
| 207843_x_at | 38459_g_at |
| 207842_s_at | 38437_at |
| 207836_s_at | 1276_g_at |
| 207836_s_at | 34162_at |
| 207836_s_at | 34163_g_at |
| 207836_s_at | 38047_at |
| 207836_s_at | 38049_g_at |
| 207824_s_at | 32553_at |
| 207821_s_at | 36117_at |
| 207802_at | 36464_at |
| 207761_s_at | 38717_at |
| 207741_x_at | 32905_s_at |
| 207714_s_at | 39167_r_at |
| 207630_s_at | 32065_at |
| 207630_s_at | 32066_g_at |
| 207630_s_at | 32067_at |
| 207629_s_at | 40099_at |
| 207563_s_at | 38614_s_at |
| 207549_x_at | 38441_s_at |
| 207547_s_at | 38044_at |
| 207542_s_at | 36156_at |
| 207507_s_at | 34811_at |
| 207453_s_at | 38632_at |
| 207390_s_at | 31830_s_at |
| 207390_s_at | 31831_at |
| 207348_s_at | 1188_g_at |
| 207317_s_at | 36505_at |
| 207266_x_at | 31671_at |
| 207266_x_at | 31672_g_at |
| 207266_x_at | 333_s_at |
| 207266_x_at | 33867_s_at |
| 207260_at | 31685_at |
| 207172_s_at | 2087_s_at |
| 207172_s_at | 36976_at |
| 207124_s_at | 38176_at |
| 207121_s_at | 36926_at |
| 207071_s_at | 40077_at |
| 207001_x_at | 36629_at |
| 207001_x_at | 36630_at |
| 206938_at | 565_at |
| 206932_at | 32363_at |
| 206868_at | 34034_at |
| 206858_s_at | 40674_s_at |
| 206842_at | 40021_at |
| 206813_at | 36252_at |
| 206701_x_at | 1198_at |
| 206666_at | 36280_at |
| 206649_s_at | 34669_at |
| 206631_at | 828_at |
| 206580_s_at | 35347_at |
| 206558_at | 39608_at |
| 206558_at | 39609_at |
| 206459_s_at | 33684_at |
| 206458_s_at | 33684_at |
| 206434_at | 33596_at |

TABLE 17-continued

| probeID U133 | probeID U95A |
|---|---|
| 206433_s_at | 33596_at |
| 206429_at | 36345_g_at |
| 206429_at | 38247_at |
| 206385_s_at | 36965_at |
| 206382_s_at | 1088_at |
| 206382_s_at | 40023_at |
| 206377_at | 36319_at |
| 206375_s_at | 528_at |
| 206352_s_at | 41281_s_at |
| 206352_s_at | 41282_s_at |
| 206351_s_at | 41281_s_at |
| 206351_s_at | 41282_s_at |
| 206332_s_at | 1456_s_at |
| 206284_x_at | 32522_f_at |
| 206117_at | 36790_at |
| 206117_at | 36791_g_at |
| 206117_at | 36792_at |
| 206116_s_at | 36790_at |
| 206116_s_at | 36791_g_at |
| 206116_s_at | 36792_at |
| 206106_at | 983_at |
| 206076_at | 39447_f_at |
| 206070_s_at | 1234_at |
| 206065_s_at | 41422_at |
| 206030_at | 39654_at |
| 206009_at | 1508_at |
| 205980_s_at | 37117_at |
| 205963_s_at | 36541_at |
| 205961_s_at | 39243_s_at |
| 205942_s_at | 33278_at |
| 205942_s_at | 41149_at |
| 205942_s_at | 33279_s_at |
| 205937_at | 470_at |
| 205935_at | 38183_at |
| 205934_at | 1182_at |
| 205895_s_at | 36597_at |
| 205882_x_at | 33102_at |
| 205882_x_at | 33103_s_at |
| 205827_at | 37572_at |
| 205805_at | 213_at |
| 205803_s_at | 39123_s_at |
| 205803_s_at | 39125_at |
| 205782_at | 1380_at |
| 205782_at | 1466_s_at |
| 205780_at | 2011_s_at |
| 205780_at | 36891_at |
| 205776_at | 37874_at |
| 205743_at | 40024_at |
| 205741_s_at | 36467_g_at |
| 205741_s_at | 36469_at |
| 205741_s_at | 36470_s_at |
| 205730_s_at | 39597_at |
| 205709_s_at | 40217_s_at |
| 205709_s_at | 40218_at |
| 205683_x_at | 33321_r_at |
| 205645_at | 40663_at |
| 205620_at | 39979_at |
| 205611_at | 39588_at |
| 205608_s_at | 1929_at |
| 205608_s_at | 39315_at |
| 205575_at | 39920_r_at |
| 205573_s_at | 37808_at |
| 205548_s_at | 37218_at |
| 205547_s_at | 36931_at |
| 205505_at | 38218_at |
| 205480_s_at | 37373_at |
| 205475_at | 35837_at |
| 205438_at | 40524_at |
| 205433_at | 37841_at |
| 205431_s_at | 1831_at |
| 205430_at | 1831_at |
| 205407_at | 35234_at |
| 205404_at | 35702_at |
| 205384_at | 32109_at |
| 205382_s_at | 40282_s_at |
| 205348_s_at | 40318_at |
| 205329_s_at | 40605_at |
| 205325_at | 37191_at |
| 205304_s_at | 34428_at |
| 205303_at | 34428_at |
| 205294_at | 37760_at |
| 205294_at | 37761_at |
| 205262_at | 38225_at |
| 205262_at | 38858_at |
| 205249_at | 37863_at |
| 205225_at | 1681_at |
| 205221_at | 31844_at |
| 205219_s_at | 37825_at |
| 205200_at | 36569_at |
| 205168_at | 1319_at |
| 205160_at | 39648_at |
| 205158_at | 32664_at |
| 205157_s_at | 34301_r_at |
| 205155_s_at | 33630_s_at |
| 205132_at | 39063_at |
| 205120_s_at | 37223_at |
| 205116_at | 36917_at |
| 205110_s_at | 36232_at |
| 205110_s_at | 468_at |
| 205047_s_at | 36671_at |
| 205018_s_at | 33318_at |
| 205011_at | 38151_at |
| 205001_s_at | 38355_at |
| 204993_at | 38279_at |
| 204979_s_at | 36040_at |
| 204964_s_at | 33302_at |
| 204964_s_at | 33303_at |
| 204963_at | 33302_at |
| 204963_at | 33303_at |
| 204939_s_at | 38734_at |
| 204938_s_at | 38734_at |
| 204934_s_at | 37639_at |
| 204931_at | 37247_at |
| 204929_s_at | 32533_s_at |
| 204929_s_at | 32534_f_at |
| 204903_x_at | 37041_at |
| 204894_s_at | 33756_at |
| 204875_s_at | 35071_s_at |
| 204872_at | 38364_at |
| 204834_at | 39591_s_at |
| 204834_at | 39592_r_at |
| 204803_s_at | 1776_at |
| 204802_at | 1776_at |
| 204790_at | 1857_at |
| 204780_s_at | 37643_at |
| 204777_s_at | 38051_at |
| 204755_x_at | 401_s_at |
| 204754_at | 401_s_at |
| 204753_s_at | 401_s_at |
| 204751_x_at | 39302_at |
| 204749_at | 743_at |
| 204744_s_at | 40827_at |
| 204734_at | 37582_at |
| 204731_at | 1897_at |
| 204730_at | 37265_at |
| 204714_s_at | 35245_at |
| 204713_s_at | 35245_at |
| 204688_at | 41449_at |
| 204615_x_at | 36985_at |
| 204610_s_at | 41851_at |
| 204608_at | 36528_at |
| 204607_at | 35345_at |
| 204595_s_at | 41354_at |
| 204570_at | 39031_at |
| 204556_s_at | 36521_at |
| 204518_s_at | 37422_at |
| 204517_at | 37422_at |
| 204491_at | 38526_at |
| 204484_at | 41715_at |
| 204472_at | 37279_at |
| 204464_s_at | 1507_s_at |
| 204463_s_at | 1507_s_at |
| 204442_x_at | 33137_at |
| 204436_at | 36856_at |
| 204430_s_at | 34362_at |
| 204429_s_at | 34362_at |

TABLE 17-continued

| probeID U133 | probeID U95A |
|---|---|
| 204427_s_at | 36972_at |
| 204426_at | 36972_at |
| 204424_s_at | 38028_at |
| 204422_s_at | 1593_at |
| 204422_s_at | 41806_at |
| 204421_s_at | 1593_at |
| 204421_s_at | 41806_at |
| 204412_s_at | 33767_at |
| 204396_s_at | 1135_at |
| 204395_s_at | 1135_at |
| 204394_at | 33708_at |
| 204393_s_at | 32200_at |
| 204392_at | 251_at |
| 204352_at | 35238_at |
| 204345_at | 35168_f_at |
| 204345_at | 35169_at |
| 204344_s_at | 39099_at |
| 204341_at | 38881_i_at |
| 204341_at | 38882_r_at |
| 204331_s_at | 33214_at |
| 204319_s_at | 33121_g_at |
| 204312_x_at | 877_at |
| 204273_at | 1198_at |
| 204271_s_at | 1198_at |
| 204223_at | 37022_at |
| 204163_at | 35740_at |
| 204151_x_at | 32805_at |
| 204147_s_at | 37758_s_at |
| 204141_at | 296_at |
| 204141_at | 39331_at |
| 204141_at | 297_g_at |
| 204140_at | 32718_at |
| 204135_at | 31897_at |
| 204134_at | 31904_at |
| 204133_at | 31882_at |
| 204123_at | 1188_g_at |
| 204122_at | 38363_at |
| 204117_at | 37950_at |
| 204114_at | 753_at |
| 204100_at | 35846_at |
| 204099_at | 32565_at |
| 204083_s_at | 32312_at |
| 204083_s_at | 32313_at |
| 204083_s_at | 32314_g_at |
| 204069_at | 40763_at |
| 204059_s_at | 33644_at |
| 204059_s_at | 837_s_at |
| 204058_at | 33644_at |
| 204058_at | 837_s_at |
| 204045_at | 38317_at |
| 204042_at | 1058_at |
| 204038_s_at | 40387_at |
| 204037_at | 40387_at |
| 204031_s_at | 35745_f_at |
| 204031_s_at | 35746_r_at |
| 204030_s_at | 36536_at |
| 204005_s_at | 40621_at |
| 204000_at | 38176_at |
| 203973_s_at | 1052_s_at |
| 203966_s_at | 36501_at |
| 203966_s_at | 857_at |
| 203953_s_at | 33904_at |
| 203951_at | 34203_at |
| 203944_x_at | 32673_at |
| 203931_s_at | 39812_at |
| 203926_x_at | 37992_s_at |
| 203926_x_at | 37993_at |
| 203911_at | 1251_g_at |
| 203909_at | 36542_at |
| 203908_at | 35285_at |
| 203908_at | 35871_s_at |
| 203903_s_at | 35644_at |
| 203886_s_at | 32783_at |
| 203851_at | 1736_at |
| 203811_s_at | 158_at |
| 203811_s_at | 33533_at |
| 203810_at | 158_at |
| 203810_at | 33533_at |
| 203787_at | 32668_at |
| 203766_s_at | 37765_at |
| 203752_s_at | 1612_s_at |
| 203752_s_at | 41483_s_at |
| 203748_x_at | 31671_at |
| 203748_x_at | 31672_g_at |
| 203748_x_at | 333_s_at |
| 203748_x_at | 33867_s_at |
| 203739_at | 32034_at |
| 203733_at | 41637_at |
| 203729_at | 39182_at |
| 203725_at | 1911_s_at |
| 203722_at | 37331_g_at |
| 203710_at | 32778_at |
| 203710_at | 32779_s_at |
| 203710_at | 755_at |
| 203698_s_at | 40230_at |
| 203688_at | 38120_at |
| 203680_at | 37221_at |
| 203666_at | 32666_at |
| 203666_at | 33834_at |
| 203663_s_at | 41223_at |
| 203649_s_at | 37017_at |
| 203649_s_at | 614_at |
| 203641_s_at | 41755_at |
| 203638_s_at | 1143_s_at |
| 203638_s_at | 1363_at |
| 203638_s_at | 1145_g_at |
| 203620_s_at | 32224_at |
| 203592_s_at | 33900_at |
| 203586_s_at | 41774_at |
| 203585_at | 32139_at |
| 203582_s_at | 39244_at |
| 203582_s_at | 621_at |
| 203576_at | 41111_at |
| 203562_at | 37743_at |
| 203557_s_at | 34352_at |
| 203542_s_at | 40202_at |
| 203524_s_at | 36124_at |
| 203498_at | 32076_at |
| 203456_at | 34318_at |
| 203455_s_at | 1173_g_at |
| 203455_s_at | 34304_s_at |
| 203453_at | 35207_at |
| 203449_s_at | 1329_s_at |
| 203449_s_at | 32255_i_at |
| 203449_s_at | 32256_r_at |
| 203435_s_at | 1389_at |
| 203434_s_at | 1389_at |
| 203430_at | 41454_at |
| 203423_at | 38634_at |
| 203415_at | 37569_at |
| 203414_at | 37565_at |
| 203413_at | 32598_at |
| 203411_s_at | 37378_r_at |
| 203397_s_at | 36483_at |
| 203397_s_at | 36484_at |
| 203370_s_at | 39530_at |
| 203369_x_at | 39530_at |
| 203324_s_at | 339_at |
| 203324_s_at | 40168_at |
| 203320_at | 39428_at |
| 203311_s_at | 33152_at |
| 203304_at | 37678_at |
| 203303_at | 36921_at |
| 203300_x_at | 41549_s_at |
| 203296_s_at | 34377_at |
| 203243_s_at | 40060_r_at |
| 203242_s_at | 40060_r_at |
| 203241_at | 39429_at |
| 203233_at | 404_at |
| 203219_s_at | 34310_at |
| 203218_at | 1238_at |
| 203218_at | 38431_at |
| 203197_s_at | 39743_at |
| 203196_at | 1931_at |
| 203196_at | 34955_at |
| 203186_s_at | 38087_s_at |

TABLE 17-continued

| probeID U133 | probeID U95A |
|---|---|
| 203180_at | 36686_at |
| 203174_s_at | 35765_at |
| 203167_at | 1375_s_at |
| 203167_at | 34722_at |
| 203151_at | 35917_at |
| 203140_at | 40091_at |
| 203139_at | 40049_at |
| 203138_at | 41855_at |
| 203099_s_at | 32111_at |
| 203088_at | 39038_at |
| 203068_at | 35190_at |
| 203066_at | 35350_at |
| 203065_s_at | 36119_at |
| 203063_at | 37384_at |
| 203043_at | 39168_at |
| 203041_s_at | 38402_at |
| 203041_s_at | 38403_at |
| 203033_x_at | 32546_at |
| 203007_x_at | 39396_at |
| 202995_s_at | 38026_at |
| 202995_s_at | 38027_at |
| 202994_s_at | 38026_at |
| 202994_s_at | 38027_at |
| 202992_at | 37394_at |
| 202978_s_at | 41495_at |
| 202949_s_at | 38422_s_at |
| 202946_s_at | 37755_at |
| 202941_at | 34893_at |
| 202936_s_at | 33436_at |
| 202935_s_at | 33436_at |
| 202931_x_at | 459_s_at |
| 202929_s_at | 33689_s_at |
| 202929_s_at | 41180_i_at |
| 202921_s_at | 39850_at |
| 202916_s_at | 35318_at |
| 202915_s_at | 35318_at |
| 202908_at | 35164_at |
| 202898_at | 32092_at |
| 202890_at | 39732_at |
| 202889_x_at | 39732_at |
| 202886_s_at | 41429_at |
| 202884_s_at | 41429_at |
| 202836_s_at | 33631_at |
| 202836_s_at | 33632_g_at |
| 202828_s_at | 34747_at |
| 202812_at | 31816_at |
| 202802_at | 37722_s_at |
| 202796_at | 33719_at |
| 202796_at | 36452_at |
| 202795_x_at | 34046_at |
| 202787_s_at | 1637_at |
| 202786_at | 40966_at |
| 202784_s_at | 41722_at |
| 202779_s_at | 893_at |
| 202770_s_at | 1913_at |
| 202770_s_at | 37723_at |
| 202769_at | 1913_at |
| 202769_at | 37723_at |
| 202766_s_at | 32535_at |
| 202765_s_at | 32535_at |
| 202760_s_at | 35985_at |
| 202759_s_at | 35985_at |
| 202748_at | 32700_at |
| 202740_at | 37713_at |
| 202738_s_at | 37392_at |
| 202736_s_at | 32559_s_at |
| 202736_s_at | 32560_s_at |
| 202734_at | 36116_at |
| 202732_at | 34376_at |
| 202729_s_at | 1495_at |
| 202728_s_at | 1495_at |
| 202722_s_at | 32626_at |
| 202721_s_at | 32626_at |
| 202719_s_at | 32134_at |
| 202688_at | 1715_at |
| 202686_s_at | 38433_at |
| 202685_s_at | 38433_at |
| 202655_at | 36615_at |
| 202637_s_at | 32640_at |
| 202609_at | 1467_at |
| 202606_s_at | 32219_at |
| 202605_at | 33308_at |
| 202599_s_at | 40088_at |
| 202598_at | 39712_at |
| 202583_s_at | 39547_at |
| 202579_x_at | 35737_at |
| 202579_x_at | 35738_at |
| 202566_s_at | 40069_at |
| 202565_s_at | 40069_at |
| 202555_s_at | 32847_at |
| 202554_s_at | 1121_g_at |
| 202554_s_at | 32798_at |
| 202548_s_at | 40828_at |
| 202542_s_at | 39734_at |
| 202534_x_at | 37913_at |
| 202522_at | 353_at |
| 202506_at | 38409_at |
| 202504_at | 1898_at |
| 202499_s_at | 36979_at |
| 202497_x_at | 36979_at |
| 202465_at | 31609_s_at |
| 202450_s_at | 128_at |
| 202450_s_at | 129_g_at |
| 202440_s_at | 37745_s_at |
| 202440_s_at | 37746_r_at |
| 202428_x_at | 37692_at |
| 202427_s_at | 37000_at |
| 202410_x_at | 1664_at |
| 202407_s_at | 40904_at |
| 202404_s_at | 32305_at |
| 202404_s_at | 32306_g_at |
| 202404_s_at | 32307_s_at |
| 202403_s_at | 32305_at |
| 202403_s_at | 32306_g_at |
| 202403_s_at | 32307_s_at |
| 202401_s_at | 40109_at |
| 202395_at | 38719_at |
| 202388_at | 37701_at |
| 202371_at | 32251_at |
| 202362_at | 1848_at |
| 202350_s_at | 32239_at |
| 202296_s_at | 41551_at |
| 202296_s_at | 41552_g_at |
| 202291_s_at | 41287_s_at |
| 202286_s_at | 291_s_at |
| 202286_s_at | 41286_at |
| 202283_at | 40856_at |
| 202274_at | 1197_at |
| 202273_at | 1771_s_at |
| 202269_x_at | 35735_at |
| 202266_at | 34825_at |
| 202262_x_at | 36131_at |
| 202262_x_at | 38621_at |
| 202254_at | 40805_at |
| 202242_at | 38408_at |
| 202228_s_at | 35747_at |
| 202222_s_at | 40776_at |
| 202202_s_at | 37671_at |
| 202201_at | 37002_at |
| 202193_at | 38618_at |
| 202180_s_at | 38064_at |
| 202161_at | 175_s_at |
| 202159_at | 34291_at |
| 202148_s_at | 37741_at |
| 202138_x_at | 41250_at |
| 202133_at | 33876_at |
| 202132_at | 33876_at |
| 202123_s_at | 1635_at |
| 202123_s_at | 32974_at |
| 202123_s_at | 39730_at |
| 202123_s_at | 1636_g_at |
| 202123_s_at | 32975_g_at |
| 202117_at | 39700_at |
| 202117_at | 552_at |
| 202117_at | 553_g_at |
| 202105_at | 34391_at |

TABLE 17-continued

| probeID U133 | probeID U95A |
|---|---|
| 202092_s_at | 33198_at |
| 202089_s_at | 1798_at |
| 202081_at | 36097_at |
| 202075_s_at | 40081_at |
| 202074_s_at | 41742_s_at |
| 202074_s_at | 41744_at |
| 202073_at | 41742_s_at |
| 202073_at | 41744_at |
| 202069_s_at | 36195_at |
| 202023_at | 40425_at |
| 202021_x_at | 33850_at |
| 202005_at | 35309_at |
| 201995_at | 222_at |
| 201993_x_at | 32393_s_at |
| 201980_s_at | 32544_s_at |
| 201977_s_at | 35744_at |
| 201968_s_at | 32210_at |
| 201958_s_at | 34925_at |
| 201958_s_at | 41137_at |
| 201957_at | 34925_at |
| 201957_at | 41137_at |
| 201955_at | 1923_at |
| 201955_at | 39251_at |
| 201947_s_at | 35759_at |
| 201946_s_at | 35759_at |
| 201934_at | 32248_at |
| 201931_at | 40509_at |
| 201923_at | 38435_at |
| 201912_s_at | 33932_at |
| 201909_at | 41214_at |
| 201900_s_at | 38780_at |
| 201892_s_at | 36624_at |
| 201869_s_at | 32554_s_at |
| 201869_s_at | 32555_at |
| 201868_s_at | 32554_s_at |
| 201868_s_at | 32555_at |
| 201867_s_at | 32554_s_at |
| 201867_s_at | 32555_at |
| 201858_s_at | 32227_at |
| 201852_x_at | 32488_at |
| 201848_s_at | 38010_at |
| 201843_s_at | 32551_at |
| 201842_s_at | 32551_at |
| 201841_s_at | 36785_at |
| 201839_s_at | 575_s_at |
| 201828_x_at | 33856_at |
| 201805_at | 34346_at |
| 201792_at | 39069_at |
| 201787_at | 38026_at |
| 201787_at | 38027_at |
| 201785_at | 37402_at |
| 201761_at | 40074_at |
| 201760_s_at | 40167_s_at |
| 201758_at | 147_at |
| 201744_s_at | 38038_at |
| 201743_at | 36661_s_at |
| 201742_x_at | 36098_at |
| 201738_at | 33351_at |
| 201735_s_at | 40880_r_at |
| 201723_s_at | 38041_at |
| 201719_s_at | 32585_at |
| 201718_s_at | 32585_at |
| 201694_s_at | 789_at |
| 201689_s_at | 33840_at |
| 201688_s_at | 33840_at |
| 201667_at | 32531_at |
| 201662_s_at | 33880_at |
| 201662_s_at | 33881_at |
| 201660_at | 33880_at |
| 201660_at | 33881_at |
| 201655_s_at | 32845_at |
| 201650_at | 40899_at |
| 201647_s_at | 33823_at |
| 201641_at | 39061_at |
| 201627_s_at | 35303_at |
| 201625_s_at | 35303_at |
| 201621_at | 37005_at |
| 201617_x_at | 41738_at |
| 201617_x_at | 41739_s_at |
| 201616_s_at | 41738_at |
| 201616_s_at | 41739_s_at |
| 201615_x_at | 41738_at |
| 201615_x_at | 41739_s_at |
| 201609_x_at | 41775_at |
| 201604_s_at | 40438_at |
| 201596_x_at | 35766_at |
| 201583_s_at | 40851_r_at |
| 201582_at | 40851_r_at |
| 201577_at | 1521_at |
| 201577_at | 39073_at |
| 201568_at | 34400_at |
| 201560_at | 33891_at |
| 201559_s_at | 33891_at |
| 201543_s_at | 41451_s_at |
| 201540_at | 32542_at |
| 201539_s_at | 32542_at |
| 201538_s_at | 41225_at |
| 201538_s_at | 41226_at |
| 201537_s_at | 41225_at |
| 201537_s_at | 41226_at |
| 201536_at | 41225_at |
| 201536_at | 41226_at |
| 201524_x_at | 1660_at |
| 201524_x_at | 36604_at |
| 201523_x_at | 1660_at |
| 201523_x_at | 36604_at |
| 201522_x_at | 34842_at |
| 201521_s_at | 32789_at |
| 201516_at | 241_g_at |
| 201505_at | 581_at |
| 201497_x_at | 32582_at |
| 201497_x_at | 37407_s_at |
| 201497_x_at | 767_at |
| 201497_x_at | 773_at |
| 201497_x_at | 774_g_at |
| 201496_x_at | 32582_at |
| 201496_x_at | 37407_s_at |
| 201496_x_at | 767_at |
| 201496_x_at | 773_at |
| 201496_x_at | 774_g_at |
| 201495_x_at | 32582_at |
| 201495_x_at | 37407_s_at |
| 201495_x_at | 767_at |
| 201495_x_at | 773_at |
| 201495_x_at | 774_g_at |
| 201482_at | 1257_s_at |
| 201475_x_at | 39342_at |
| 201460_at | 36179_at |
| 201460_at | 36180_s_at |
| 201459_at | 35758_at |
| 201457_x_at | 34783_s_at |
| 201457_x_at | 41547_at |
| 201446_s_at | 33852_at |
| 201438_at | 38077_at |
| 201431_s_at | 36149_at |
| 201430_s_at | 36149_at |
| 201421_s_at | 38987_at |
| 201420_s_at | 38987_at |
| 201416_at | 33131_at |
| 201403_s_at | 39018_at |
| 201397_at | 34367_at |
| 201391_at | 1468_at |
| 201387_at | 36990_at |
| 201386_s_at | 35306_at |
| 201380_at | 40119_at |
| 201375_s_at | 924_s_at |
| 201361_at | 39693_at |
| 201361_at | 39694_at |
| 201347_x_at | 40133_s_at |
| 201339_s_at | 36688_at |
| 201337_s_at | 35783_at |
| 201327_s_at | 38416_at |
| 201312_s_at | 39714_at |
| 201311_s_at | 39714_at |
| 201301_s_at | 37374_at |
| 201300_s_at | 36159_s_at |

TABLE 17-continued

| probeID U133 | probeID U95A |
|---|---|
| 201293_x_at | 33667_at |
| 201289_at | 38772_at |
| 201284_s_at | 37401_g_at |
| 201272_at | 36589_at |
| 201268_at | 1980_s_at |
| 201268_at | 33415_at |
| 201266_at | 39425_at |
| 201264_at | 38647_at |
| 201263_at | 38473_at |
| 201240_s_at | 37359_at |
| 201234_at | 35365_at |
| 201221_s_at | 40875_s_at |
| 201215_at | 34793_s_at |
| 201193_at | 39023_at |
| 201185_at | 719_g_at |
| 201161_s_at | 39839_at |
| 201155_s_at | 34369_at |
| 201153_s_at | 34306_at |
| 201152_s_at | 34306_at |
| 201151_s_at | 34306_at |
| 201150_s_at | 1034_at |
| 201150_s_at | 1035_g_at |
| 201149_s_at | 1034_at |
| 201149_s_at | 1035_g_at |
| 201148_s_at | 1034_at |
| 201148_s_at | 1035_g_at |
| 201147_s_at | 1034_at |
| 201147_s_at | 1035_g_at |
| 201146_at | 853_at |
| 201144_s_at | 1154_at |
| 201144_s_at | 39784_at |
| 201142_at | 1154_at |
| 201142_at | 39784_at |
| 201137_s_at | 38095_i_at |
| 201130_s_at | 977_s_at |
| 201127_s_at | 40881_at |
| 201120_s_at | 38802_at |
| 201115_at | 1470_at |
| 201108_s_at | 115_at |
| 201105_at | 33412_at |
| 201098_at | 36677_at |
| 201091_s_at | 38084_at |
| 201091_s_at | 38085_at |
| 201079_at | 34885_at |
| 201069_at | 39007_at |
| 201061_s_at | 40419_at |
| 201060_x_at | 40419_at |
| 201058_s_at | 39145_at |
| 201042_at | 231_at |
| 201042_at | 38404_at |
| 201040_at | 37307_at |
| 201037_at | 39175_at |
| 201022_s_at | 38385_at |
| 201021_s_at | 38385_at |
| 201020_at | 1424_s_at |
| 201014_s_at | 39056_at |
| 201013_s_at | 39056_at |
| 201005_at | 39389_at |
| 201001_s_at | 36959_at |
| 200996_at | 35271_at |
| 200986_at | 39775_at |
| 200985_s_at | 39351_at |
| 200982_s_at | 39082_at |
| 200974_at | 32755_at |
| 200971_s_at | 37035_at |
| 200970_s_at | 37035_at |
| 200968_s_at | 35823_at |
| 200931_s_at | 36601_at |
| 200930_s_at | 36601_at |
| 200923_at | 37754_at |
| 200911_s_at | 40841_at |
| 200910_at | 40774_at |
| 200907_s_at | 41191_at |
| 200906_s_at | 41191_at |
| 200904_at | 32321_at |
| 200903_s_at | 40821_at |
| 200897_s_at | 41191_at |
| 200894_s_at | 38729_at |
| 200889_s_at | 34648_at |
| 200886_s_at | 41221_at |
| 200884_at | 40862_i_at |
| 200884_at | 40863_r_at |
| 200863_s_at | 36660_at |
| 200859_x_at | 32749_s_at |
| 200859_x_at | 32750_r_at |
| 200836_s_at | 242_at |
| 200836_s_at | 243_g_at |
| 200836_s_at | 32226_at |
| 200835_s_at | 242_at |
| 200835_s_at | 243_g_at |
| 200835_s_at | 32226_at |
| 200823_x_at | 33674_at |
| 200820_at | 1312_at |
| 200820_at | 32584_at |
| 200813_s_at | 32569_at |
| 200808_s_at | 36958_at |
| 200807_s_at | 37720_at |
| 200806_s_at | 37720_at |
| 200803_s_at | 33988_at |
| 200803_s_at | 33989_f_at |
| 200801_x_at | 32318_s_at |
| 200801_x_at | AFFX-HSAC07/X00351_3_at |
| 200801_x_at | AFFX-HSAC07/X00351_3_st |
| 200801_x_at | AFFX-HSAC07/X00351_5_at |
| 200801_x_at | AFFX-HSAC07/X00351_5_st |
| 200801_x_at | AFFX-HSAC07/X00351_M_at |
| 200795_at | 36627_at |
| 200790_at | 1081_at |
| 200790_at | 36203_at |
| 200788_s_at | 32260_at |
| 200778_s_at | 40281_at |
| 200762_at | 40607_at |
| 200750_s_at | 1839_at |
| 200750_s_at | 38708_at |
| 200750_s_at | 1840_g_at |
| 200715_x_at | 35119_at |
| 200700_s_at | 39080_at |
| 200698_at | 39080_at |
| 200696_s_at | 32612_at |
| 200693_at | 409_at |
| 200672_x_at | 39556_at |
| 200671_s_at | 39556_at |
| 200670_at | 39755_at |
| 200670_at | 39756_g_at |
| 200669_s_at | 504_at |
| 200665_s_at | 671_at |
| 200657_at | 37740_r_at |
| 200652_at | 36147_at |
| 200644_at | 36174_at |
| 200625_s_at | 935_at |
| 200622_x_at | 955_at |
| 200621_at | 38700_at |
| 200620_at | 39033_at |
| 200611_s_at | 38736_at |
| 200609_s_at | 38736_at |
| 200604_s_at | 227_g_at |
| 200604_s_at | 41768_at |
| 200082_s_at | 34646_at |
| 200074_s_at | 31907_at |
| 200068_s_at | 40125_at |
| 200066_at | 218_at |
| 200059_s_at | 1394_at |
| 200059_s_at | 37309_at |
| 200055_at | 868_at |
| 200052_s_at | 36189_at |
| 200024_at | 32437_at |
| 200015_s_at | 40281_at |
| 200008_s_at | 35307_at |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08781750B2). An electronic copy of the "Sequence Listing" will also be available from the USPTO upon request and payment of the fee set forth in 37 CFR 1.19(b)(3).

What is claimed is:

1. A method of determining gene expression levels in prostate tissue samples from subjects diagnosed as having prostate cancer, comprising the steps of:
   (a) assaying the relative content of malignant and non-malignant cells within each of two or more heterogeneous prostate tissue samples from subjects diagnosed as having prostate cancer, wherein at least two of the samples do not contain the same relative content of malignant and non-malignant cells, and wherein the assaying is done without physically separating the malignant from the non-malignant cells in the sample;
   (b) measuring the overall level of each of a plurality of different RNA expression analytes extracted from each prostate tissue sample without physically separating the malignant from the non-malignant cells in the sample, such that each measured level corresponds to the combined expression of an RNA expression analyte in malignant and nonmalignant cells;
   (c) determining a linear or non-linear regression relationship between the relative content of malignant and non-malignant cells in each sample and the measured overall levels of the plurality of different RNA analytes in each sample to provide a quantitative relationship therebetween;
   (d) using the regression relationship determined in step (c) to calculate the level of each of the plurality of different RNA expression analytes in the malignant cells and in the non-malignant cells separately, wherein the calculated levels of analytes correspond to the gene expression levels; and
   (e) outputting to a display information regarding the calculated levels of analytes.

2. The method of claim 1, further comprising a step of identifying genes differentially expressed in malignant cells relative to non-malignant cells, or in non-malignant cells relative to malignant cells.

3. The method of claim 1, wherein the step of determining the regression relationship further comprises determining the regression of overall levels of each RNA expression analyte on the proportion of malignant and non-malignant cells.

4. The method of claim 1, wherein step (c) comprises determining a linear regression relationship between the relative content of malignant and non-malignant cells in each sample and the measured overall levels of the plurality of different RNA analytes in each sample to provide a quantitative relationship therebetween, using Equation 1:

$$G_{jk} = \sum_j x_{ki} \beta_{ij} + \varepsilon_{jk}$$

assuming that the contribution to gene expression of any one cell type depends only on the proportion of that cell type and its corresponding characteristic cell-type expression level, $\beta_{ij}$, wherein $G_{jk}$ is the average expression level of gene j in a sample k, and is the average of $\beta_{ij}$ weighted by cell type fractions $x_{ki}$.

* * * * *